US011142792B2

(12) United States Patent
Turner et al.

(10) Patent No.: US 11,142,792 B2
(45) Date of Patent: *Oct. 12, 2021

(54) SINGLE-MOLECULE NANOFET SEQUENCING SYSTEMS AND METHODS

(71) Applicant: Pacific Biosciences of California, Inc., Menlo Park, CA (US)

(72) Inventors: Stephen Turner, Eugene, OR (US); Jonas Korlach, Camas, WA (US); Satwik Kamtekar, Mountain View, CA (US); Jeremiah Hanes, Woodside, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 50 days.

This patent is subject to a terminal disclaimer.

(21) Appl. No.: 16/137,357

(22) Filed: Sep. 20, 2018

(65) Prior Publication Data

US 2019/0106741 A1 Apr. 11, 2019

Related U.S. Application Data

(63) Continuation of application No. 15/227,661, filed on Aug. 3, 2016, now Pat. No. 10,125,391.
(Continued)

(51) Int. Cl.
*C12Q 1/68* (2018.01)
*C12Q 1/6869* (2018.01)
(Continued)

(52) U.S. Cl.
CPC ............ *C12Q 1/6869* (2013.01); *B82Y 10/00* (2013.01); *B82Y 15/00* (2013.01); *C12Q 1/6874* (2013.01);
(Continued)

(58) Field of Classification Search
CPC ........ C12Q 2565/607; C12Q 2521/101; C12Q 2521/543; C12Q 1/001; C12Q 1/6869;
(Continued)

(56) References Cited

U.S. PATENT DOCUMENTS 5,143,854 A 9/1992 Pirrung et al.
5,723,584 A 3/1998 Schatz
(Continued)

FOREIGN PATENT DOCUMENTS

EP 2035584 B1 1/2011
EP 1963530 B1 7/2011
(Continued)

OTHER PUBLICATIONS

U.S. Appl. No. 62/069,198, filed Oct. 27, 2014. (Year: 2014).*
(Continued)

*Primary Examiner* — Betty J Forman
(74) *Attorney, Agent, or Firm* — Robert H. Reamey

(57) ABSTRACT

Real time electronic sequencing devices, chips, and systems are described. Arrays of nanoFET devices are used to provide sequence information about a template nucleic acid in a polymerase-template complex bound to the nanoFET. The nanoFET devices typically have a source, a drain and a gate comprising a nanowire. A single polymerase enzyme complex comprising a polymerase enzyme complexed with the template nucleic acid is bound to the gate. The polymerase is bound to the gate non-covalently through a polymeric binding agent that has two strands, each strand interacting with the nanowire such that the polymerase is in a central location between the strands with the polymeric binding agent extending away from the polymerase complex along the nanowire in both directions.

18 Claims, 25 Drawing Sheets

Related U.S. Application Data

(60) Provisional application No. 62/201,731, filed on Aug. 6, 2015, provisional application No. 62/239,176, filed on Oct. 8, 2015.

(51) Int. Cl.
    *B82Y 10/00*           (2011.01)
    *B82Y 15/00*           (2011.01)
    *C12Q 1/6874*          (2018.01)
    *G01N 27/414*          (2006.01)
    *G11C 19/28*           (2006.01)
    *H01L 29/06*           (2006.01)
    *H01L 29/16*           (2006.01)

(52) U.S. Cl.
    CPC ..... *G01N 27/4145* (2013.01); *G01N 27/4146* (2013.01); *G01N 27/4148* (2013.01); *G11C 19/28* (2013.01); *H01L 29/0669* (2013.01); *H01L 29/1606* (2013.01); *H01L 29/0673* (2013.01)

(58) Field of Classification Search
    CPC ......... C12Q 2563/157; G01N 27/4145; G01N 27/4146; G01N 27/4148; G01N 27/00; B01L 2300/0896
    See application file for complete search history.

(56) References Cited

U.S. PATENT DOCUMENTS

| | | | |
|---|---|---|---|
| 5,874,239 A | 2/1999 | Schatz | |
| 5,932,433 A | 8/1999 | Schatz | |
| 6,153,442 A | 11/2000 | Pirio et al. | |
| 6,265,552 B1 | 7/2001 | Schatz | |
| 6,828,800 B2 | 12/2004 | Reich et al. | |
| 7,056,661 B2 | 6/2006 | Korlach et al. | |
| 7,141,676 B1 | 11/2006 | Wilbur et al. | |
| 7,315,019 B2 | 1/2008 | Turner et al. | |
| 7,763,423 B2 | 7/2010 | Roitman et al. | |
| 7,888,013 B2 | 2/2011 | Miyahara et al. | |
| 7,948,015 B2 | 5/2011 | Rothberg et al. | |
| 7,981,604 B2 | 7/2011 | Quake | |
| 7,981,632 B2 | 7/2011 | Schmidt | |
| 7,993,891 B2 | 8/2011 | Roitman et al. | |
| 8,034,222 B2 | 10/2011 | Myung et al. | |
| 8,133,672 B2 | 3/2012 | Bjornson et al. | |
| 8,137,942 B2 | 3/2012 | Roitman et al. | |
| 8,193,123 B2 | 6/2012 | Rank et al. | |
| 8,232,584 B2 | 7/2012 | Lieber et al. | |
| 8,252,910 B2 | 8/2012 | Korlach et al. | |
| 8,389,676 B2 | 3/2013 | Christians | |
| 8,652,779 B2 | 2/2014 | Turner et al. | |
| 8,703,497 B2 | 4/2014 | Sun et al. | |
| 8,864,969 B2 | 10/2014 | Liu et al. | |
| 8,871,921 B2 | 10/2014 | O'Halloran | |
| 8,961,757 B2 | 2/2015 | Nuckolls et al. | |
| 9,017,937 B1 | 4/2015 | Turner et al. | |
| 9,040,237 B2 | 5/2015 | Koo et al. | |
| 9,063,081 B2 | 6/2015 | Sauer et al. | |
| 9,228,967 B2 | 1/2016 | Sauer et al. | |
| 9,238,835 B2 | 1/2016 | Sun et al. | |
| 9,341,592 B2 | 5/2016 | Takulapalla et al. | |
| 9,708,656 B2 | 7/2017 | Turner et al. | |
| 9,868,987 B2 | 1/2018 | Turner | |
| 10,125,391 B2* | 11/2018 | Turner ................... | B82Y 15/00 |
| 10,934,583 B2 | 3/2021 | Turner | |
| 2001/0055766 A1 | 12/2001 | Aristarhov et al. | |
| 2005/0106587 A1 | 5/2005 | Klapproth et al. | |
| 2006/0199193 A1 | 9/2006 | Koo et al. | |
| 2006/0246497 A1 | 11/2006 | Huang et al. | |
| 2006/0269927 A1* | 11/2006 | Lieber ................... | C12Q 1/6825 |
| | | | 435/6.12 |
| 2009/0181381 A1 | 7/2009 | Oldman et al. | |
| 2009/0208922 A1 | 8/2009 | Choi et al. | |
| 2009/0233291 A1 | 9/2009 | Chen et al. | |
| 2010/0035254 A1 | 2/2010 | Williams | |
| 2010/0167299 A1 | 7/2010 | Korlach et al. | |
| 2010/0331194 A1 | 12/2010 | Turner et al. | |
| 2011/0014151 A1 | 1/2011 | Nilsson et al. | |
| 2011/0171655 A1 | 7/2011 | Esfandyarpour et al. | |
| 2011/0174620 A1 | 7/2011 | Choi et al. | |
| 2011/0177496 A1* | 7/2011 | Williams ............. | C12Q 1/6869 |
| | | | 435/6.1 |
| 2011/0236984 A1 | 9/2011 | Sun et al. | |
| 2011/0319276 A1 | 12/2011 | Liu et al. | |
| 2012/0021918 A1 | 1/2012 | Bashir et al. | |
| 2012/0052490 A1 | 3/2012 | Eid et al. | |
| 2012/0244537 A1 | 9/2012 | Sun et al. | |
| 2013/0052130 A1 | 2/2013 | Davis et al. | |
| 2013/0078622 A1 | 3/2013 | Collins et al. | |
| 2013/0109577 A1 | 5/2013 | Korlach et al. | |
| 2013/0165328 A1 | 6/2013 | Previte et al. | |
| 2013/0225416 A1 | 8/2013 | Altmann et al. | |
| 2013/0285680 A1 | 10/2013 | Sorgenfrei et al. | |
| 2013/0316912 A1 | 11/2013 | Bjornson | |
| 2013/0337567 A1 | 12/2013 | Shin et al. | |
| 2014/0178862 A1 | 6/2014 | Su et al. | |
| 2014/0235462 A1 | 8/2014 | Kotseraglou et al. | |
| 2014/0252460 A1 | 9/2014 | Lee et al. | |
| 2015/0017655 A1 | 1/2015 | Huang et al. | |
| 2015/0065353 A1 | 3/2015 | Turner et al. | |
| 2015/0093849 A1 | 4/2015 | Shepard et al. | |
| 2015/0171326 A1 | 6/2015 | Guo et al. | |
| 2016/0011186 A1 | 1/2016 | Oldham et al. | |
| 2016/0017416 A1 | 1/2016 | Boyanov et al. | |

FOREIGN PATENT DOCUMENTS

| | | |
|---|---|---|
| WO | 1991007087 A1 | 5/1991 |
| WO | 1999060400 A1 | 11/1999 |
| WO | 2008051530 A2 | 5/2008 |
| WO | 2009006445 A2 | 1/2009 |
| WO | 2011082419 A2 | 7/2011 |
| WO | 2012065043 A2 | 5/2012 |
| WO | 2012097074 A2 | 7/2012 |
| WO | 2013056241 A1 | 4/2013 |
| WO | 2014024041 A1 | 2/2014 |
| WO | 2014149779 A1 | 9/2014 |
| WO | 2014182630 A1 | 11/2014 |
| WO | 2016010975 A2 | 1/2016 |

OTHER PUBLICATIONS

Aime, et al., "High Sensitivity Lanthanide (III) Based Probes for MR-Medical Imaging," Coordination Chemistry Reviews (2006) 250:1562-1579.

Akhterov, et al., "Observing Lysozyme's Closing and Opening Motions for High-Resolution Single-Molecule Enzymology," ACS Chemical Biology (2015) 10:1495-1501.

Alivisatos, et al., "Nanotools for Neuroscience and Brain Activity Mapping," ACS Nano (2013) 7(3):1850-1866.

Balasubramanian and Burghard, "Chemically Functionalized Carbon Nanotubes," Small (2005) 1(2):180-192.

Beckett, et al., "A Minimal Peptide Substrate in Biotin Holoenzyme Synthetase-Catalyzed Biotinylation," Protein Science (1999) 8:921-929.

Besteman, et al., "Enzyme-Coated Carbon Nanotubes as Single-Molecule Biosensors," Nano Letters (2003) 3(6):727-30.

Bouilly, et al., "Single-Molecule Reaction Chemistry in Patterned Nanowells," Nano Letters (2016) 16:4679-85.

Bunimovich, et al., "Quantitative Real-Time Measurements of DNA Hybridization with Alkylated Nonoxidized Silicon Nanowires in Electrolyte Solution," J. Am. Chem. Soc. (2006) 128:16323-16331.

Bushmaker, et al., "Single-Ion Adsorption and Switching in Carbon Nanotubes," Nature Communications (2016) 7:10475 DOI: 10.1038/ncomms10475.

Calvaresi, et al., "The Devil and Holy Water: Protein and Carbon Nanotube Hybrids," Accounts of Chemical Research (2012) A-J.

Chen, et al., "DNA Sequencing Using Electrical Conductance Measurements of a DNA Polymerase," Nature Nanotechnology (2013) DOI: 10.1038/NNANO.2013.71.

(56) References Cited

OTHER PUBLICATIONS

Chen, et al., "Silicon Nanowire Field-Effect Transistor-Based Biosensors for Biomedical Diagnosis and Cellular Recording Investigation," Nano Today (2011) 6(2):131-154.
Chivers, et al.,"A Streptavidin Variant with Slower Biotin Dissocation and Increased Mechanostability," Nat. Methods (2010) 7(5):391-393.
Choi, et al., "Dissecting Single-Molecule Signal Transduction in Carbon Nanotube Circuits with Protein Engineering," Nano Lett (2013) 13(2):625-631.
Choi, et al., "Single Molecule Dynamics of Lysozyme Processing Distinguishes Linear and Cross-Linked Peptidoglycan Substrates," J. Am. Chem. Soc. (2012) 134(4):2032-2035.
Choi, et al., "Single-Molecule Lysozyme Dynamics Monitored by an Electronic Circuit," Science (2012) 335:319-324.
Derenskyi, et al., "Carbon Nanotube Network Ambipolar Field-Effect Transistors with 108 On/Off Ratio," Advanced Materials (2014) 26:5969-75.
Dietrich, et al., "Tethered Particle Motion Mediated by Scattering From Gold Nanoparticles and Darkfield Microscopy," Journal of Nanophotonics (2009) DOI: 10.1117/1.3174445.
Eid et al., "Real-Time DNA Sequencing From Single Polymerase Molecules," Science (2009) 323:133-138.
Elnathan, et al., "Biorecognition Layer Engineering: Overcoming Screening Limitaitons of Nanowire-Based FET Devices," NanoLetts (2012) 12:5245-54.
Farah, et al., "Point Mutagenesis and Cocrystallization of Wild-Type and Mutant Proteins: A Study of Solid-Phase Coexistence in Two-Dimensional Protein Arrays," Langmuir (2001) 17:5731-5735.
Fierer, et al., "SpyLigase Peptide-Peptide Ligation Polymerizes Affibodies to Enhance Magnetic Cancer Cell Capture," Proc. Natl. Acad. USA (2014) E1176-E1181.
Furukawa, et al., "Development of Novel Yeast Cell Surface Display System for Homo-Oligomeric Protein by Coexpression of Native and Anchored Subunits," Biotechnol. Prog. (2006) 22:994-997.
Gao, et al., "General Strategy for Biodetection in High Ionic Strength Solutions Using Transistor-Based Nanoelectronic Sensors," Nano Letters (2015) 15:2143-2148.
Green, "Avidin," Adv. Protein Res. (1975) 29:85-133.
Grigoryan, et al., "Computational Design of Virus-Like Protein Assemblies on Carbon Nanotube Surfaces," Science (2011) 332:1071-1076.
He, et al., "Direct Measurement of Single-Molecule DNA Hybridization Dynamics with Single-Base Resolution," Angew. Chem. Int. (2016) 55:9036-9040.
He, et al., "Single Nucleotide Plymorphism Cenotyping in Single-Molecule Electronic Circuits," Adv. Sci. (2017) 4:1700158.
Holmberg, et al., "The Biotin-Streptavidin Interaction can be Reversibly Broken Using Water at Elevated Temperatures," Electrophoresis (2005) 26:501-510.
Horton, et al., "Engineering Hybrid Genes Without the Use of Restriction Enzymes: Gene Splicing by Overlap Extension," Gene (1989) 77(1):61-8.
Howarth et al., "Imaging Proteins in Live Mammalian Cells with Biotin Ligase and Monovalent Streptavidin," Nature Protocols (2008) 3(3):534-545.
Howarth, et al., "A Monovalent Streptavidin with Single Femtomolar Biotin Binding Site," Nature Methods (2006) 3(4):267-73.
Hughes and Walsh, "What Makes a Good Graphene-Binding Peptide? Adsorption of Amino Acids and Peptides at Aqueous Graphene Interfaces," J. Mater. Chem. B. (2015) 3:3211-3221 (author version).
Islam, et al., "A General Approach for High Yield Fabrication of CMOS-Compatible All-Semiconducting Carbon Nanotube Field Effect Transistors," NanoTech (2012) doi:10-1088/0957-4484/23/12/125201.
Jia, et al., "Covalently Bonded Single-Molecule Junctions with Stable and Reversible Photoswitched Conductivity," Science (2016) 352(6292):1443-5.

Kaniber, et al., "Covalently Binding the Photosystem I to Carbon Nanotubes," PACS: 81.07.Nb, 85.65.+h, 81.07.De.
Kim, et al., "Protein Conjugation with Genetically Encoded Unnatural Amino Acids," Curr Opin Chem Biol. (2013) 17(3):412-419.
Kormondy, et al., "High Yield Assembly and Electron Transport Investigation of Semiconducting-Rich Local-Gated Single-Walled Carbon Nanotube Field Effect Transistors," Nanotechnology (2011) doi:10.1088/0957-4484/22/41/415201.
Kumar, et al., "PEG-labeled Nucleotides and Nanopore Detection for Single Molecule DNA Sequencing by Synthesis," Scientific Reports (2012) 2(684):1-8.
Kuzmany, et al., "Functionalization of Carbon Nanotubes," Synthetic Metals (2004) 141: 113-122.
Lawrence, et al., "Supercharging Proteins Can Impact Unusual Resilience," J. Am. Chem. Soc. (2007) 129(33): 10110.doi:10.1021/ja071641y.
Lerner et al., "Toward Quantifying the Electrostatic Transduction Mechanism in Carbon Nanotube Molecular Sensors," JACS (2012) 134:14318-21.
Levene et al., "Zero-mode Waveguides for Single-molecule Analysis at High Concentration" Science (2003) 299:682-686.
Li, et al., "Advanced Fabrication of Si Nanowire FET Structures by Means of a Parallel Approach," NanoTech (2014) doi:10.1088/0957-4484/25/27/275302.
Li, et al., "Direct Real-Time Detection of Single Proteins Using Silicon Nanowire-Based Electrical Circuits," Nanoscale (2016) 8:16172-6.
Liu, et al., "Single-Molecule Detection of Proteins Using Aptamer-Functionalized Molecular Electronic Devices," Angew. Chem. Int. (2011) 50:2496-2502.
Lu, et al., "Label-Free and Rapid Electrical Detection of hTSH with CMOS-Compatible Silicon Nanowire Transistor Arrays," Applied Materials & Interfaces (2014) 6:20378-20384.
Luong, et al.,"Purification, Functionalization, and Bioconjugation of Carbon Nanotubes," Bioconjugation Protocols: Strategies and Methods, Methods in Molecular Biology, vol. 751, DOI 10.1007/978-1-61779-151-2_32.
Olsen, et al., "Electronic Measurements of Single-Molecule Processing by DNA Plymerase I (Klenow Fragment)," J Am Chem Soc (2013) 135(21):7855-60.
Park, et al., "Array-Based Electrical Detection of DNA with Nanoparticle Probes," Science (2002) 295:1503-1506.
Patolsky, et al., "Detection, Stimulation and Inhibition of Neuronal Signals with High-Density Nanowire Transistor Arrays," Science (2006) 313:1100-4.
Patolsky, et al., "Electrical Detection of Single Viruses," PNAS (2004) 101(39):14017-14022.
Phillip, et al., "Common Crowding Agents Have Only a Small Effect on Protein-Protein Interactions," Biophysical Journal (2009) 97:875-85.
Pugliese, et al., "Processive Incorporation of Deoxynucleoside Triphosphate Analogs by Single-Molecule DNA Polymerase I (Klenow Fragment) Nanocircuits," JACS (2015) 137:9587-94.
Qi, et al., "The Effect of Macromolecular Crowding on the Electrostatic Component of Barnase-Barstar Binding: A Computational, Implicit Solven-Based Study," PLOS ONE (2014) 9(6):e98618.
Ringler and Schulz, "Self-Assembly of Proteins into Designed Networks," Science (2003) 302:106-109.
Russell and Claridge, "Peptide Interfaces with Graphene: An Merging Intersection of Analytical Chemistry, Theory and Materials," Anal. Bioanal. Chem (2016) 408:2649-2658.
Sattely, et al., "Total Biosynthesis: In Vitro Reconstitution of Polyketide and Nonribosomal Peptide Pathways," Natural Product Reports (2008) 25:757-793.
Schechter, et al., "Renal Accumulation of Streptavidin: Potential Use for Targeted Therapy to the Kidney," Kidney International (1995) 47:1327-1335.
Schoene, et al., "SpyTag/SpyCatcher Cyclization Confers Resilience to Boiling on a Mesophilic Enzyme," Agnew. Chem. Int. Ed. (2014) 53: 1-5.
Setiadi, et al., "Room-Temperature Discrete-Charge-Fluctuation Dynmaics of a Single Molecule Adsorbed on a Carbon Nanotube," Nanoscale (2017) 9:10674-83.

(56) References Cited

OTHER PUBLICATIONS

Shimoboji, et al., "Mechanistic Investigation of Smart Polymer-Protein Conjugates," Bioconjugate Chemistry (2001) 12:314-319.
Shoorideh, et al., "On the Origin of Enhanced Sensitivity in Nanoscale FET-Based Biosensors," PNAS (2014) 111(14):5111-6.
Sorgenfrei, et al., "Debye Screening in Single-Molecule Carbon Nanotube Field-Effect Sensors," Nano Letters (2011) 11:3739-43.
Sorgenfrei, et al., "Label-Free Single-Molecule Detection of DNA-Hybridization Kinetics with a Carbon Nanotube Field-Effect Transistor," Nature Nanotechnology (2011) 6:126-132.
Stern, et al., "Importance of the Debye Screening Length on Nanowire Filed Effect Transistor Sensors," Nano Letters (2007) 7(11):3405-3409.
Tahiri-Alaoui, et al., "High Affinity Nucleic Acid Aptamers for Streptavidin Incorporated into Bi-Specific Capture Ligands," Nuc. Ac. Res (2002) 30(10):e45.
Takakura, et al., "Tamavidins—Novel Avidin-Like Biotin-Binding Proteins from the Tamogitake Mushroom," FEBS Journal (2009) 276(5):1383-97.
Thompson, et al., "Engineering and Identifying Supercharged Proteins for Macromolecule Delivery into Mammalian Cells," Methods in Enzymology (2012) 503:293-318.
Tian, et al., "Three-Dimensional, Flexible Nanoscale Field Effect Transistors as Localized Bioprobes," Science (2010) 329(5993): 830-834.
Timko, et al., "Response to Comment on 'Detection, Stimulation, and Inhibition of Neuronal Signals with High-Density Nanowire Transistor Arrays'," Science (2009) 323:1429c.
University of Illinois, Grant Report dated Dec. 1, 2006 for Grant No. FA9550-04-1-0214, titled, "Single Molecule Detection Using a Silicon Nanopore-Nanotransistor Integrated Circuit."
Vernicks, et al., "Electostatic Melting in a Single-Molecule Field-Effect Transistor with Applications in Genomic Identification," Nature Commun (2017) 8:15450.
Wang, et al., "Point Decoration of Silicon Nanowires: An Approach Toward Silicon-Molecule Electrical Detection," Angew Chem. Int. (2014) 53:5038-43.
Wang, et al., "Selective Fabrication of Quasi-Parallel Single-Walled Carbon Nanotubes on Silicon Substrates," NanoTechnology (2010) doi:10.1088/0957-4484/21/39/395602.
Wei, et al., "Bacterial Virulence Proteins as Tools to Rewire Kinase Pathways in Yeast and Immune Cells," Nature (2012) 488:384-388.
Wilbur et al., "Design and Synthesis of Bis-Biotin-Containing Reagents for Applications Utilizing Monoclonal Antibody-Based Pretargeting Systems and Streptavidin Mutants," Bioconjugate Chem. 21(7):1225-1238.
Wilbur, et al., "Biotin Reagents for Antibody Pretargeting. 2. Synthesis and in Vitro Evaluation of Biotin Dimers and Trimers for Cross-Linking of Streptavidin," Bioconjugate Chemistry (1997) 8(6):819-32.
Wilbur, et al., "Biotin Reagents for Antibody Pretargeting. 3. Synthesis, Radioiodination, and Evaluation of Biotinylated Starburst Dendrimers," Bioconjugate Chemistry (1998) 9:813-825.

Wilson, et al., "The Use of mRNA Display to Select High-Affinity Protein-Binding Peptides," Proc. Natl. Acad. Sci. USA (2001) 98:3750-3755.
Xia, et al., "Quantifying the Kinetic Stability of Hyperstable Proteins via Time Dependent SDS Trapping," Biochemistry (2012) 51:100-107.
York, et al., "Particle Detection Using an Integrated Capacitance Sensor," Sensors and Actuators (2001) 92:74-79.
You, et al., "Real-Time Monitoring of Conformational Transitions of Single-Molecule Histone Deacetylase 8 with Nanocircuits," Chem Common. (2017) 53:3307-10.
Zakeri, et al., "Peptide Tag Forming A Rapid Covalent Bond To a Protein, Through Engineering a Bacterial Adhesin," PNAS (2012) 109(12):E690-7.
Zareh, et al., "Single-Molecule Imaging of Protein Adsorption Mechanisms to Surfaces," Microscopy Research and Technique (2011) 74:682-687.
Zhang and Lieber, "Nano-Bioelectronics," Chemical Reviews (2015) DOI: 10.1021/acs.chemrev.5b00608.
Zhang, et al., "Controlling Macromolecular Topology with Genetically Encoded SpyTag-SpyCatcher Chemistry," J. Am. Chem. Soc. (2013) 135: 13988-13997.
Zhang, et al., "Effect of Chemical Oxidation on the Structure of Single-Walled Carbon Nanotubes," J. Phys. Chem. B (2003) 107:3712-3718.
Zhu, et al., "Electrical-Impedance-Spectroscopy Characterization of Individually Immobilized Single Particles and Yeast Cells," 16th International Conference on Miniaturized Systems for Chemistry and Life Sciences (Oct. 28-Nov. 1, 2012) Okinawa, Japan, p. 995-997.
International Search Report and Written Opinion dated Sep. 2, 2014 for related case PCT/US2014/036843.
International Preliminary Report on Patentability dated Nov. 19, 2015 for related case PCT/US2014/036843.
International Search Report and Written Opinion dated Nov. 10, 2016 for related case PCT/US2016/045381.
Supplementary Search Report dated Jan. 4, 2017 for related case EP 14794438.3.
International Preliminary Report on Patentability dated Feb. 15, 2018 for related case PCT/US2016/045381.
Noor et al., "Silicon Nanowires as Filed-Effect Transducers for Biosensor Development: A Review," Analytics Chimica Acta (2014) 825:1-25.
Padeste et al., "Molecular Assembly of Redox-Conductive Ferrocene-Streptavidin Conugates—Towards Bio-Electrochemical Devices," Biosensors and Bioelectronics (2004) 20:545-552.
First Exam Report dated May 2, 2018 for related case EP 14794438.3.
First Exam Report dated Sep. 12, 2018 for related case CN 201480038761.4.
EP Search Report dated Nov. 5, 2019 for related case EP 19184152.7.
Second Exam Report dated May 30, 2019 for related case CN 201480038761.4.
EP Search Report dated Feb. 4, 2019 for related case EP 16833817.6.

\* cited by examiner

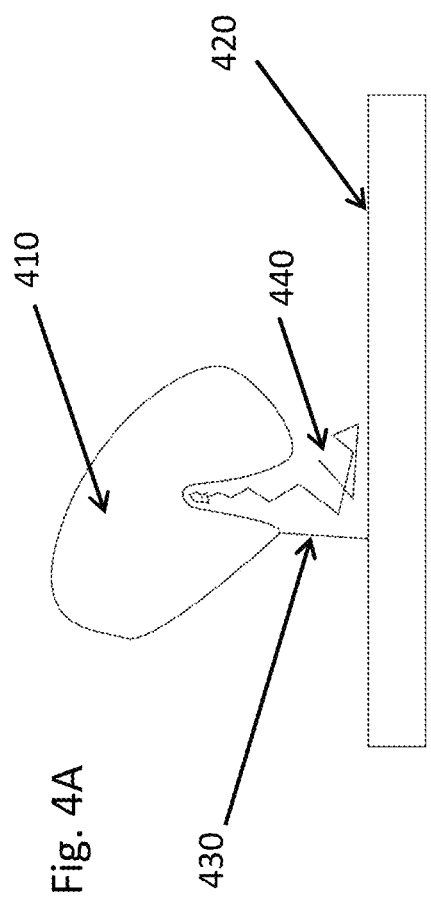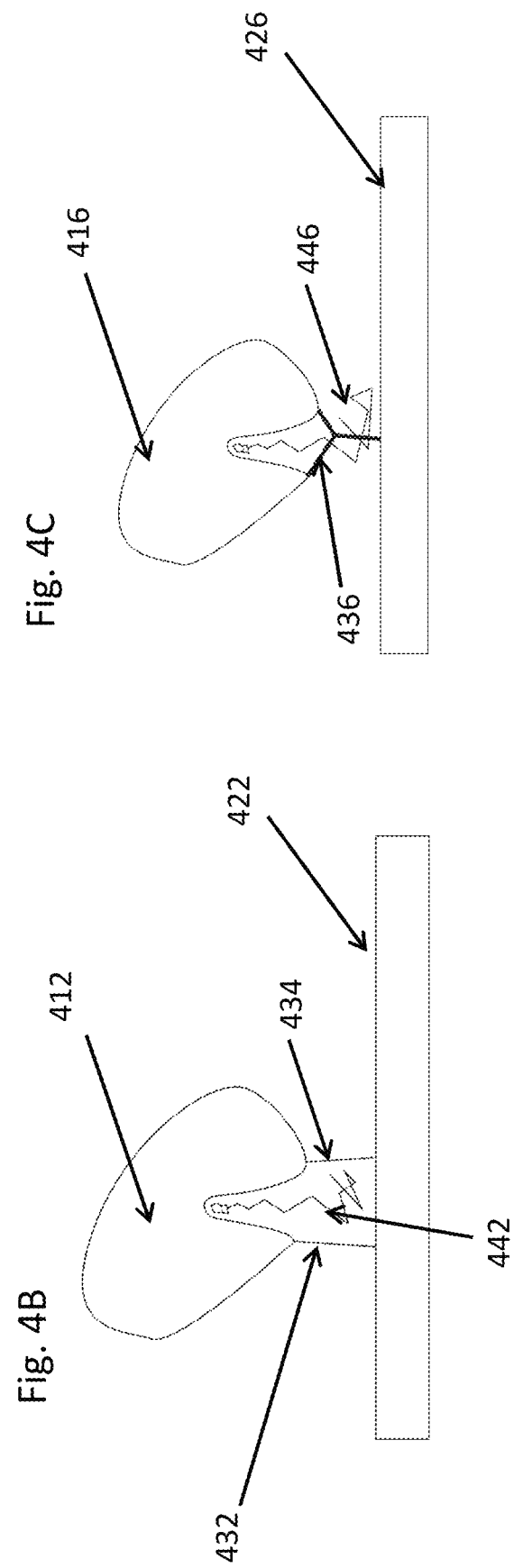

SINGLE-MOLECULE NANOFET SEQUENCING SYSTEMS AND METHODS

CROSS-REFERENCE TO RELATED APPLICATIONS

This application is a continuation of U.S. patent application Ser. No. 15/227,661, filed Aug. 3, 2016, which claims the benefit of U.S. Provisional Application Nos. 62/201,731, filed on Aug. 6, 2015, and 62/239,176, filed on Oct. 8, 2015, the disclosures of which are each incorporated herein by reference in their entireties.

STATEMENT REGARDING FEDERALLY SPONSORED RESEARCH

Not Applicable.

BACKGROUND OF THE INVENTION

Nucleic acid sequence data is valuable in myriad applications in biological research and molecular medicine, including determining the hereditary factors in disease, in developing new methods to detect disease and guide therapy (van de Vijver et al. (2002) "A gene-expression signature as a predictor of survival in breast cancer," New England Journal of Medicine 347: 1999-2009), and in providing a rational basis for personalized medicine. Obtaining and verifying sequence data for use in such analyses has made it necessary for sequencing technologies to undergo advancements to expand throughput, lower reagent and labor costs, and improve accuracy (See, e.g., Chan, et al. (2005) "Advances in Sequencing Technology" (Review) Mutation Research 573: 13-40 which is incorporated herein in its entireties for all purposes.

Various methods of sequencing are used and each has its strengths and weaknesses. Single molecule real time sequencing has advantages over other sequencing methodologies including the ability to provide longer read lengths. Many current methods of sequencing use optical labels. There is a need for improved sequencing instruments and methods that use non-optical readouts, and in particular real time single molecule sequencing methods with these characteristics.

Electronic detection of single molecules and single particles, including by capacitive, impedance, and conductive methods has been demonstrated. The current invention provides instruments, devices and methods for non-optical real-time single molecule sequencing and for real time non-optical detection of biomolecules.

BRIEF SUMMARY OF THE INVENTION

In some aspects, the invention provides a method for nucleic acid sequencing comprising: providing a substrate comprising an array of nanoscale field effect transistors (nanoFETs) capable of measuring electrical changes due to molecular interactions, wherein a plurality of the nanoFETs have a single polymerase enzyme complex.

In some aspects, the invention provides methods for nucleic acid sequencing comprising: providing a substrate comprising an array of nanoFETs, each comprising a source, a drain, and a gate, wherein a plurality of the nanoFETs comprise a single polymerase enzyme complex comprising a polymerase enzyme and a template nucleic acid, the complex attached to gate of the nanoFET, wherein the polymerase enzyme is attached to the gate in an orientation whereby the nucleotide exit region of the polymerase enzyme is toward the gate of the nanoFET; exposing the substrate to a plurality of types of nucleotide analogs, each comprising a different conductivity label attached to the phosphate portion of the nucleotide analog through a linker under conditions whereby polymerase mediated nucleic acid synthesis occurs, resulting in cleavage of the conductivity label and the growth of a nascent nucleic acid strand; applying a voltage between the source and drain, whereby when a nucleotide analog resides in the active site of the enzyme, the conductivity label on the nucleotide analog produces a measurable change in the electrical signal at the gate; monitoring an electrical signal at the gate over time, whereby the electrical signal indicates an incorporation event for a type of nucleotide analog having a specific conductivity label; and using the electrical signal to determine a sequence of the template nucleic acid.

In some embodiments the electrical signal used to determine the sequence of the template nucleic acids includes the duration of the signal indicating the residence time of a nucleotide analog in the active site of a polymerase. In some embodiments the gate of each nanoFET comprises a nanowire. In some embodiments the gate of each nanoFET comprises a carbon nanotube. In some embodiments the voltage across the source and drain is DC. In some embodiments the voltage across the source and drain is AC, and the frequency of the AC voltage is changed with time.

In some embodiments the substrate is exposed to four types of nucleotide analogs corresponding to A, G, C, T, or A, G, C, U, each of the four types of nucleotide analogs having a different conductivity label. In some embodiments the conductivity label comprises a protein. In some embodiments the protein has a molecular weight that is between 1/10 and 3 times the molecular weight of the polymerase enzyme. In some embodiments the protein has a molecular weight that is between 1/10 and 3 times the molecular weight of a phi29 polymerase.

In some embodiments the polymerase is attached through a linker at a single point on the polymerase that is within 50 angstroms of the nucleotide exit region of the enzyme. In some embodiments the polymerase is a phi29-type polymerase and the polymerase is attached through a linker at a single point on the polymerase that is within 5 amino acids from position 375 or position 512. In some embodiments the polymerase is modified phi29 polymerase.

In some embodiments the polymerase is attached through two linkers at two different positions on the polymerase, wherein at least one is attached to a position that is within 50 angstroms of the nucleotide exit region of the enzyme. In some embodiments the polymerase is attached through two linkers at two different positions on the polymerase, wherein both linkers are attached to positions that are within 50 angstroms of the nucleotide exit region of the enzyme. In some embodiments the polymerase is attached through an trivalent linker that attaches to the polymerase at two different positions that are within 50 angstroms of the nucleotide exit region of the enzyme, and the trivalent linker is attached to a single point on the gate of the nanoFET.

In some embodiments at least one of the conductivity labels comprises a polymer chain having multiple charges. In some embodiments there are 4 types of nucleotide analogs and each comprises a conductivity label comprising a polymer chain having multiple charges. In some embodiments there are 4 types of nucleotide analogs and each comprises a conductivity label having a different number of negative charges. In some embodiments there are 4 types of nucleotide analogs and each comprises a conductivity label having a different number of positive charges. In some embodiments there are 4 types of nucleotide analogs and each comprises a conductivity label having both negative and positive charges and each has a different net charge. In some embodiments there are 4 types of nucleotide analogs and two labels have a net negative charge, and two labels have a net positive charge.

In some embodiments there are 4 types of nucleotide analogs and two of the labels result in an increase in conductivity at the gate when their corresponding nucleotide analog is associated with the polymerase, and two of the labels result in an decrease in conductivity at the gate when their corresponding nucleotide analog is associated with the polymerase In some aspects the invention provides a chip for sequencing a plurality of single nucleic acid template molecules comprising: a substrate comprising; a plurality of nanoFET devices, each nanoFET device comprising a source, a drain and a gate and a single polymerase enzyme complex bound to the gate of the nanoFET, wherein the polymerase enzyme complex comprises a polymerase enzyme and a template nucleic acid, wherein the polymerase enzyme is attached to the gate in an orientation whereby the nucleotide exit region of the polymerase enzyme is toward the gate of the nanoFET; wherein the substrate is configured such that the nanoFET device comes into contact with a sequencing reaction mixture comprising a plurality of types of nucleotide analogs each having different conductivity labels; and a plurality of electrical connection sites for bringing current and voltage to the the nanoFETs, and for receiving electrical signals from the nanoFETs.

In some embodiments the gate of each nanoFET comprises a nanowire. In some embodiments the gate of each nanoFET comprises a carbon nanotube. In some embodiments the substrate comprises greater than 1,000 nanoFET devices. In some embodiments the substrate comprises greater than 10,000 nanoFET devices. In some embodiments the substrate comprises about 1,000 nanoFET devices to about 10 million nanoFET devices. In some embodiments the substrate comprises about 10,000 nanoFET devices to about 1 million nanoFET devices.

In some embodiments the substrate comprises electronic elements for one or more of: providing electrical signals to the nanoFETs, measuring the electrical signals at the nanoFETs, analog to digital conversion, signal processing, and data storage. In some embodiments the electrical elements are CMOS elements. In some embodiments the polymerase is attached through a linker at a single point on the polymerase that is within 50 angstroms of the nucleotide exit region of the enzyme. In some embodiments the polymerase is a phi29-type polymerase and the polymerase is attached through a linker at a single point on the polymerase that is within 5 amino acids from position 375 or position 512. In some embodiments the polymerase is modified phi29 polymerase.

In some embodiments the polymerase is attached through two linkers at two different positions on the polymerase, wherein at least one is attached to a position that is within 50 angstroms of the nucleotide exit region of the enzyme. In some embodiments the polymerase is attached through two linkers at two different positions on the polymerase, wherein both linkers are attached to positions that are within 50 angstroms of the nucleotide exit region of the enzyme.

In some embodiments the polymerase is attached through a trivalent linker that attaches to the polymerase at two different positions that are within 50 angstroms of the nucleotide exit region of the enzyme, and the trivalent linker is attached to a single point on the gate of the nanoFET.

In some aspects, the invention provides a system for sequencing template nucleic acids comprising: a housing having housing electrical connection sites; a chip that reversibly mates with the housing comprising a substrate comprising; chip electrical connection sites that reversibly connect to the housing electrical connection sites; a plurality of nanoFET devices, each nanoFET device comprising a source, a drain, and a gate, and a single polymerase enzyme complex bound to the gate, wherein the polymerase enzyme complex comprises a polymerase enzyme and a template nucleic acid, wherein the polymerase enzyme is attached to the gate in an orientation whereby the nucleotide exit region of the polymerase enzyme is toward the gate of the nanoFET; a fluid reservoir for contacting a sequencing reaction mixture with the nanoFET devices, the sequencing reaction mixture comprising a plurality of types of nucleotide analogs, each having a different conductivity label, wherein the conductivity labels are sensed by the nanoFET while an analog is associated with the polymerase enzyme complex; an electronic control system electrically connected to the nanoFET devices through the electrical connections to apply desired electrical signals to the nanoFET and for receiving electrical signals from the nanoFET devices; and a computer that receives information on the electrical signals at the nanoFET over time and uses such information to identify a sequence of the template nucleic acid.

In some embodiments the gate of each nanoFET comprises a nanowire. In some embodiments the gate of each nanoFET comprises doped silicon. In some embodiments the substrate comprises greater than 1,000 nanoFET devices. In some embodiments the substrate comprises greater than 10,000 nanoFET devices. In some embodiments the substrate comprises about 1,000 nanoFET devices to about 10 million nanoFET devices. In some embodiments the substrate comprises about 10,000 nanoFET devices to about 1 million nanoFET devices.

In some embodiments the substrate comprises electronic elements for one or more of: providing electrical signals to the nanoFET devices, measuring the electrical signals at the nanoFET devices, analog to digital conversion, signal processing, and data storage. In some embodiments the electrical elements are CMOS elements.

In some aspects the invention provides methods of producing an array carbon nanotube nanoFETs comprising: providing a substrate having an array of sets of nanoscale electrodes, each set of nanoscale electrodes having four nanoscale electrodes in a line, the four electrodes comprising two outer electrodes and two inner electrodes; exposing the substrate to a solution of carbon nanotubes; and applying a voltage across the outer electrodes for each set whereby carbon nanotubes are deposited across the set of nanoscale electrodes, thereby producing an array of carbon nanotube nanoFETs each having a source and drain provided by the inner electrodes.

In some embodiments the methods further comprise a step of selectively depositing a conductive material onto the inner source and drain electrodes. In some cases the selective deposition is carried out by electrodeposition from solution.

In some embodiments the methods further comprise a step of cleaving the nanotube between the inner and outer electrodes.

BRIEF DESCRIPTION OF THE DRAWINGS

FIG. 1A, FIG. 1B, and FIG. 1C show various stages of the sequencing reaction

FIG. 4A show a single point of attachment near the nucleotide exit region to a nanowire. FIG. 4B shows multiple attachments from the polymerase to a nanowire. FIG. 4C shows a trivalent linker that multiply attaches to the polymerase and makes a single attachment to the nanowire.

DETAILED DESCRIPTION OF THE INVENTION

Figure 1:
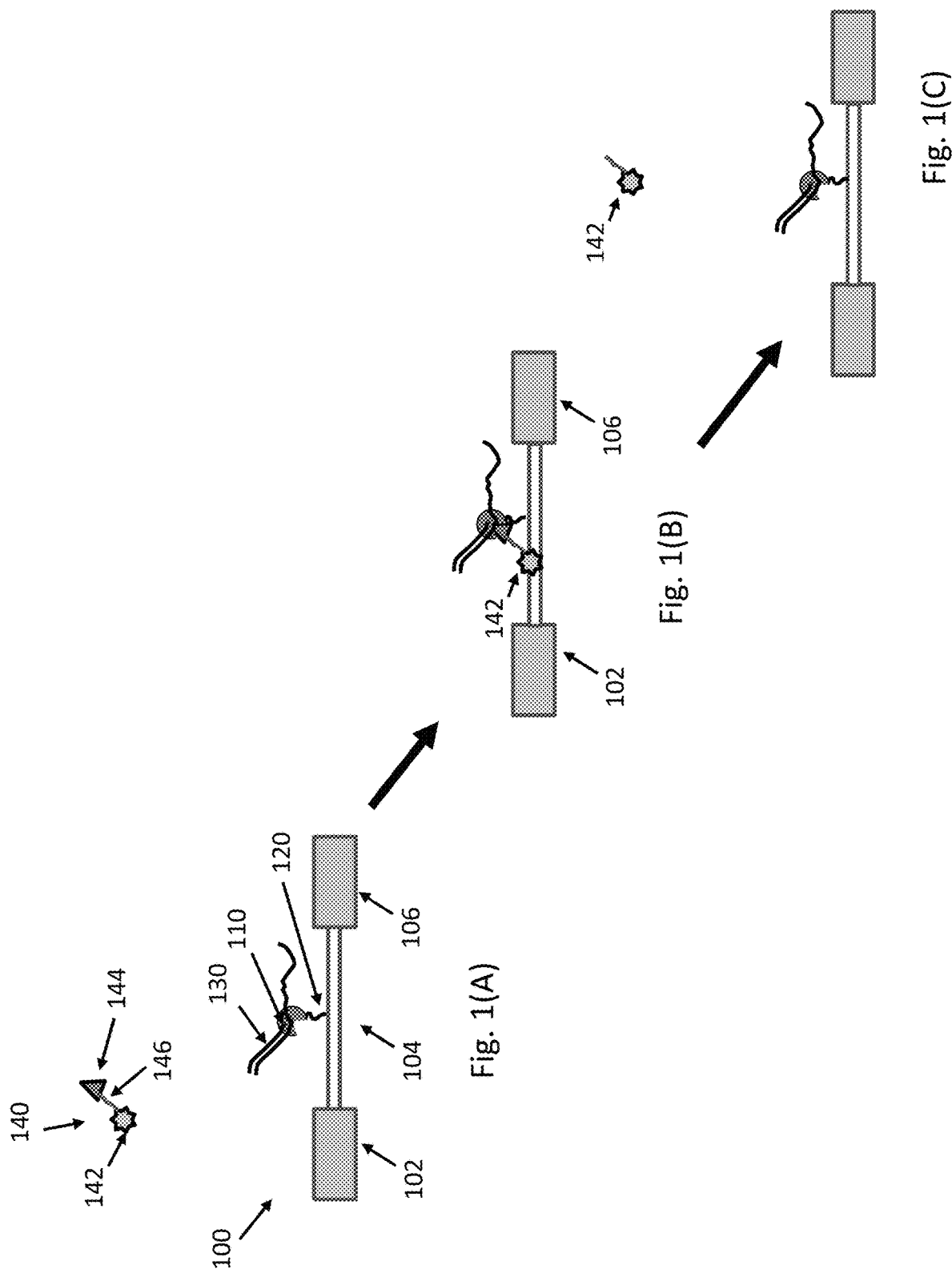
FIGS. 1A-1C illustrate a method of the invention for sequencing using a nanoFET.

In some aspects, the invention provides methods, devices, systems, and compositions of matter directed to single-molecule real-time electronic sequencing. The electronic detection can performed using with a nanoscale field effect transistor (nanoFETs), wherein the nanoFETs is sensitive to molecular interactions in the vicinity of the gate of the nanoFETs. In some aspects a single polymerase-template complex is immobilized on or proximate to a the gate of a nanoFET device, and the electrical signal from the nanoFET is used for determining a nucleic acid sequence. The nanoFETs of the invention typically have a nanoscale gate that comprises a nanowire such a carbon nanotube. In some aspects the invention provides devices and methods for making and using nanoFET devices for single molecule real-time analysis of biomolecules.

Where single molecule nanoFET sequencing is employed, typically four nucleotide analogs, each having a different distinguishable conductivity label, are present in a sequencing reaction mixture. The term conductivity label is used to designate a label that will produce a change in the electrical signal at a nanoFET. In some cases, this change in electrical signal is due to a change in the conductivity of the gate of the nanoFET, but the change in electrical signal can include other aspects as described in more detail below. The conductivity label is typically connected to the nucleotide analog through the phosphate portion of the nucleotide analog such that when the nucleotide analog is incorporated by the polymerase enzyme into a growing nascent nucleic acid strand, the label is released. The conductivity label is typically connected to the nucleotide portion of the analog through a linker. When the nucleotide analog is held in the polymerase enzyme active site during the incorporation reaction, the conductivity label produces a change in conductivity of the gate of the nanoFET. The change in electrical signal such as gate conductivity can be used to determine the presence and the identity of the nucleotide analog that is in the active site of the polymerase enzyme. The characteristics of the gate conductivity while the nucleotide is in the active site will be different than the characteristics of a nucleotide that freely diffuses near the electrode. Because the nucleotide is held close to the gate of the nanoFET during the incorporation process by the enzyme, it is held in place long enough for its characteristic conductivity change at the gate to be determined to measure the presence of the nucleotide and also to identify which type of nucleotide is being incorporated.

In some cases, a fixed voltage is applied across the source and drain electrodes, and the level of conductivity through the gate between the electrodes is monitored over time. In some cases, gate conductivity is monitored while an AC current is applied to the electrode. The frequency of the current applied to the nanoFET can be varied over time in a manner that allows for the identification of the nucleotide analog in the active site, for example having gate electrical signal versus frequency characteristics. Base calling software is then employed to call bases by correlating the gate conductivity over time at the relevant voltage with the expected characteristics of the labels. The called bases can be used to identify the sequence of the template nucleic acid whose sequence is complementary to that of the added bases. The methods of the invention utilize the characteristic that a nucleotide analog which is incorporated into a growing nucleic acid chain spends more time in the active site of the enzyme and therefore spends more time proximate to the gate of the nanoFET than do non-cognate nucleotides that are not incorporated or freely diffusing nucleotides passing near the electrode. Thus, the residence time of the labeled nucleotide in the active site of the enzyme can be used as a characteristic to distinguish incorporated nucleotides from freely diffusing nucleotides in solution.

Chips having arrays of nanoscale electronic elements having nanoFET devices are described. Each nanoFET device performs a sequencing reaction in real time, allowing for hundreds, thousands, millions, tens of millions or more sequencing reactions to be monitored simultaneously. The nanoscale elements used in devices, such as the source, gate, and drain, are typically constructed to have a small size, and therefore to have low levels of capacitance noise. This allows for rapid transfer of current for electronic measurements of events which typically occur on the microsecond to millisecond timescale. The chips can be prepared using known semiconductor processing techniques, for example on a silicon substrate. The nanoFETs in the array have a polymerase enzyme-template complex attached to the gates of the nanoFETs or attached proximate to the gates.

Systems for carrying out sequencing are described. The nanoFET sequencing chips of the invention typically mate with a socket that holds the chip in place and provides electrical connections to interconnects on the chips for transferring electrical signals to and from the nanoFETs. A current/voltage source provides the current and voltage to bring the nanoFETs to the desired potential and in some cases to apply the desired AC frequencies as a function of time. A nanoFET is used to determine the electrical signal changes associated with the presence of the conductivity labels.

The system includes a fluid reservoir for holding the sequencing reagents in contact with the nanoFET on the chip. The fluid reservoir can be, for example, a microfluidic chamber or a well. The system can also have either a counter electrode, a reference electrode or both in contact with the fluid. The counter electrode and or the reference electrode can be incorporated into the chip or can be separate from the chip, and in contact with the liquid sample. In the fluid reservoir is a sequencing reaction mixture that allows a single polymerase enzyme proximate to the nanoFETs to perform nucleic acid synthesis. The sequencing reaction mixture has nucleotide analogs with conductivity labels that are cleaved when the nucleotide is incorporated into the growing nucleic acid strand. The enzyme is proximate to the gates such that when a nucleotide analog is associated with the polymerase enzyme on its way to incorporation into the growing chain, the conductivity label on the nucleotide analog changes the electrical characteristics such as conductivity at the gate. A voltage/current source can be used to vary an AC signal at the nanoFETs over time. A current meter can be used to measure the level of current flow and other characteristics such as impedance. The measurement of a change in electrical characteristics at the nanoFET gate indicates the presence of a conductivity label on the nucleotide analog held within the enzyme. A computer changes in signal at the nanoFETs, and uses this information to determine the sequence of nucleotide incorporation. The conductivity signal indicates that the nucleotide corresponding to that label is being incorporated into the growing strand. By measuring a time sequence of incorporation, the sequence of the growing strand, and thereby the sequence of the corresponding template nucleic acid, is ascertained.

One aspect of the invention provides for real-time sequencing in which the incorporation of nucleotides into the growing strand is detected using a field effect transistor, e.g., FET devices, nanoscale field effect transistors (nanoFETs), nanowire FET devices, carbon nanotubes/nanowires, single-walled carbon nanotube (SWNT) FETs, and other conductive nanowires, e.g., conductive silicon nanowires. As such, although certain specific embodiments herein describe features of the invention with reference to nanowires or nanotubes, it will be understood that the invention is not limited to the use of nanowires or nanotubes and can employ other FET devices, such as those listed above. It will be understood in this context that the terms "nanowire" and "nanotube" is meant to encompass all of the concepts involving FET devices and in particular carbon nanotubes, as well as any other FET device with a spatially restricted gate. The incorporation can be detected, for example, by changes in the conductivity of the gate of the nanoFET. Thus, where the application refers to the gate of a FET devices it is to be understood that the gate can be a nanowire or carbon nanotube. In some cases, the FET comprises a nanowire, and incorporation is detected by detecting changes in conductance of a nanowire. Although various embodiments described herein comprise polymerase enzymes performing nucleobase incorporation, the invention is not limited to only those embodiments and can also or alternatively comprise other types of nucleic acid processing enzymes, e.g., helicases, ligases, topoisomerases, nucleases, and the like, where interaction of the nucleic acid processing enzyme with a nucleic acid results in a detectable change in conductance, whether or not nucleobase incorporation is occurring. These changes are detected as signals that measure some aspect of the interaction between the enzyme and the nucleic acid, e.g., informing about the components or progress of a biochemical reaction between them. Thus, in the specification, where a polymerase enzyme is described as being attached to a nanoFET, it is to be understood that this description also applies to any suitable biomolecule, and where conductivity labels are described as being used to measure polymerase enzyme activity, it is understood that this description will apply to measuring the activity of biomolecules other than polymerase enzymes, including measuring the behavior and activity of other suitable enzymes.

In certain embodiments, a polymerase enzyme complex including a polymerase enzyme and a template nucleic acid is immobilized onto the nanowire or proximal to the nanowire. The polymerase enzyme complex is exposed to a reaction mixture that supports nucleic acid synthesis. The reaction mixture includes nucleotides or nucleotide analogs in which at least one of the types of nucleotide analog has a label that will be referred to herein as a conductance label (which can also be referred to as a conductivity label or as a conductance-modulating label). In some cases the conductance or conductivity label is a charge label. In certain embodiments, the label is connected to the polyphosphate portion of the nucleotide analog such that when the nucleotide analog is incorporated, the label is released as the polyphosphate chain is cleaved. In other embodiments, the label is a characteristic of the nucleotide analog that is absent from a canonical nucleotide, e.g., a base modification or extended polyphosphate tail that does not prevent incorporation into a nascent strand by a polymerase enzyme. In other embodiments, the label is a chemical moiety that has been attached to the nucleobase or the sugar ring. In alternative embodiments, the conductance label is a natural part of a nucleotide, e.g., the naturally occurring triphosphate of a nucleotide could produce the electric field detected by the FET device. In some embodiments, all the nucleotides in a reaction mixture are natural and the identity of the bases is derived from differences in the electrical signal that result from base-dependent position changes of the nucleobase, the sugar ring, and/or the phosphate groups. In other embodiments, a subset of the nucleotides would be natural and the rest would be analogs containing different number of phosphates or terminal phosphate labels as described above.

Where the conductance-modulating label is linked to a phosphate group other than the alpha phosphate or when the conductance-modulating label comprises the beta phosphate the incorporation of the nucleotide analog results in the release of the conductance label, restoring the conductivity of the nanowire to a value that is not impacted by the presence of the label, e.g., a baseline value. It is contemplated in the present invention that the baseline value may be impacted by the primary structure of the nucleic acid template and/or different conformational states of the enzyme, and baseline correction for sequence content is an aspect of the invention. While each of the four types of nucleotides may sample the active site, the nucleotide or nucleotide analog that is incorporated (a cognate nucleotide) will spend a longer time in the active site than a nucleotide or nucleotide analog that is not incorporated. Thus, the conductivity of the nanowire detects when a labeled nucleotide analog is present in the active site of the polymerase enzyme.

The invention provides for real time sequencing in which the incorporation of nucleotides into the growing strand is detected using a nanoscale field effect transistor (nanoFET). The incorporation can be detected, for example, by changes in the conductivity of the gate of the nanoFET. The characteristics of the conductance change in the nanowire can be different for different conductance labels. Thus, in addition to detecting the presence of an incorporated nucleotide, the methods of the invention allow for discriminating between two or more nucleotide analogs in the reaction mixture. Typically four types of nucleotide analogs are used, corresponding to A, G, T, and C for DNA and to A, G, U, and C for RNA, each having a different conductance label. By observing the incorporation of nucleotides over time, the sequence of the template nucleic acid in the polymerase enzyme complex can be determined. The polymerase specifically adds a nucleotide to the growing strand that is complementary to the nucleotide in the template strand, e.g. A<->T, and G<->C. By determining which nucleotides have been added to the growing strand, the sequence of the template strand can be determined.

A nanowire can be used as the gate in the nanoFET, with electrodes attached to either side of the nanowire acting as the source and the drain. The nanowire can be, for example, a carbon nanotube or a semiconductor such as doped silicon. There are many materials that can make up the nanowire or gate, examples of which are described in more detail below.

In some cases the nanowire or nanoFET are used to perform nucleic acid sequencing by measuring the presence of the labeled nucleotide analog within the enzyme complex as the enzyme adds nucleotides to a growing strand in real time. FIGS. 1A-1C provides a schematic representation of a method for real time nucleic acid sequencing with two nanoscale electrodes acting as source and drain with a nanowire or gate connecting them. A polymerase-template complex bound proximate to the nanowire or gate. In FIGS. 1A-1C the polymerase enzyme is attached directly to the nanowire. In some cases, rather than being directly attached, the polymerase enzyme is attached to the substrate proximate to the nanowire at a distance such that the presence of a conductivity label attached to a nucleotide analog that is associated with the enzyme is detected by a change in conductance of the nanowire. A substrate 100 has a region on its surface with two electrodes 102 and 106 separated on the order of nanometers to hundreds of nanometers. For example, the separation can be from 1 nm to 400 nm, or from 2 nm to 100 nm. A nanowire 104 extends across the gap, connecting electrodes 102 and 106 (the source and drain of the FET). In some cases, the source and drain are covered with an insulating material such that the source and drain are not in direct contact with the solution. Onto the nanowire or gate 104 is attached a polymerase enzyme complex comprising a polymerase enzyme 110 and a nucleic acid template 130. For the embodiment shown in FIGS. 1A-1C, the enzyme is shown with the nucleotide exit portion of its active site directed toward the nanotube to increase the signal from the labeled nucleotide analog. Approaches for orienting the polymerase enzyme in this way are described herein. While a linear template is shown in FIGS. 1A-1C, other template conformations can be used, e.g., hairpin or circular templates such as those described in U.S. Pat. No. 8,153,375, incorporated herein by reference in its entirety. The complex is attached to the nanowire or gate 104 by an attachment moiety 120. As shown in FIGS. 1A-1C, the polymerase enzyme is attached to the nanowire or nanotube. In some cases, the template nucleic acid can be attached to the nanowire, either directly, or, for example, through hybridization with a primer attached to the nanowire. In some cases, the nanoFETs are disposed horizontally on a surface. In some cases, the electrodes and nanowire are disposed vertically, e.g. as a stack of layers.

The substrate comprising the nanoFETs is contacted with a fluid comprising a sequencing reaction mixture. The sequencing reaction mixture has the reagents required for carrying out polymerase mediated nucleic acid synthesis. The sequencing reaction mixture will generally include divalent catalytic cations such as Mn++ or Mg++ salts for activating the enzyme, as well as other salts such as Na+ or K+ for providing the appropriate ionic strength. Desirable ionic strengths range from 0.01 mM for minimal functioning upwards. Typically, ionic strengths from 50 mM to 500 mM, more preferably from 100 to 400 mM, and even more preferably between 200 and 300 mM can provide for desired levels functioning of the enzyme. In some cases, even concentrations as high as 3 M might be desired to study the behavior of these enzymes at high salt concentration. These salts can also be used to adjust the background capacitance at the electrodes. The ions in the solution are attracted to any charge that might be brought close to the nanowire FET, and these charges, having the opposite charge as the approaching charge, will have the effect of screening or blocking the penetration of the electric field into the solution. The blocking effect by these so-called counter ions can have a characteristic length scale which is very short—just 1 nm at ~150 mM of salt. Because the typical sequencing enzyme might have a dimension of between 5 and 15 nm in diameter, there can be portions of the enzyme that are outside the detection zone of the nanowire detector, thus reducing the power and sensitivity of these methods. As such, various strategies described herein improve the sensitivity of sequencing detection at ionic strengths that might screen the charges that are associated with the presence of a nucleotide, as further described below.

The sequencing reaction mixture also contains conductivity labeled nucleotide analogs such as labeled nucleotide analog 140. In FIGS. 1A-1C, nucleotide analog 140 is a cognate nucleotide having a base that is complementary to the next position in the template nucleic acid 130. The nucleotide analog 140 has a nucleotide portion 144 comprising a nucleobase, a sugar, and a polyphosphate portion. The nucleotide analog 140 has a conductivity label 142 that is attached to the polyphosphate portion of the nucleotide portion 144 through linker 146.

In FIG. 1(B) the nucleotide analog 140 is held in the active site of the polymerase enzyme 110. Due to the orientation of the enzyme relative to the nanotube, the conductivity label is directed toward the nanotube to ensure a robust signal at the nanoFET. Because the nucleotide analog 140 is a cognate nucleotide analog, it is recognized by the enzyme as such, and is held in the enzyme longer than will a non-cognate nucleotide. At the time that the nucleotide analog 140 is associated, its presence is detected by a change in conductivity of the nanowire or gate, resulting in a change in electrical signal, e.g. current and/or voltage at the gate and drain (e.g. electrodes) 102 and 106. Electrodes 102 and 106 are addressed with either direct or alternating current. In some cases, the electrodes are cycled through a series of frequencies, either continuously or in steps. The label 142 causes the characteristics of conductivity or impedance as measured at the electrodes to change, allowing both its presence and its identity to be determined.

When the nucleotide portion of analog 140 is incorporated into the growing strand as shown in FIG. 1(C), the polymerase enzyme cleaves the polyphosphate portion of the nucleotide analog. This cleavage occurs between the alpha and beta phosphates in the polyphosphate portion which releases the portion of the nucleotide analog comprising the label 142, which diffuses away from the substrate. This cleavage and diffusion away of the label ends the period in which the conductance of the nanowire or gate is affected by the presence of the label. The change in conductance, then, provides a measure of the residence time of the nucleotide analog in the active site prior to incorporation, which can be used to determine that nucleotide incorporation has occurred.

The paragraphs above and FIGS. 1A-1C describe the detection of a nucleotide analog. The approach described can also be applied to the measurement of the incorporation of more than one type of analog, for example 2, 3, 4, 5 or more types of analogs. For example, typically four different types nucleotide analogs corresponding to either A, G, C, T, for DNA or A, G, C, U for RNA are used for sequencing. Each of the four types of nucleotide analogs has different and distinguishable conductance characteristics, e.g. four different conductivity labels. The different types of nucleotide analogs can have different magnitudes of conductance change, different current versus time attributes, or can have other distinguishable electrical characteristics such as different current oscillation color or can have any combination of the above characteristics.

Figure 2:
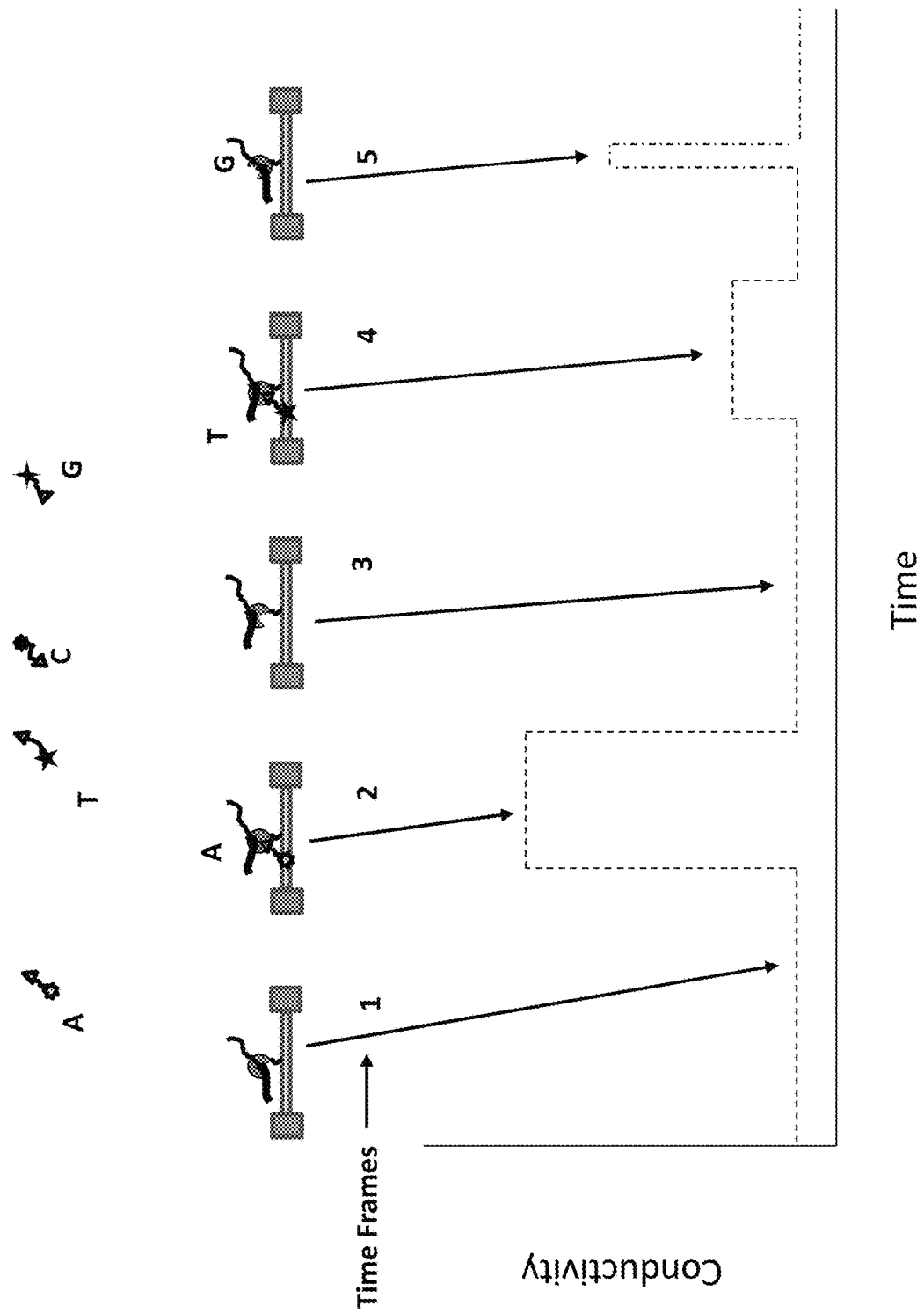
FIG. 2 shows how electrical signal at the gate of the nanoFET can be used to sequence a template nucleic acid.

FIG. 2 shows how the nanowire or gates of the invention can be used to call a series of bases for sequencing. A graph is shown indicating the conductivity signal through the nanowire or gate that is detected. There are four types of nucleotide analogs, each having a different conductivity label, for example, each with a different magnitude of current change in the nanowire or gate when in the vicinity of the nanowire or gate. For example, the voltage across the two electrodes, the source and the drain can be kept constant throughout the experiment, and the current that passes through the nanowire or gate is monitored over time.

The method is described in FIG. 2 by referring to 5 different time frames. During time frame 1, none of the four nucleotide analogs is associated with the polymerase enzyme. In time frame 2, a nucleotide analog corresponding to nucleobase A is in the active site for a time that is characteristic of incorporation (e.g. about 10 msec to about 500 msec). During the time it is in the active site, the measured conductivity rises to a level characteristic of the label on that nucleotide analog. This level of conductivity for a residence time corresponding to incorporation indicates the incorporation of A. When the nucleotide is incorporated, the conductivity label is cleaved and the conductivity signal returns to baseline. In time frame 3, as in time frame 1, no nucleotide analog is in the active site of the polymerase and the conductivity is at a baseline level. During time frame 4, a nucleotide analog corresponding to T is incorporated into the growing strand. The nucleotide analog corresponding to T is held within the active site for a period of time characteristic of incorporation. During the time it is held within the enzyme, a conductivity characteristic of the label on the T nucleotide analog is seen. When the analog is incorporated, the label is cleaved, and diffuses away and the conductivity again returns to baseline. In time frame 5 for a short time, an increase in conductivity (to a level consistent with the label corresponding G) is detected. The time of the increased conductivity is too short to be associated with an incorporation event. This type of feature can be seen, for example, where a non-cognate nucleotide such as G is sampling the active site, after which it diffuses from the enzyme, where the non-cognate nucleotide diffuses near enough to the nanowire to change its conductance, or where the G nucleotide binds non-specifically for a short period of time. During the time of the portion of the experiment shown in FIG. 2, the data indicate that an A and a T were incorporated, which thus indicates that there is a T followed by an A in the template nucleic acid. While this description relates to the incorporation of two nucleotides, this method can be used to sequence long stretches of nucleic acids from hundreds to tens of thousands of bases or more.

The example of FIG. 2 is carried out with four nucleotides, each having a conductivity label that exhibits a different magnitude in conductivity of the nanowire or gate. It will be understood that the same approach described in FIG. 2 can be applied to cases in which conductivity versus time (dielectric spectrum) or current oscillation color (also referred to as noise color, which can be influenced by the type of length and stiffness of the linker attached to the label, the type of conductance label, and the diffusion rate of the label) or any combination of the three is used to identify the incorporated bases.

Thus, the invention, in some aspects provides a method for nucleic acid sequencing that includes providing a substrate comprising an array of nanoFETs. Each nanoFET has a source, a drain, and a gate. The source and drain are typically nanoelectrode, and the gate is typically a nanowire or other nanostructure connecting the source and drain. The gate can be a doped semiconductor such as doped silicon. The gate can be a carbon nanotube, either single walled or multi-walled. The carbon nanotube gate can be modified or doped. A subset of the nanoFETs will have a single polymerase enzyme complex attached to gate of the nanoFET or attached to the substrate proximate to the gate of the nanoFET. Methods are known in the art for creating an attachment site on a nanowire detector such as the ones used by Sorgenfrei, et al. (2011) Nature Nanotechnology 6: 126-132 or by Olsen et al. (2013) J. Am. Chem. Soc. 135(21): 7855-7860, both of which are incorporated herein by reference in their entireties.

Processes for forming nanoFET arrays on CMOS sensors are known in the art, see, for example, U.S. Patent Application No. 2013/0285680, and U.S. Patent Application No. 2015/0093849 which are incorporated by reference herein for all purposes. Such sensors can be formed, for example by transferring nanotubes onto a CMOS integrated circuit (see, Meric et al. "Hybrid carbon nanotube-silicon complementary metal oxide semiconductor circuits" Journal of Vacuum Science & Technology B. 2007; 25(6):2577-80. doi: 10.1116/1.2800322 which is incorporated herein by reference in its entirety. Techniques such as this help to circumvent the mismatch between nanotube growth temperatures and the maximum temperature tolerated by a CMOS device. In some cases, devices of the invention can made by employing a transfer of arrays of grown parallel tubes to arbitrary substrates (See, for example Kang et al. "High-performance electronics using dense, perfectly aligned arrays of single-walled carbon nanotubes" Nat Nano. 2007; 2(4):230-6) which is incorporated herein by reference in its entirety.

One way of having a single complex attached to the gate or to a region of the substrate proximate to the gate is to attach to the gate or to the region a binding reagent that binds with the polymerase enzyme complex, and to expose the substrate to a solution of polymerase enzyme complex at a concentration whereby a fraction of the nanoFETs have a polymerase enzyme complex becomes bound to gates or to nearby regions at a single molecule level. By selecting the right dilution level, Poisson statistics allows for up to 36% of the gates with a single complex attached, the rest having either no complex or multiple complex. Other methods including using steric interactions and providing highly specific bonding regions on the gate can provide greater levels of single complex than predicted by Poisson statistics.

The substrate is then exposed to a reaction mixture comprising a plurality of types of nucleotide analogs, each comprising a different conductivity label attached to the phosphate portion of the nucleotide analog. The attachment of the label to a phosphate portion allows for cleavage of the label by the polymerase as it breaks the polyphosphate strand when incorporating the nucleotide portion of the nucleotide analog into the growing strand. The label can be connected to the polyphosphate strand through a linker.

A voltage is applied between the source and drain of the nanoFET, such that, when a nucleotide analog resides in the active site of the enzyme, the conductivity label on the nucleotide analog produces a measurable change in the conductivity of the gate. The voltage can be DC, pseudo DC (where the measurement is essentially performed with a DC measurement, but the polarity is alternated to prevent corrosion), or AC. In some cases the frequency across the source and drain can be varied over time to assist in distinguishing the identities of different labels. The conductivity label is typically a charged species whose interaction with the gate results in a change in the conductivity at the gate. In some cases, the conductivity label comes into direct contact, e.g. repeated direct contact, with the gate, and in other cases the conductivity label may affect the conductivity of the gate by its proximity. Both the gate and the conductivity label can be made in a manner to improve the change in conductivity at the gate by the label. For example, as described in detail below the gate can be doped at different levels, either p doped or n doped, in order to tune its response. Conductivity labels can be charged species that are water soluble. The conductivity labels can have multiple charges, e.g. from about 2 to about 2,000 charges. The labels can comprise dendrimers or nanoparticles. Multiple labels can be employed, each having a different level of charge, in some cases, with some labels positively charged and some labels negatively charged.

During the polymerase enzyme reaction, and while the voltage is applied, an electrical signal comprising the current and voltage at the nanoFET over time is monitored. The electrical signal can indicate that an incorporation event for a specific type of nucleotide analog has occurred. One indication of an incorporation event is the length of the signal, since, depending on the kinetics of the polymerase enzyme used, an incorporation event will occur in a range of times that is different than a diffusion event, a non-cognate sampling event, or sticking of labels to the substrate. Various characteristics of the electrical signal can be used to determine that a particular nucleotide analog is in the active site and being incorporated. One characteristic is the amplitude of the conductivity. For example, four charged labels, each with different levels of the same type of charge can give four different levels of conductivity. The conductivity level can be designed to increase or to decrease in the presence of a given conductivity label, e.g. using positively charged and negatively charged labels. In addition to the numbers of charges, the density of the charges on the label can also affect the signal and the density of charge of the conductivity label can be controlled in order to control the signal at the nanoFET. The electric signal characteristics can also be controlled by controlling the structure of the nucleotide analog to change its current oscillation color characteristics.

The electrical signal can thereby provide the information required for determining the sequence of the template nucleic acid in the polymerase enzyme complex. Algorithms such as those described in U.S. Patent Application No. 2011/0256631 filed Oct. 20, 2011, and in U.S. Pat. No. 8,370,079 which are incorporated by reference herein in their entirety for all purposes.

Typically, the methods of the invention are carried out with four types of nucleotide analogs corresponding the natural nucleotides A, G, C, T, or A, G, C, U, each of the four types of nucleotide analogs having a different conductivity label. The nucleobase on the nucleotide analog will typically be the natural nucleobase, but modified nucleobases can be utilized as long at the polymerase enzyme that is used can effectively incorporate them into the growing strand.

In some aspects the invention provides a chip for sequencing a plurality of single nucleic acid template molecules. The chip has a substrate having a plurality of nanoFET devices, typically on its top surface. Each of the nanoFET devices has a source, a drain and a gate. Onto the gate of some of the nanoFETs on the substrate is a single polymerase enzyme complex bound to the gate or bound to the substrate proximate to the gate of the nanoFET. The polymerase enzyme complex includes a polymerase enzyme and a template nucleic acid. The template nucleic acid is typically primed, and ready to act as a template for nucleic acid synthesis. The substrate is configured such that the nanoFET device comes into contact with a sequencing reaction mixture. The substrate will typically have a well into which the reaction mixture is dispensed, or will have fluidic conduits or fluidic chambers providing the reaction mixture into contact with the nanoFET devices on the surface. The reaction mixture has the reagents required for carrying out nucleic acid synthesis including a plurality of types of nucleotide analogs. Two or more of the nucleotide analogs have different conductivity labels. The conductivity labels interact with the gate to modify its conductivity as described herein. The chip also has electrical connection sites for bringing current and voltage to the nanoFETs, and for receiving electrical signals from the nanoFETs.

The nanoFET on the chip can be any types of nanoFET, including the types of nanoFETs described herein, for example comprising a nanowire and/or comprising doped silicon.

The chip will typically have multiple nanoFET devices, for example, greater than 1,000 nanoFET devices, or greater than 10,000 nanoFET devices. The chip can have, for example, about 1,000 nanoFET devices to about 10 million nanoFET devices or about 10,000 nanoFET devices to about 1 million nanoFET devices.

The chip is typically made using semiconductor processing techniques, allowing for the inclusion of other functionality on the chip including electronic elements for one or more of: providing electrical signals to the nanoFETs, measuring the electrical signals at the nanoFETs, analog to digital conversion, signal processing, and data storage. The electrical elements can be, for example, CMOS elements.

Figure 3A:
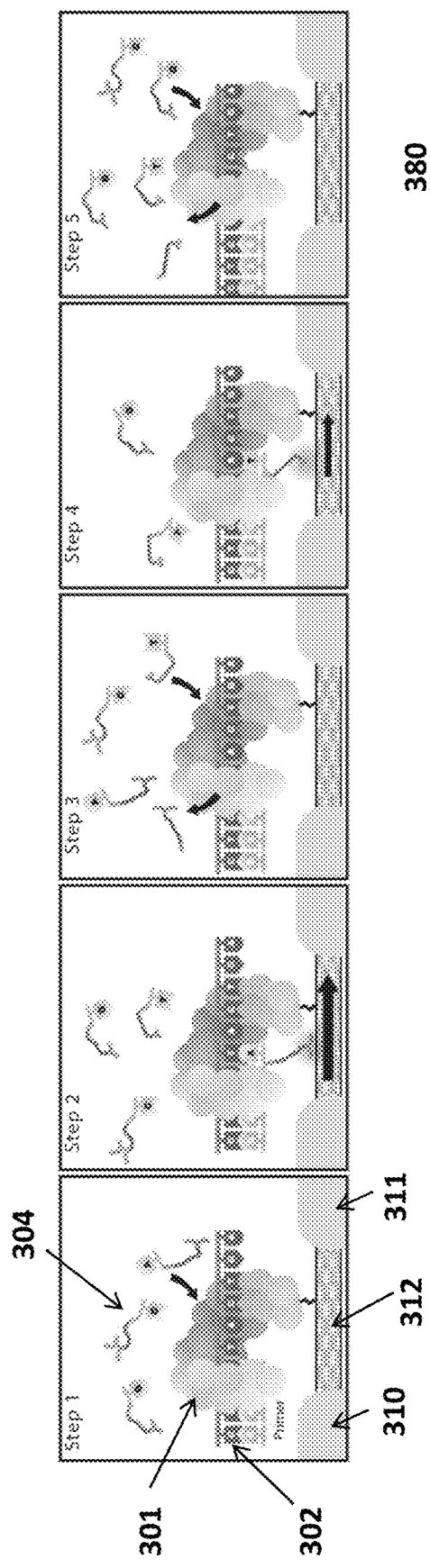
FIG. 3(A) illustrates the reaction at the polymerase enzyme.
Figure 3B:
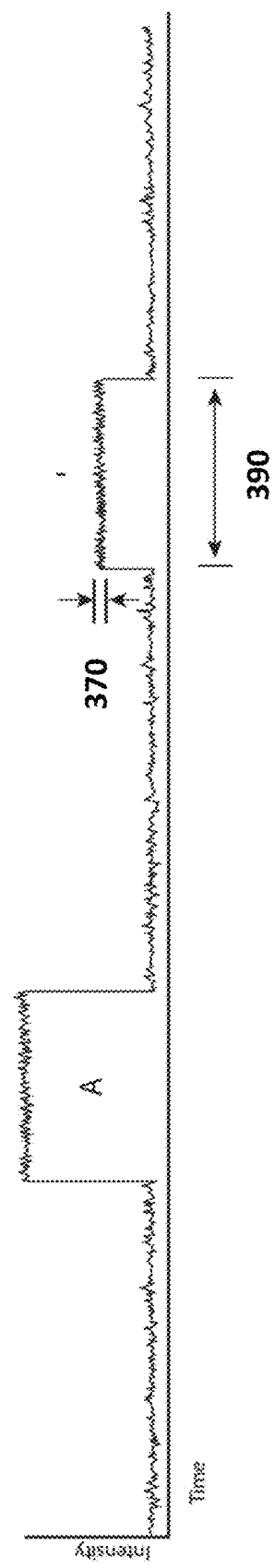
FIG. 3(B) illustrates the measurement of electrical signal versus time during the sequencing reaction.

FIGS. 3A and 3B provide another illustration of how single molecule nanoFET sequencing is accomplished. FIG. 3(A) shows a polymerase enzyme complex comprising a polymerase enzyme 301 and a primed template nucleic acid 302 bound through the polymerase enzyme (illustrated here as a covalent attachment) to the gate 312 (e.g. carbon nanotube) of a nanoFET. The nanoFET has the gate 312 spanning the source and drain 310 and 311. In the time period represented by Step 1, differentially labeled nucleotide analogs 304 are diffusing in solution near the nanoFET. FIG. 3(B) shows the signal at the nanoFET. In Step 1, the nanoFET signal is at baseline. In Step 2, a nucleotide analog corresponding to the base A is in the process of being being incorporated into the nascent strand complementary to the template. During this time, the conductivity label comes into contact (or close enough proximity) to increase the conductivity of the gate (represented by the arrow). FIG. 3(B) shows that in Step 2 there is an increase in intensity (e.g. an increase in current between the source and the drain). When the nucleotide analog corresponding to A is incorporated, the label is released, and the signal intensity returns to the baseline (Step 3). In Step 4, a nucleotide analog corresponding to T is being incorporated. This nucleotide analog has a different conductivity label the nucleotide analog corresponding to A, which produces a smaller increase in intensity. This is illustrated by the peak in FIG. 3(B) Step 4. The distance 370 represents a measure of the noise at the top of the peak. In the illustrated example, the signal to noise is on the order of 20 to 1. The distance 390 is the width of the peak corresponding to the incorporation of the nucleotide analog T, and represents the residence time of the nucleotide analog from when it binds to the polymerase to when the label is cleaved and is released into solution. In Step 5, the conductivity label is cleaved and released, and the signal returns to baseline as seen in FIG. 3(B). The arrow 380 represents the area of a sequencing reaction and is provided to illustrate that the area of the sequencing reaction can be relatively small compared to the area required in a corresponding optical detection method. For example, the area per sequencing reaction can be on the order of 1.5 microns squared.

Controlling the Location of the Nucleotide Exit Region of the Polymerase

As noted above, the instant system has an issue that is not typically encountered in sequencing methods, which is that at ionic strengths that are typically used for carrying out nucleic acid synthesis, charges in solution tend to be screened if they are farther than, for example, a few nanometers from the nanowire. One approach we have developed for improved signal in the sequencing methods of the invention is controlling the orientation of the polymerase with respect to the nanowire or nanotube. In particular, the polymerase is attached to the gate of the nanoFET such that the nucleotide exit region of the polymerase is oriented toward the nanoFET. The nucleotide exit region is the region of the polymerase where the phosphate portion of the nucleotide or nucleotide analog extends out of the polymerase. This is, of course, near the active site of the polymerase. As nucleotide incorporation proceeds, the nucleotide is held in the active site of the polymerase where chemistry occurs. The phosphate portion of the nucleotide extends out from the active site from a region of the polymerase. For a nucleoside triphosphate, the last two phosphates are in this region. As described in more detail herein, the nucleotide analogs of the invention have conductivity labels that are attached to the end of this phosphate chain of the nucleotide, therefore these conductivity labels extend from or exit from this portion of the polymerase. We have found that by controlling the orientation of this nucleotide exit region, we can more effectively control the signal from the conductivity labels on the nucleotide analog. The polymerase is immobilized on the nanowire in an orientation that ensures the detectable label is close to the nanowire detector when the nucleotide is in the active site of the polymerase. In some cases, this is accomplished with a single attachment between the polymerase and the nanowire. An exemplary schematic of this embodiment shown in FIG. 4A in which there is a single attachment through a linker to a portion of the polymerase near the nucleotide exit region. Certain DNA polymerases and other nucleic acid processing enzymes bind nucleotide triphosphates such that the terminal phosphate has a clear path to the bulk solution outside the enzyme. In FIG. 4A polymerase enzyme 410 is attached to the nanowire or nanotube through a linker 430. The nucleotide analog is 440 held within the enzyme in a nucleotide analog binding portion of the active site of the polymerase. A terminal phosphate label that is attached to a nucleotide 430 residing in the active site of the polymerase 410 extends out from that binding site and emerges from the polymerase enzyme at this location. The polymerase enzyme 410 is as attached to the nanowire or nanotube such that the enzyme is immobilized in an orientation that ensures or promotes a configuration in which the labeled portion of the nucleotide analog extending way from the polymerase is in close proximity to the nanowire detector. In certain embodiments, "close proximity" means a distance which is either less than the Debye screening length, less than the radius of gyration of the terminal phosphate label, or less than some combination of the Debye length and the radius of gyration of the label.

In some cases the polymerase is bound through a residue on the polymerase enzyme that is on the same side of the enzyme as the nucleotide exit region of the enzyme. In some cases, the residue is closer to the nucleotide exit region than a distance equal to one quarter of the longest distance from the nucleotide exit region back to the nucleotide exit region across the surface of the polymerase. In some cases the residue is less than 20%, less than 15%, or less than 10% of such distance relative to the nucleotide exit region. Having the polymerase bound such that the nucleotide exit region is oriented toward the substrate can be beneficial in the instant system, although this is not typically desirable in other sequencing systems. For example, U.S. Pat. No. 8,936,926 teaches that it is desirable to have the polymerase active site attached through a domain that is distal to the active site.

Methods are known in the art for linking a binding group to a desired position on the surface of a protein such as a polymerase. In some cases substitutions are made for amino acids at positions on the surface of the polymerase that do not unduly affect the activity of the enzyme, for example, with one or more attachment moieties for connection to the nanowire detector. For example, cysteine residues can be targeted specifically for attachment, e.g., in proteins that have a low cysteine density either overall or on the surface. The protein may be naturally low in cysteine, or may be engineered to have a reduced cysteine density. A cysteine residue can be added at a desired position and subsequently bound to an attachment moiety, e.g., at a residue near the exit tunnel of the polymerase. Alternatively, a naturally occurring cysteine residues in the protein can be used as an attachment point. Naturally occurring cysteine residues in positions not desired for use as attachment points are optionally substituted with nonreactive residues, e.g., if their presence interferes with attachment to the desired site. Further, even where a cysteine residue is engineered into a protein to serve as an attachment site, if a small portion of the proteins instead bind via a native cysteine, this is unlikely to alter the signal enough to be problematic, so engineering to reduce native cysteines may not be required. In other embodiments specific residues in a protein can be replaced with non-natural amino acids by creating a $21^{st}$ amino acid codon. In this case the $21^{21}$ amino acid can be a residue that bears an attachment site. Expression of proteins including unnatural amino acids containing ketone, azide, alkyne, alkene, and tetrazine side chains that can be used for attachment has been described, e.g., in Kim et al. "Protein conjugation with genetically encoded unnatural amino acids" Curr Opin Chem Biol. 17, 412-9 (2013).

A large number of suitable polymerases are known in the art, as detailed herein. In some cases, for example, a Phi29 DNA polymerase is used. For the sequence of wild-type Phi29 DNA polymerase, see SEQ ID NO:1 of U.S. Pat. No. 8,906,660, which is incorporated by reference herein in its entirety for all purposes. Various useful modified Phi29 polymerases are described hereinbelow; residue positions in such modified polymerases are numbered relative to the sequence of the wild-type polymerase. For Phi29 polymerase enzymes, position 375 is near the nucleotide exit region where the phosphate portion of the nucleotide extends out of the polymerase. In some cases, the polymerase is connected near position 375. For example, an attachment residue is substituted at or near position 375 so as to provide that the attachment is near the nucleotide exit region and thus the nucleotide exit region will be in close proximity to the detection zone of the nanowire. In some cases, the attachment is within 5 amino acids of position 375. Position 512 is also close to the exit region of the phi-29 polymerase, and in another preferred example, an attachment site is positioned at or near position 512. In some cases, the attachment residue is within 5 amino acids of position 512. In other examples, an attachment site is positioned at or near position 373, position 387, or position 510. In some cases, the attachment is within 5 amino acids of position 373, position 387, or position 510. In one exemplary embodiment, a cysteine residue is introduced at one or more of positions 373, 375, 387, 510, and 512; native cysteines (e.g., at position 106) are optionally removed, for example, by mutation to serine. In some cases, the attachment site is a residue that is less than 50 angstroms, less than 40 angstroms, less than 30 angstroms, less than 20 angstroms, or less than 10 angstroms from position 373, 375, 387, 510, or 512 (e.g., a residue having a non-hydrogen atom within the indicated distance from the alpha carbon of the stated residue in the Phi29 polymerase structure with PDB ID number 2PYL deposited at the RCSB Protein Data Bank, www (dot) rcsb (dot) org).

The position of the nucleotide exit region with respect to the nanowire can also be controlled using multiple attachments to the polymerase enzyme. Attachment of the polymerase through multiple sites can help to hold the enzyme in place by constraining the rotation of the enzyme. This helps to ensure that the conductance label is in close proximity to a nanowire detector. FIG. 4B shows an embodiment having two attachments linking a polymerase to a nanowire. The polymerase 412 is attached to the nanowire or nanotube through two linkers 432 and 434, which are each attached to a different portion of the polymerase 412. The two attachments are chosen so as to orient the nucleotide exit portion toward the nanotube or nanowire such that the labeled nucleotide analog 442 is held in proximity to the nanowire or nanotube 422 while the nucleotide analog is held within the polymerase. In some cases, one of the attachment sites is on one side of the active site and the other attachment site is on the other side of the active site.

In some embodiments, the polymerase is a Phi29 DNA polymerase and the linkers are attached at or near two residues selected from position 373, position 375, position 387, position 510, and position 512. As for the embodiments above, one or both of the attachment residues are optionally within five amino acids and/or within 50, 40, 30, 20, or 10 angstroms of one of the noted residues. In a preferred embodiment, the linkers are attached at or near both positions 375 and 512, for example one attachment residue is within 5 amino acids from position 375, and one attachment residue is within 5 amino acids from position 512. In other examples, the linkers are attached at or near both positions 373 and 512, positions 373 and 510, or positions 387 and 512. In some embodiments both of the attachment residues are closer to the nucleotide exit region or nucleotide exit region than a distance equal to one quarter the longest distance from the nucleotide exit region back to the nucleotide exit region (or nucleotide exit region to nucleotide exit region) across the surface of the polymerase. In some cases both residues are at a distance less than 20%, less than 15%, or less than 10% of such distance relevant to the nucleotide exit region or nucleotide exit region. Linking to a polymerase at multiple points, and in particular linking across the nucleotide exit region of a polymerase is described, for example in U.S. Pat. No. 7,745,116 which is incorporated by reference herein. In other embodiments, more than two attachment sites between the polymerase and the nanowire or nanotube are used. Methods for creating attachment sites on a nanotube or nanowire are described further below.

In some cases, a polyvalent linker is used that binds to multiple binding sites on the enzyme, and provides a single binding site to the nanowire detector. FIG. 4C provides an illustrative example of a polymerase linked to a trivalent linker molecule at two positions, where the trivalent linker is attached at only one position on a nanowire. The polymerase enzyme 416 is attached to the trivalent linker 436 in two places. The trivalent linker is attached to the nanotube or nanowire 426 through a single attachment point. The attachment points of the trivalent linker are selected such that the labeled nucleotide analog 446 is held in proximity to the nanowire or nanotube while the nucleotide analog 446 is in the active site of the polymerase 416. In some cases the two binding sites to the polymerase are on either side of the active site as described above for where two linkers are used. Specific examples of polyvalent linkers can be found in U.S. Patent Publication No. 2015/0011433, which describes polyvalent biotin binding capability for ensuring oriented binding to an avidin or streptavidin molecule and is incorporated herein by reference in its entirety. Polyvalent linkers attached across the active site of a polymerase are described, for example in U.S. Pat. No. 7,745,116 which is incorporated by reference herein for all purposes. These binding sites can be located, for example, on either side of the active site The attachment to the nanotube can either be covalent or non-covalent. In some cases, the linker is covalently bound to the polymerase, and the linker is bound to a group that has affinity for the carbon nanotube, such as an aromatic compound or binding protein. In some cases, engineered protein structures can be used to attach the polymerase to the nanotube or nanowire. One functionalization approach is to produce maleimide-modified SWNTs for polymerase attachment. This approach can take advantage of the fact that the many carbon nanotuges contain imperfections referred to as Stone-Wales (or 7-5-5-7) as well as other relatively reactive defect sites. This allows for carboxyl functionalization via oxidation by refluxing with mineral acids such as $HNO_3$. With carboxyl-SWNTs many options are available for further functionalization. One potential route is to convert these groups directly into a maleimide using EDC/sulfo-NHS coupling of N-(2-aminopropyl)maleimide. The maleimide can then be reacted with a single cysteine-containing mutant polymerase to yield the attached complex. Functionalization of nanotubes is known in the art. See, for example Balasubramanian, K. & Burghard, M. "Chemically functionalized carbon nanotubes" Small 1, 180-192 (2005); Hu, H. et al. "Determination of the acidic sites of purified single-walled carbon nanotubes by acid-base titration" Chemical Physics Letters 345, 25-28 (2001); Zhao, J., Park, H., Han, J. & Lu, J. P. "Electronic Properties of Carbon Nanotubes with Covalent Sidewall Functionalization" The Journal of Physical Chemistry B 108, 4227-4230 (2004); Chen, J. et al. "Solution properties of single-walled carbon nanotubes" Science 282, 95-98 (1998); Luong, J. H., Male, K. B., Mahmoud, K. A. & Sheu, F. S. "Purification, functionalization, and bioconjugation of carbon nanotubes" Methods Mol Biol 751, 505-532 (2011); Zhang, J. et al. "Effect of chemical oxidation on the structure of single-walled carbon nanotubes" The Journal of Physical Chemistry B 107, 3712-3718 (2003); Katz, E. & Willner, I. "Biomolecule-Functionalized Carbon Nanotubes: Applications in Nanobioelectronics" Chem Phys Chem 5, 1084-1104 (2004); Kanibera et al. "Covalently Binding the Photosystem I to Carbon Nanotubes" AIP Conf. Proc. 1199, 133 (2010); and Kuzmany, H. et al. "Functionalization of carbon nanotubes" Synthetic Metals 141, 113-122 (2004) which are incorporated by reference herein for all purposes. Another functionalization approach is to modify the SiO2 surface of silicon nanowires with reactive groups, e.g., amines, as described in Bunimovich et al. "Quantitative Real-Time Measurements of DNA Hybridization with Alkylated Nonoxidized Silicon Nanowires in Electrolyte Solution" J. Am. Chem. Soc. 128, 16323-16331 (2006), to which the polymerase can then be attached. Additional details on functionalizing nanotubes and nanowires are available in the art, including passivation of nanotube and nanowire surfaces. See, e.g., Zhang and Lieber "Nano-Bioelectronics" Chem. Rev. 116, 215-257 (2016) and Gao et al. "General Strategy for Biodetection in High Ionic Strength Solutions Using Transistor-Based Nanoelectronic Sensors" Nano Lett. 15, 2143-2148 (2015), which are incorporated by reference herein for all purposes.

One non-covalent approach for providing the attachments for the invention utilizes non-covalent nanotube binding components attached to the polymerase. In some cases, these non-covalent nanotube binding components are subsequently cross-linked to provide an even more robust attachment to the nanotube. In preferred embodiments, polymers such as proteins (polypeptides) are used as the non-covalent binding components. These polymeric components are useful for connecting the polymerase with the nanotube because a polymeric component can associate with the nanotube in multiple places. Even if each association of the polymer provides a weak interaction, the result of the multiple interactions can be a strong polymerase-nanotube association. Proteins are particularly preferred polymeric association compounds, but many other suitable polymers can be used. While the discussion herein is focused on proteins, it is to be understood that other suitable polymeric association compounds can be used in each place that a protein association compound is described. In some cases, a single subunit protein having both polymerase and nanotube binding components is employed. The nanotube binding component can be included with the production of a protein during cloning. Proteins that provide non-covalent attachment to carbon nanotubes are known in the art.

In some embodiments, the non-covalent binding components are engineered protein structures that wrap around the nanotubes in a controlled manner. The proteins provide the chemical functionality to attach to the polymerase and thereby bring the polymerase to the nanotube, in a controlled and defined manner.

An advantage of using associated proteins that wrap around the nanotube for non-covalent attachment of the polymerase is that these proteins can provide a surface functionalization of the nanotube in the region of polymerase binding. In some cases, the associated proteins provide screening of charges from the surface of the nanotube. For example, the proteins can be engineered such that they coat the nanotube away from the polymerase, and leave exposed a region near the polymerase in which the presence of the nucleotide analog in the active site is measured. In the regions away from the polymerase, the proteins can be used to reduce the noise from random ionic motion in the solution. The ability to prepare proteins with negatively charged, positively charged, hydrophobic, and hydrophilic amino acids in specific positions along the associated protein provides for controlling both the association of the protein with the nanotube and the effect of the associated protein on the conductivity of the nanotube in ionic solutions.

As discussed elsewhere herein, it is desired to have a single polymerase enzyme on a single nanotube. An aspect of the instant invention is the use of associated proteins to attach a single polymerase to a nanotube. One approach of the invention is to treat a solution of nanotubes with a low concentration of associating proteins such that a large fraction of the nanotubes with associated protein only have one protein bound. In some cases, the nanotubes having bound protein can be separated from the nanotubes without bound protein.

In some cases, the nanotubes are first treated with associated protein, and the polymerase enzyme is subsequently attached to the protein associated with the nanotube. An associated protein can be used which has reactive groups that bind reactive groups on the polymerase. Note that where we describe binding the polymerase, we also include binding of a polymerase that is complexed to a target nucleotide template, which is typically a primed nucleotide template. The polymerase bound to the template is sometime referred to as the polymerase-template complex or the polymerase complex. In some cases, it is desired to bind this complex to the nanotube or to the associated protein on the nanotube. In other cases, the polymerase without template can be bound to the nanotube, and the template can be added in a subsequent step.

In some cases the protein-polymerase compound or conjugate is first formed, and this compound or conjugate is added to the nanotube such that the protein associates with the nanotube.

The treatment could be carried out either before or after the nanotubes are attached to the source and drain to form the FETs. If the treatment is prior to formation of the FET, and if the associated proteins have an affinity tag such as a his-tag, this could be used to separate the nanotubes having protein bound from the naked nanotubes. The associated protein can have binding groups for the coupling of the polymerase Where the polymerase is coupled before the formation of the FET, then there is the issue of forming highly conductive attachments of the nanotube with the source and drain electrodes while maintaining the activity of the polymerase.

In some cases, two reactive groups are positioned the desired distance along the nanotube binding protein, and the polymerase is attached to each of these positions. For example, a protein can be prepared having two cysteine groups, separated by the desired spacing distance. These cysteine groups can be used to react with the polymerase by methods well known in the art.

The associated proteins tend to wrap around the carbon nanotube. In some cases, the functional groups on the associated protein can be spaced such that, due to the wrapping of the protein, the functional groups are presented on the same side of the nanotube. The functional groups can be placed on the same side of the nanotube, for example, 1, 2, 3, 4, 5, 6, or more turns from each other. For example, the phasing of cysteine functionality can be controlled to ensure that the thiols on the cysteines ended up on the same side of the nanotube and accessible for reaction with two regions of a polymerase or with two linker groups extending from the polymerase.

One advantage of the associated polymeric compounds of the invention is that they provide a variety of approaches to result in the single molecule nanoFET devices of the invention.

Figure 6:
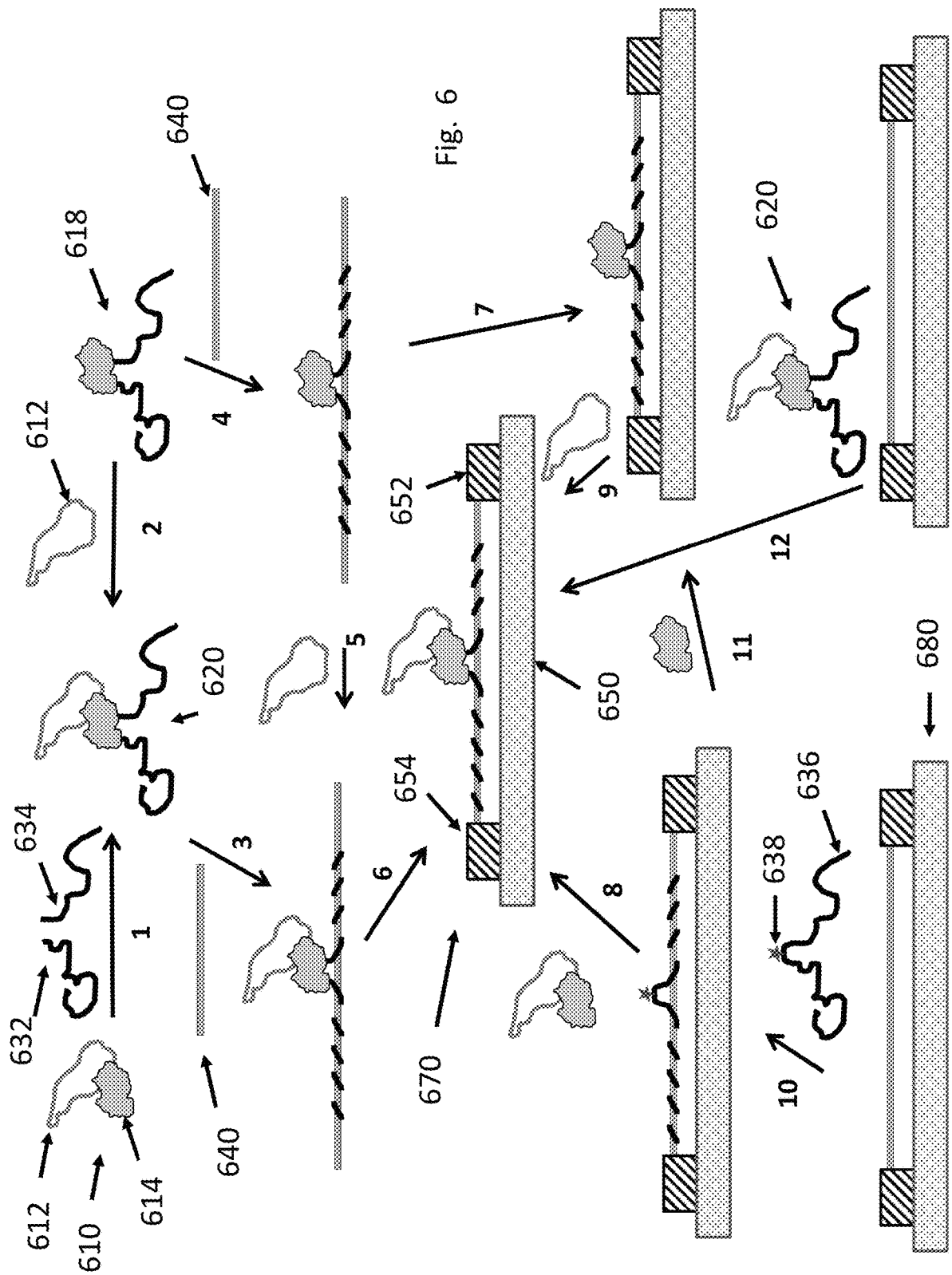
FIG. 6 shows various approaches for attaching the polymerase-template complex to the nanotube with polymeric non-covalent binding components such as proteins.

FIG. 6 shows various approaches for attaching the polymerase-template complex to the nanotube with polymeric non-covalent binding components such as proteins. The figure illustrates how the polymeric non-covalent binding components offer a number of alternative approaches for forming the nanoFET sequencing devices of the invention. The approach selected will depend on factors such as engineering considerations, materials, and process tradeoffs that will influence yield and performance. The ability to pursue a number of different processing strategies is an advantage of this method of binding the polymerase to the nanotube. In FIG. 6, the polymeric binding agent has two strands interacting with the nanotube such that the polymerase is attached in a central location and having polymeric binding agent extending away from it down the nanotube in both directions. This can be advantageous, as the polymeric binding agent can be used to control the properties at the surface of the nanotube. In some cases, the polymeric binding agent can be attached at its end to a single polymerase binding agent. One of skill can appreciate how this construct can also be used in each of the approaches shown in FIG. 6. In preferred embodiments, the polymer binding agent comprises a protein. In some cases, the polymer binding agent is cross-linked after it is bound to the nanotube to further enhance stability. The cross-linking reaction can be carried out at any step in the process after the polymer binding agent associates with the nanotube. FIG. 6 refers to various numbered steps. It is to be understood that while labeled as a single step, in some cases the numbered step involves multiple separate processes. The approaches are shown using a carbon nanotube, but any suitable nanowire can be used.

One approach to producing a nanoFET sequencing device of the invention follows steps 1, 3, and 6 of FIG. 6. In step 1, a template complex 610 including polymerase enzyme 614 and template molecule 612 is coupled to polymeric binding agents 632 and 634. The coupling of binding agents can be done either covalently or non-covalently. Selective binding groups such as biotin/streptavidin can be used for non-covalent coupling. SpyCatcher/SpyTag-like approaches can be used for selective covalent coupling. (See, e.g., Zakeri et al. "Peptide tag forming a rapid covalent bond to a protein, through engineering a bacterial adhesion" Proc Natl Acad Sci USA 2012, 109, E690-E697 for a description of SpyCatcher/SpyTag coupling). The template molecule is shown here as a circular template molecule, but any suitable template molecule including a linear template molecule can be used. The two polymeric binding agents can be connected, for example, across the active site of the polymerase enzyme to orient the exit region of the polymerase toward the nanotube. In step 3, the enzyme template complex with attached polymer binding agents 620 is then mixed with carbon nanotubes 640 in solution under conditions in which the polymeric binding agents complex with the nanotube to immobilize the complex. The complexation can be carried out under conditions that promote having a single polymerase complex per nanotube, for example by providing an excess of carbon nanotubes. In some cases, after the complexation reaction, purification is carried out to enrich the sample for the nanotubes having a polymerase template complex attached. This type of purification can be carried out using affinity tags on the polymerase or polymer binding agent. Affinity tags for protein purification, for example His-tags, are well known in the art. Note that this type of purification of polymerase-nanotube complex can be carried out at any suitable step shown in FIG. 6. In step 6, the nanotube having enzyme-template complex bound is deposited onto a substrate 650, and source and drain electrodes 652 and 654 are formed to produce a nanoFET device for sequencing 670.

An alternative approach is provided by following steps 2, 3, and 6. Here, the polymerase with attached polymer binding agents 618 is produced and in step 2 is mixed with the template nucleic acid 612 to form the enzyme-template complex attached to the polymer binding agents 620. The polymerase with attached polymer binding agents 618 can be produced by coupling as described above (e.g., by coupling the agent to a reactive residue in the polymerase), or the construct 618 can be made directly, for example by cloning techniques in which the protein binding agents and the polymerase are expressed as a fusion protein. A polypeptide binding agent can be expressed as a fusion with the N-terminus of the polymerase, with the C-terminus of the polymerase, or at an internal site in the polymerase. For Phi29 DNA polymerase, to orient the exit region of the polymerase near the nanotube, fusion is preferably with the N-terminus. After production of 618, steps 3 and 6 are carried out as described above to produce a nanoFET device for sequencing 670.

Another approach proceeds through steps 4, 5, and 6. In step 4, polymerase with attached polymer binding agents 618 is mixed with nanotubes 640 to produce a polymerase bound to the nanotube through the polymer binding agents. This is added to template 612 in step 5 to form an enzyme-template complex bound to the nanotube. Step 6 is then carried out as described above to produce a nanoFET device for sequencing 670. Alternatively, one can proceed from the polymerase bound to the nanotube through the polymer binding agents produced in step 4 through steps 7 and 9 to produce a nanoFET device for sequencing 670. This route allows for adding the template to form the enzyme complex as the last step to be carried out on the substrate.

Steps 10 and 8 provide a route that begins with the carbon nanotube nanoFET structure 680. In step 10, to the nanoFET structure 680 is added polymer binding agent 636 having enzyme coupling group 638 under conditions in which the polymer binding agent 636 complexes with the nanotube. In step 8, the enzyme-template complex is coupled to the polymer binding agent on the nanotube through the enzyme coupling group 638 to produce a nanoFET device for sequencing 670. An alternative to step 8 is to perform steps 11 and 9, adding the polymerase first, followed by complexation with the template.

In some cases, we start with carbon nanotube nanoFET device 680, and add to it enzyme template complex with attached polymer binding agents 620 under conditions in which the polymer binding agents associate with the nanotube to produce a nanoFET device for sequencing 670.

For approaches embodied in steps 1-9 of FIG. 6, the deposition of the nanotubes onto the substrate and the formation of the source and drain electrodes 652 and 654 is carried out in the presence of the polymerase enzyme or polymerase enzyme-template complex. For these approaches, the electrodes must be deposited in a relatively gentle manner in order to preserve the activity of the polymerase enzyme. For these approaches, some conventional electrode deposition steps such as plasma or vacuum evaporation cannot generally be used. Here, electrodeposition of electrodes under relatively mild conditions, e.g. near room temperature, near neutral pH, are used.

Polymer binding agents such as proteins can be coated onto the nanotube to control surface properties of the nanotube and protect the nanotube from direct contact with the solution in certain regions. Some of the polymer binding proteins can be attached to the polymerase as shown in FIG. 6. In addition, or alternatively, the polymer binding agent without polymerase enzyme can be used to coat other portions of the nanotube to control nanotube surface properties in that region. By using different polymer binding agents near the polymerase and away from the polymerase, properties of different regions of the nanotube can be controlled. In some cases, polymer binding agents can be produced that coat substantially all of the nanotube except for a region near the polymerase. The polymer binding agents could be used to reduce the noise from random ionic motion in the solution by providing screening in those areas, while allowing the solution to freely contact the nanotube in other areas, e.g. the portion of the nanotube near the polymerase exit region. The ionic makeup, hydrophobicity, hydrophilicity, etc. of the polymer binding agents, e.g. proteins, can be designed to control the surface properties of the nanotube. As noted, the polymer binding agent can be cross-linked, e.g., to the nanotube or, where multiple copies of the agent are employed to coat the nanotube, to the other copies to form a stable shell around the nanotube. Binding agents can also be employed, e.g., to purify nanotubes with a specific desired diameter from a heterogeneous mixture, modify solubility of the nanotubes, modulate nanotube conductivity, and/or control accessibility of the nanotube surface.

Polymer binding agents that can be adapted to the practice of the current invention are known in the art. See, e.g., the polypeptides described in Grigoryan et al. "Computational Design of Virus-Like Protein Assemblies on Carbon Nanotube Surfaces" Science 332, 1071-1076 (2011); Calvaresi and Zerbetto "The Devil and Holy Water: Protein and Carbon Nanotube Hybrids" Acc. Chem. Res. 46, 2454-2463 (2013); Yu et al. "Recognition of Carbon Nanotube Chirality by Phage Display" RSC Adv. 2, 1466-1476 (2012); and Chiu et al. "Molecular Dynamics Study of a Carbon Nanotube Binding Reversible Cyclic Peptide" ACS Nano 4, 2539-2546 (2010), which are hereby incorporated by reference in their entirety. As additional examples, the graphene binding peptides described in, e.g., Hughes and Walsh "What makes a good graphene-binding peptide? Adsorption of amino acids and peptides at aqueous graphene interfaces" J. Mater. Chem. B 3, 3211-3221 (2015) and Russell and Claridge "Peptide interfaces with graphene: an emerging intersection of analytical chemistry, theory, and materials" Anal Bioanal Chem. 408, 2649-58 (2016) (hereby incorporated in their entirety) can be coupled to or expressed as a fusion with the polymerase. Optionally, two or more copies of such polypeptides (e.g., tandem copies, optionally separated by spacer) are expressed as a fusion with the polymerase, e.g., with the N-terminus of a Phi29 DNA polymerase. Affinity of the fusion protein for the nanotube can readily be modulated by changing the number of repeating units of the binding peptide and/or by mutation of the binding peptide.

Figure 25:
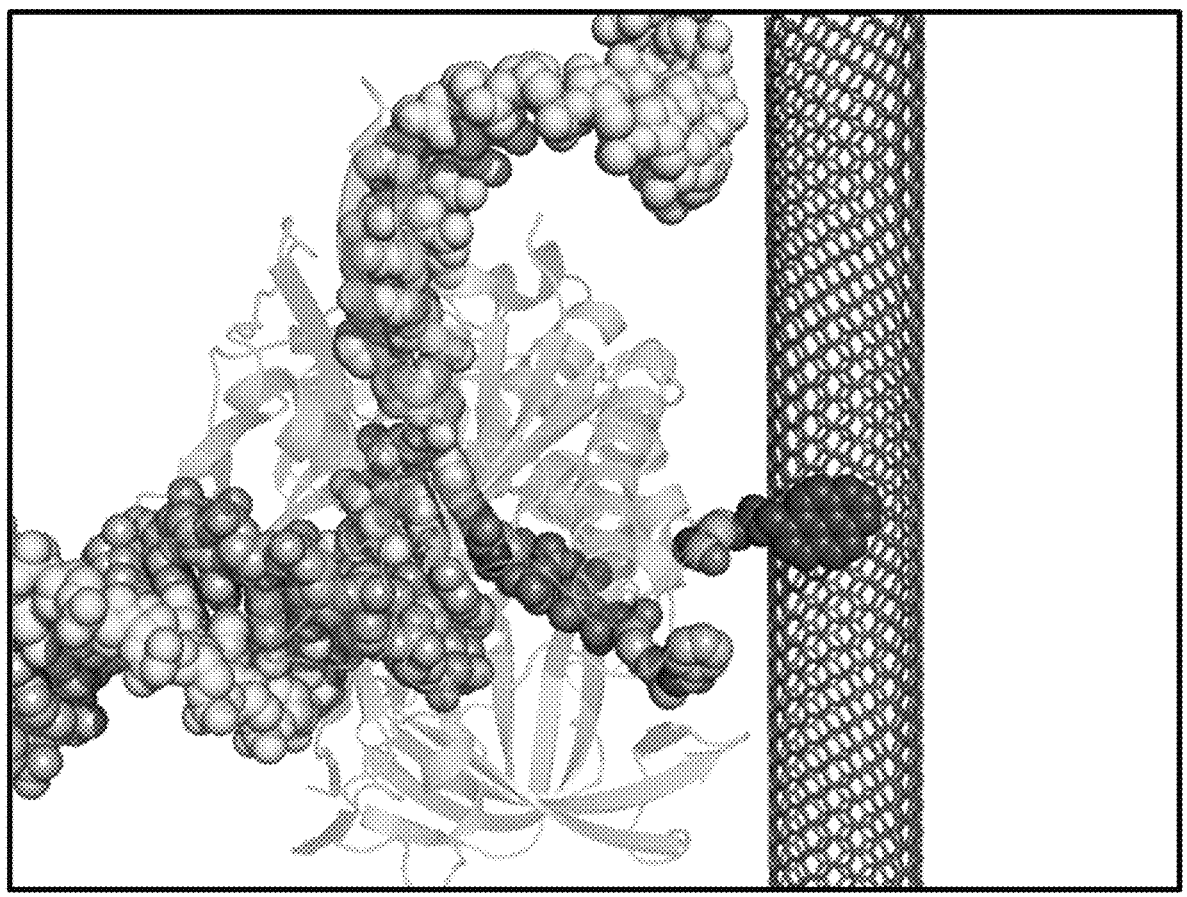
FIG. 25 shows an example of a polymerase bound to a nanotube by a single attachment through a pyrene covalently linked to a side chain of the polymerase.

In other exemplary embodiments in which non-covalent nanotube binding components are attached to the polymerase, non-polymeric moieties are employed as the nanotube binding components. In some embodiments, hydrophobic moieties such as polycyclic aromatic moieties are used as the non-covalent binding components. Exemplary polycyclic aromatic groups include, but are not limited to, naphthalene, anthracene, phenanthrene, tetracene, chrysene, triphenylene, pyrene, pentacene, benzo[a]pyrene, corannulene, benzo[ghi]perylene, coronene, ovalene, and benzo[c]fluorene. In a preferred embodiment, pyrene is used as the non-covalent binding component. The polycyclic aromatic moiety can be attached to the polymerase using techniques known in the art, e.g., via a reactive residue in the polymerase as described above. A linker is optionally included between the polycyclic aromatic moiety and the polymerase residue, for example, to achieve the desired spacing between the nucleotide exit region and the nanotube. As one example, a pyrene-linked maleimide can be conjugated to a cysteine residue in the polymerase. See, e.g., Olsen et al. "Electronic Measurements of Single-Molecule Processing by DNA Polymerase I (Klenow Fragment)" J. Am. Chem. Soc. 135, 7855-7860 (2013); Choi et al. "Single Molecule Dynamics of Lysozyme Processing Distinguishes Linear and Cross-linked Peptidoglycan Substrates" J Am Chem Soc. 134, 2032-2035 (2012); and Choi et al. "Single-Molecule Lysozyme Dynamics Monitored by an Electronic Circuit" Science 335, 319 (2012), which describe such coupling. The aromatic pyrene group can associate with the nanotube via π-π interactions. Optionally, washing steps can be employed to yield an average of one polymerase per nanotube; see, e.g., Choi et al. J Am Chem Soc. 134, 2032-2035 (2012), hereby incorporated by reference in its entirety. Suitable residues for attachment of the polycyclic aromatic moiety in a Phi29 DNA polymerase have been described above, including position 373, position 375, position 387, position 510, and position 512 or residues within five amino acids and/or within 50, 40, 30, 20, or 10 angstroms of position 373, position 375, position 387, position 510, or position 512. FIG. 25 shows an example of a Phi29 polymerase bound to the gate of a nanoFET by a single attachment through a pyrene linked with a cysteine introduced by mutation at position 373 of the polymerase. It will be evident that the polymerase can be attached to the nanotube through multiple such interactions. For example, pyrene-linked maleimide can be reacted with a pair of cysteine residues flanking the exit region as described above. For Phi29 DNA polymerase, useful pairs of residues include, but are not limited to, two residues selected from position 373, position 375, position 387, position 510, and position 512 (or from residues within five amino acids and/or within 50, 40, 30, 20, or 10 angstroms of one of the noted residues). In a preferred embodiment, the linkers are attached at or near both positions 375 and 512; for example, one attachment residue is within 5 amino acids from position 375, and one attachment residue is within 5 amino acids from position 512. In other examples, the linkers are attached at or near positions 373 and 512, positions 373 and 510, or positions 387 and 512.

Where multiple positions on the polymerase are linked to the nanowire, multiple binding sites can be engineered into the nanowire detector. These binding sites are arranged at desired distances to each other, for example, either using random functionalization or using a templating molecule such as a DNA strand or polypeptide that can provide binding sites at defined positions relative to each other. Where there are two attachments to the nanowire or nanotube, in some cases, both attachments are covalent, in some cases, both attachments are non-covalent, and in some cases, one attachment is covalent and the other is non-covalent. Where random functionalization of the nanotube is used, it can be useful to have one attachment be covalent, and allow the other attachment to be non-covalent.

In some cases, orienting the nucleotide exit region of the polymerase toward the gate of the nanoFET involves having the polymerase attached to the nanoFET through a linker attached near the nucleotide exit region of the polymerase. In this context, near means, for example, on the same side of the polymerase. In some cases the polymerase is attached through a linker to a site that is less than 50 angstroms, less than 40 angstroms, less than 30 angstroms, less than 20 angstroms, or less than 10 angstroms from the nucleotide exit region. In some cases the polymerase has two different attachment points to the nanoFET gate in which at least one of the attachment points is near the nucleotide exit region of the polymerase. In some cases, one or both of the attachment points is less than 50 angstroms, less than 40 angstroms, less than 30 angstroms, less than 20 angstroms, or less than 10 angstroms from the nucleotide exit region.

Figure 5:
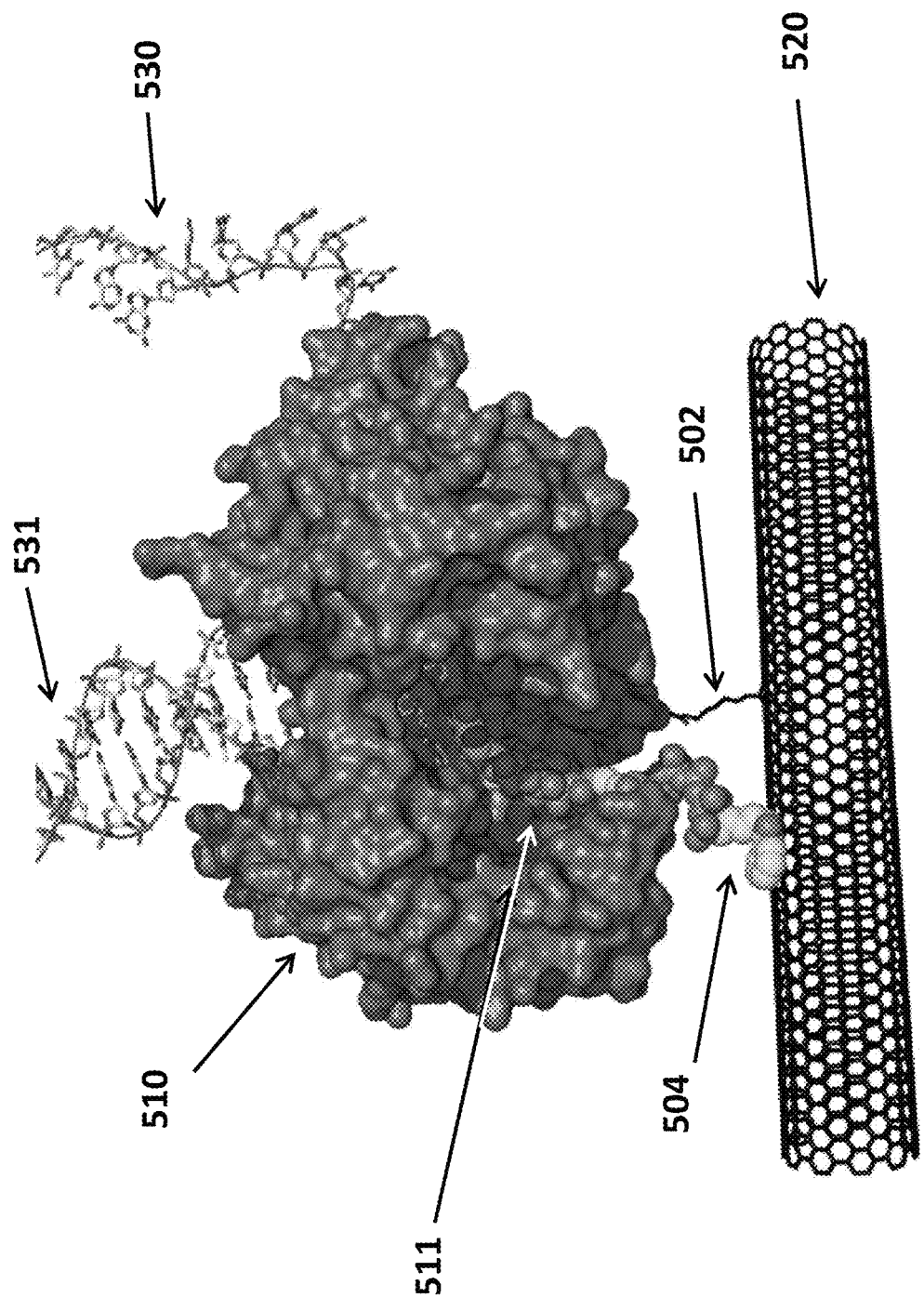
FIG. 5 illustrates carrying out single molecule nanoFET sequencing with a polymerase having its nucleotide exit region oriented toward a carbon nanotube gate of a nanoFET using a single attachment to the nanotube.

FIG. 5 shows an example of a polymerase enzyme 510 bound to the gate of a nanoFET by a single attachment where the polymerase is oriented such that the nucleotide exit region 511 of the polymerase is oriented toward the gate. The single attachment point to the polymerase is through linker 502 to carbon nanotube gate 520. In this embodiment the link to the nanotube is covalent, and the length of the linker 502 is relatively short. For example, in some cases the linker is between about 1 nm and about 10 nm in length, about 1 nm to about 5 nm in length, or about 2 nm to about 8 nm in length. While the polymerase has some freedom of motion, the link maintains the polymerase such that the nucleotide exit portion of the polymerase 511 is oriented toward the nanotube 520. This allows for the conductivity label 504 on the nucleotide analog in the active site of the enzyme to extend, and in some cases, as the embodiment shown, come into contact with the nanotube while the enzyme is in the process of incorporating the nucleotide. As can also be seen in this illustration, orienting the polymerase in this manner can also have the added benefit keeping the template nucleic acid away from the nanotube where it might produce background noise. It can be seen here that both the entering template 530 and the exiting template 531 are oriented generally away from the carbon nanotube.

Another aspect of the invention is the use of non-covalent transient binding moieties that partition to a nanotube in order to bias the orientation of the nucleotide exit region towards the detection zone of the device. For example, in certain embodiments comprising multiple attachment sites, one of the attachment sites is modified with a covalent attachment (or a non-covalent tight binding target such as streptavidin-biotin) and a second binding site is functionalized with a hydrophobic moiety that is designed to partition heavily into a bound state with the nanowire detector. A wide range of binding affinities can be used, so long as the aggregate kinetics of binding and unbinding are fast compared with the residence time of a typical terminal phosphate label on a nucleotide analog that is participating in a binding event. For example, a significant benefit can come from a binding moiety that has a 10% or 20% or 50% duty cycle of binding to the nanotube as long as the off-rate is faster than about 100 per second, or more preferably faster than 1000 per second. In another mode, moieties that provide a duty cycle of greater than 95% could be used even with slower off rates by simply tolerating the sequencing errors that result from incorporation events that take place while the enzyme is in the wrong orientation.

Figure 7:
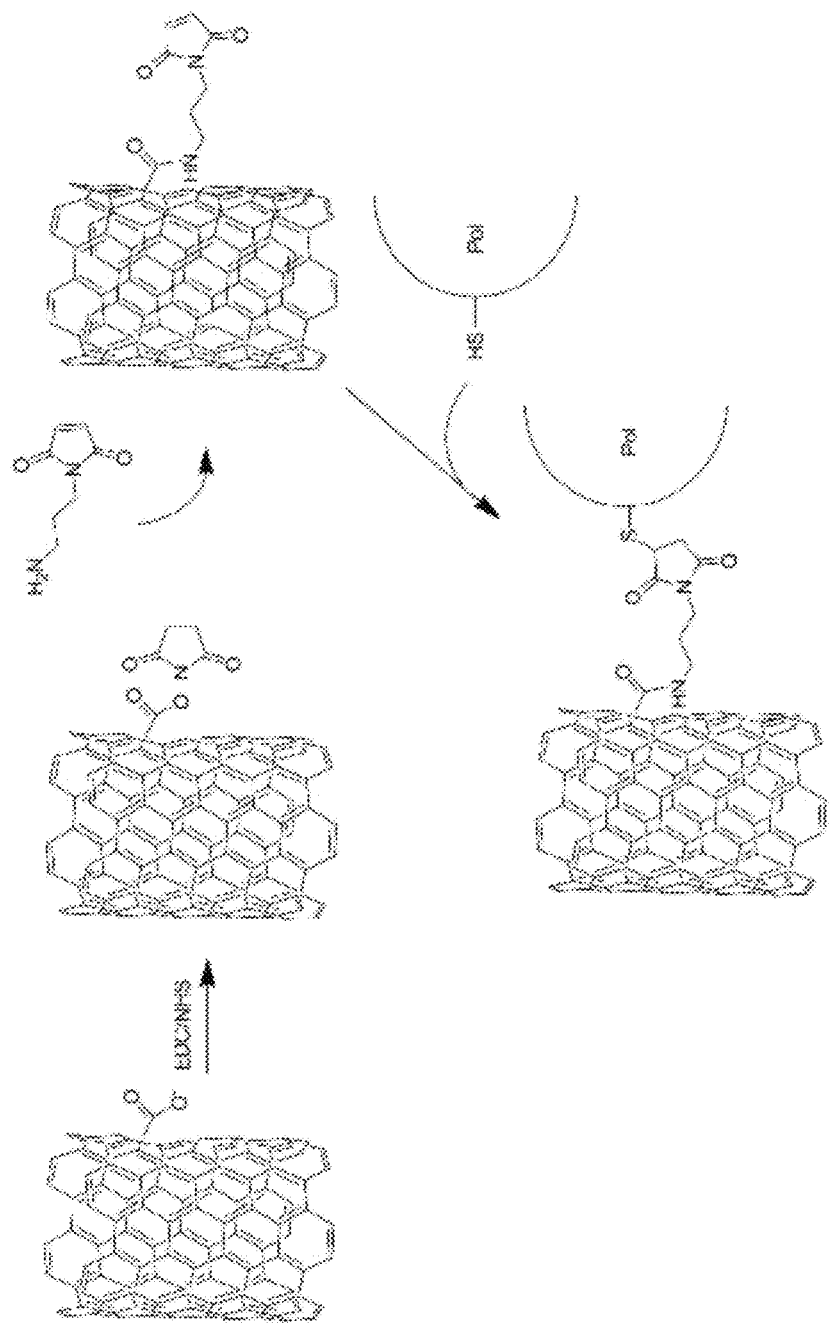
FIG. 7 shows representative chemistry for covalent attachment of a polymerase enzyme to a carbon nanotube.

In some embodiments, it is desirable for there to be a covalent connection between the polymerase enzyme and the gate. FIG. 7 shows one approach for such a covalent attachment. First a carboxylic acid is introduced onto the nanotube via oxidation. The carboxylic acid is derivitized to an N-hydroxy succinimidyl (NHS) ester. The ester is then extended using a small molecule having an amine end and an maleimide end. The maleimide group on the nanotube will react with a thiol group of a cysteine residue on the polymerase to provide a covalent attachment. By modifying the polymerase using well known methods, specific cysteine residues can be introduced (e.g. near the nucleotide exit region), and undesired cysteine residues can be removed. See, e.g., the positions noted above. Such covalent attachment to nanotubes is described, for example in Sorgenfrei, et al. "Label-free single-molecule detection of DNA-hybridization kinetics with a carbon nanotube field-effect transistor" Nature Nanotechnology. 2011; 6(2):125-31. doi: 10.1038/nnano.2010.275; Goldsmith et al. "Monitoring Single-Molecule Reactivity on a Carbon Nanotube" Nano Letters. 2008; 8(1):189-94. doi: 10.1021/nl0724079; and Sorgenfrei et al. "Debye Screening in Single-Molecule Carbon Nanotube Field-Effect Sensors" Nano Letters. 2011; 11(9):3739-43. doi: 10.1021/nl201781q, the disclosures of which are incorporated herein by reference in their entirety for all purposes.

Polymerase Bound Through Fusion Protein or Particle

In some aspects of the invention, the sensitivity of the nanoFET array is enhanced by attaching the biomolecule, e.g. polymerase enzyme, to the gate of the nanoFET through a fusion protein that allows the electric field lines to penetrate it, allowing the gate to be more sensitive to the presence of a conductivity label such as a charged label in or near the active site.

As described above, the presence of ions including counterions in the solution have the effect of screening or blocking the penetration of the electric field into the solution. In certain aspects, the sensitivity of the nanoFET with respect to a labeled nucleotide is enhanced by displacing solution-phase counterions using a molecular crowding species, e.g. a dielectric nanoparticle (e.g., polystyrene spheres, optionally 5 nm in diameter), a zwitterionic polymer, or other dielectric material that is placed between the charge of interest and the detection zone of the nanowire detector. In some embodiments, this material comprises the enzyme peptide chain itself and/or an additional polypeptide that is either fused or separate from the enzyme or a dielectric particle such as polystyrene or silica.

Figure 8:
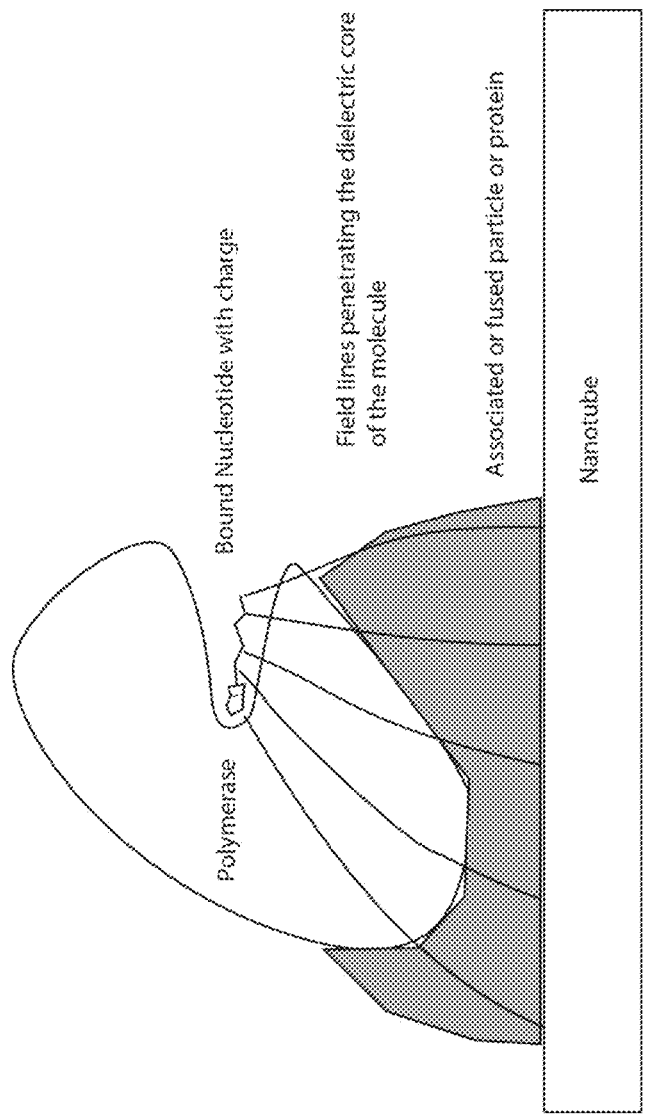
FIG. 8 illustrates how a fused particle or protein bound between the nanoFET gate and the polymerase can result in improved detection of charged species at or near the active site of the polymerase.

The space that is occupied by a dielectric medium is not available to host screening counter-ion charges and thus the detection range of the nanowire can be extended specifically with formed dielectric spaces to include the active site. For example, in some embodiments, the nucleic acid processing enzyme is fused with a polypeptide whose folding characteristics are engineering to envelop the nanowire and displace counterions from residing between the nanowire and the protein. In this mode, electric field lines originating from the charge of interest will penetrate through the dielectric portions of one or both of the enzyme or the associated or fused envelope peptide such that they are able to reach the detection zone of the FET device, for example, as shown in FIG. 8.

Examples of fusion proteins comprising a polypeptide, e.g. a Phi29 polymerase, and another, optionally non-functioning, protein with a hydrophobic core have been previously described, e.g., in U.S. Pat. No. 8,323,939 and U.S. Patent Publication No. 2010/0260465, both of which are incorporated herein by reference in their entireties. This fusion protein creates a zone of further penetration into the surrounding space and will thus increase sensitivity. In yet further embodiments, the nanoparticle or other dielectric material is linked to a nanowire near or on which the enzyme is positioned to block screening counterion charges and improve detection.

Assisted Loading of Carbon Nanotubes onto the Chip

As described above, the instant invention provides a number of different methods for loading nanotubes onto chips for the formation of nanoFET devices for single molecule sequencing. In some cases, the nanotubes are loaded onto the surface, and then a polymerase enzyme is attached. In other cases, the polymerase is first attached to the nanotube and the nanotube is subsequently loaded onto the surface of the chip. In either of these two approaches, it can be useful to use electric fields to assist in the loading of the nanotubes onto the chip. Approaches such as described in Islam et al. "A general approach for high yield fabrication of CMOS-compatible all-semiconducting carbon nanotube field effect transistors" Nanotechnology 23 (2012) which is incorporated by reference herein for all purposes can be used.

Figure 9:
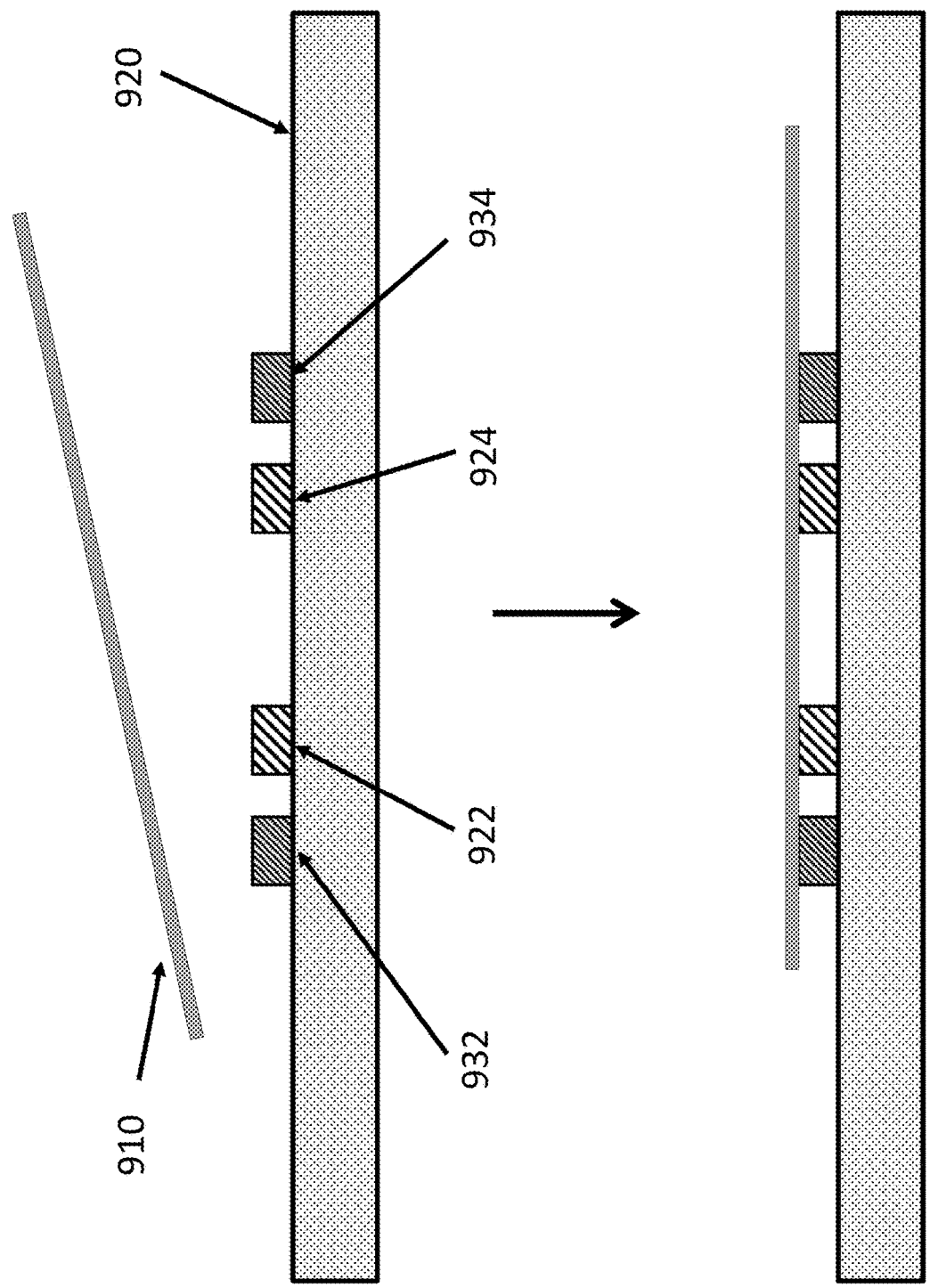
FIG. 9 shows a method of the invention for using electric field to deposit a nanotube onto the surface of the chip.

FIG. 9 shows a method of the invention for using electric field to deposit a nanotube onto the surface of the chip. The chip 920 has an array of sets of electrodes. Each set of nanoscale electrodes is arranged in a line across the chip within that set of electrodes. The distance between the first and last electrode in the line is generally selected to be less than the length of the nanotubes to be deposited. In FIG. 9, the chip 920 has four electrodes in a line for each set. The inner electrodes 922 and 924 will become the source and drain of the nanoFET that is formed. The outer electrodes 932 and 934 are used to provide a field for attracting, aligning, and depositing the carbon nanotube 910 from solution. In some cases, the deposition is carried out using only two electrodes per set, in which the two electrodes are used both for deposition of the nanotube, and also to act as source and drain for the nanoFET. An advantage of using 4 electrodes per set as shown in FIG. 9 is that the outer electrodes 932 and 934 can be prepared for providing the deposition electric field, while the inner electrodes 922 and 924 can be prepared for optimal detection of small current changes as source and drain for the carbon nanotube nanoFET. For example, the outer electrodes 932 and 934 are made with the materials and at the dimensions for providing a higher voltage and higher current for deposition. The deposition electric field can be a DC field, an AC field, or a combination of an AC and DC field. The application of an AC field allows for the use of dielectrophoretic forces for attracting, aligning, and depositing the carbon nanotubes.

Typically, after the deposition of the nanotube in FIG. 9 is completed, conductive material is selectively deposited over the source and drain electrodes to provide a more robust electrical connection to the nanotube. This deposition of conductive material over the source and drain can be carried out in vacuum, e.g. by vapor or plasma deposition, or in solution e.g. by electrodeposition. Where vacuum processes are used to deposit the conductive material over the source and drain the liquid that was used to deposit the nanotubes must be removed. In some cases the removal of the liquid layer from the chips can cause damage to the nanostructures due to surface tension forces during evaporation. In order to ensure the integrity of the structures, we have found that fluid exchange can be carried out such that the final evaporation is performed using a fluid with a relatively low surface tension. One fluid exchange progression is, for example, water exchanged with ethanol, and ethanol exchanged with ethyl ether, which is then evaporated from the chip. Other solvent exchange combinations to provide evaporation of low surface tension liquids are known in the art. Where the structures are even more fragile, super-critical fluid removal can be used. For example, critical point drying of the carbon nanotube nanoFETs with super-critical $CO_2$.

In some cases, the outer electrodes can also be used in the nanoFET detection, for example by providing a voltage across the outer electrodes 932 and 934, and measuring a voltage drop across the inner electrodes 922 and 924 for enhanced nanoFET detection. In some cases, the outer electrodes 932 and 934 are kept at the same potential as the inner electrodes 922 and 924 during measurement. In some cases, the nanotube is selectively cleaved between the inner and outer electrodes to electronically isolate the inner from the outer electrodes for nanoFET detection.

The chips will typically have 1 million, 5 million, 10 million, 15 million, 20 million or more sets of electrodes. Although the above is described for use in single molecule sequencing, it will be understood that these deposition methods as well as other methods described herein that are not limited to sequencing can be used to produce nanotube nanoFET arrays for any suitable application.

Figure 10:
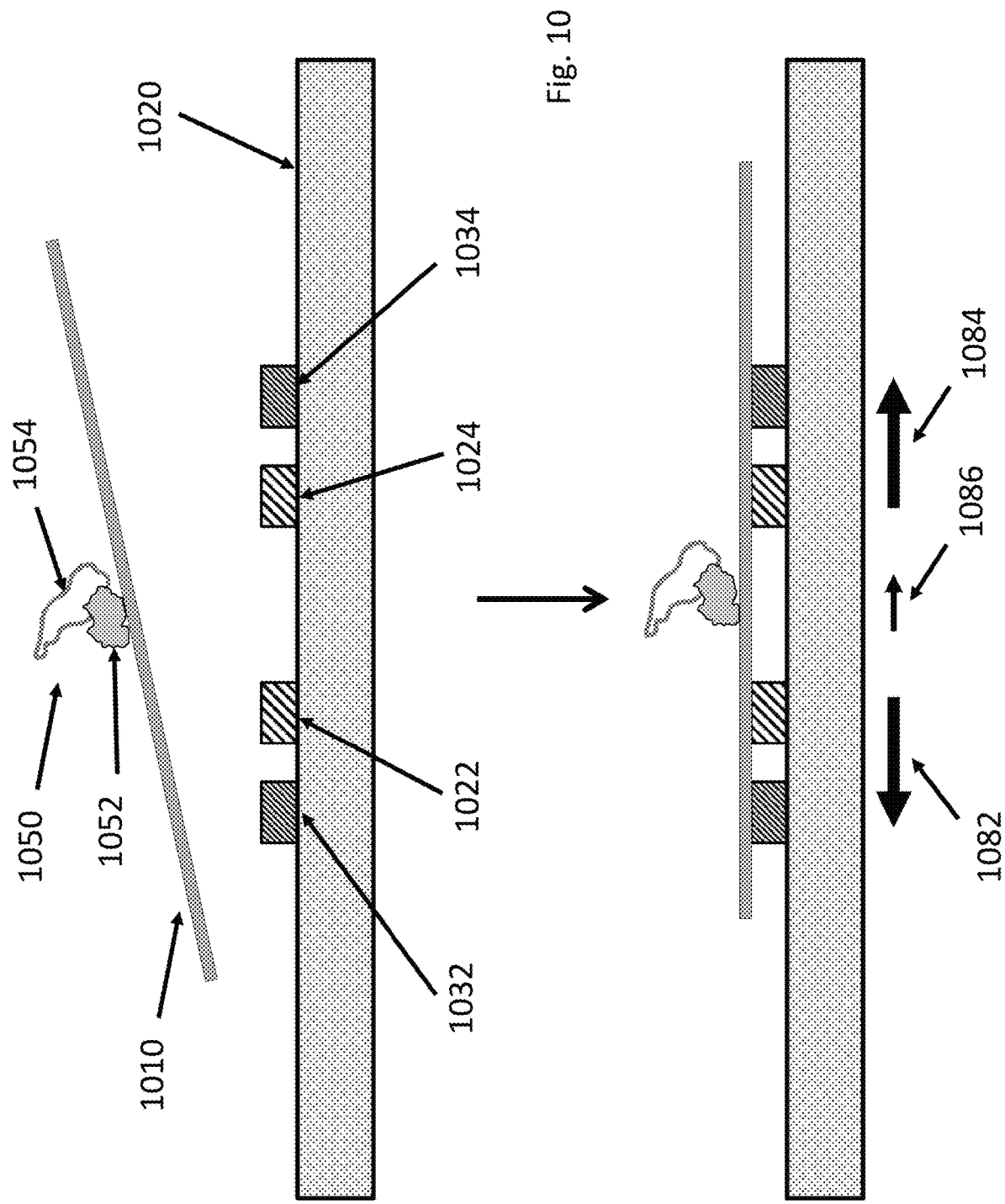
FIG. 10 shows a method in which the polymerase enzyme complex (or polymerase enzyme without associated template) is deposited onto the chip.

FIG. 10 shows a method similar to that shown in FIG. 9, but in which the polymerase enzyme complex (or polymerase enzyme without associated template) is deposited onto the chip. While the methods are described here with respect to an enzyme complex it is understood that the method can be used with a polymerase enzyme or other single molecule of interest. As described above, attaching the polymerase enzyme complex or the polymerase without associated template allows for purification of the mixture to preferentially select the nanotubes having a polymerase attached, allowing for a mixture enriched in nanotubes having a single polymerase complex attached.

The chip 1020 has an array of sets of electrodes. Each set of electrodes is arranged in a line across the chip. The distance between the first and last electrode in the line is less than the length of the nanotubes to be deposited. In FIG. 10, the chip 1020 has four electrodes in a line for each set. The inner electrodes 1022 and 1024 will become the source and drain of the nanoFET that is formed. The outer electrodes 1032 and 1034 are used to provide a field for attracting, aligning, and depositing the carbon nanotube 1010 having polymerase enzyme complex 1050 from solution. The polymerase enzyme complex 650 has polymerase enzyme 1052 and template 1054. In some cases, the deposition can be carried out using only two electrodes per set, in which these electrodes are used both for deposition of the nanotube, and also to act as source and drain for the nanoFET. An advantage of using 4 electrodes per set is that the outer electrodes 1032 and 1034 can be prepared for providing the deposition electric field, while the inner electrodes 1022 and 1024 can be prepared for optimal detection of small current changes as source and drain for the carbon nanotube nanoFET. For example, the outer electrodes 1032 and 1034 are made with the materials and at the dimensions for providing a higher voltage and higher current for deposition. The deposition electric field can be a DC field, an AC field, or a combination of an AC and DC field. The application of an AC field allows for the use of dielectrophoretic forces for attracting, aligning, and depositing the carbon nanotubes with attached polymerase enzyme complex.

In some cases, after the deposition of the nanotube in FIG. 10 is completed, conductive material is selectively deposited over the source and drain electrodes to provide a more robust electrical connection to the nanotube. Typically, with the enzyme present on the nanotube, this deposition is carried out in solution, using, for example, electrodeposition under mild conditions. In some cases, the outer electrodes can also be used in the nanoFET detection, for example, providing a voltage across the outer electrodes 1032 and 1034, and measuring a voltage drop across the inner electrodes 1022 and 1024 for enhanced nanoFET detection. In some cases, the outer electrodes 1032 and 1034 are kept at the same potential as the inner electrodes 1022 and 1024 during measurement. In some cases, the nanotube is selectively cleaved between the inner and outer electrodes to electronically isolate the inner from the outer electrodes for nanoFET detection.

One attractive approach of the invention is one in which the polymerase complex-nanotubes are dynamically sampled during deposition. For example, a polymerase complex nanotube is attracted down and captured on a source and drain, and while it is held there, a measurement across the source and drain will determine whether the polymerase is undergoing sequencing. If it is not, the potential is changed, e.g. across electrodes 1032 and 1034 to release the nanotube with bound polymerase complex, making room for another nanotube-polymerase complex to be captured by the set of electrodes. This process is repeated until an actively sequencing complex is detected, after which sequencing information is continued to be obtained.

This reversible approach can also be used to select for polymerase complexes having templates of interest. For example, the capture is carried out as described above, for example on a library in which some polymerase-template complexes in solution have a template with a sequence of interest, and some polymerase complexes have template with a sequence that is not of interest. After capture of a nanotube with attached polymerase complex, and an initial sequence is determined. If it is found that the sequence belongs to a region of the nucleic acid that is not of interest, the capture voltage adjusted to release the nanotube, making room for the capture of another polymerase complex that may have a desired nucleic acid region. This process is repeated until a template having the desired sequence is found, at which time the sequencing of that template is completed.

In order to carry out this method, we have determined that in some cases it is desirable to have a relatively high voltage drop between the one outer capture electrode 1032 and the source electrode 1022 and between the other capture electrode 1034 and the drain electrode 1024, but at the same time applying only a small voltage drop across the source 1022 and the drain 1024. This approach is illustrated in FIG. 10 in which arrows 1082 and 1084 represent the relatively large electric field between electrodes 1022 and 1032 and between electrodes 1024 and 1034 respectively, and arrow 1086 represents the relatively small electric field between nanoFET source and drain electrodes 1022 and 1024. In some cases, the potentials are applied in this manner such that outer electrode 1032 and 1034 are at the same potential, while a relatively large drop is applied between inner and outer electrodes (1022-1032, 1024-1034) and a relatively small drop is simultaneously applied between inner electrodes (1022-1024), which voltage drop that is for nanoFET measurements carrying out nanoFET measurements.

Figure 11:
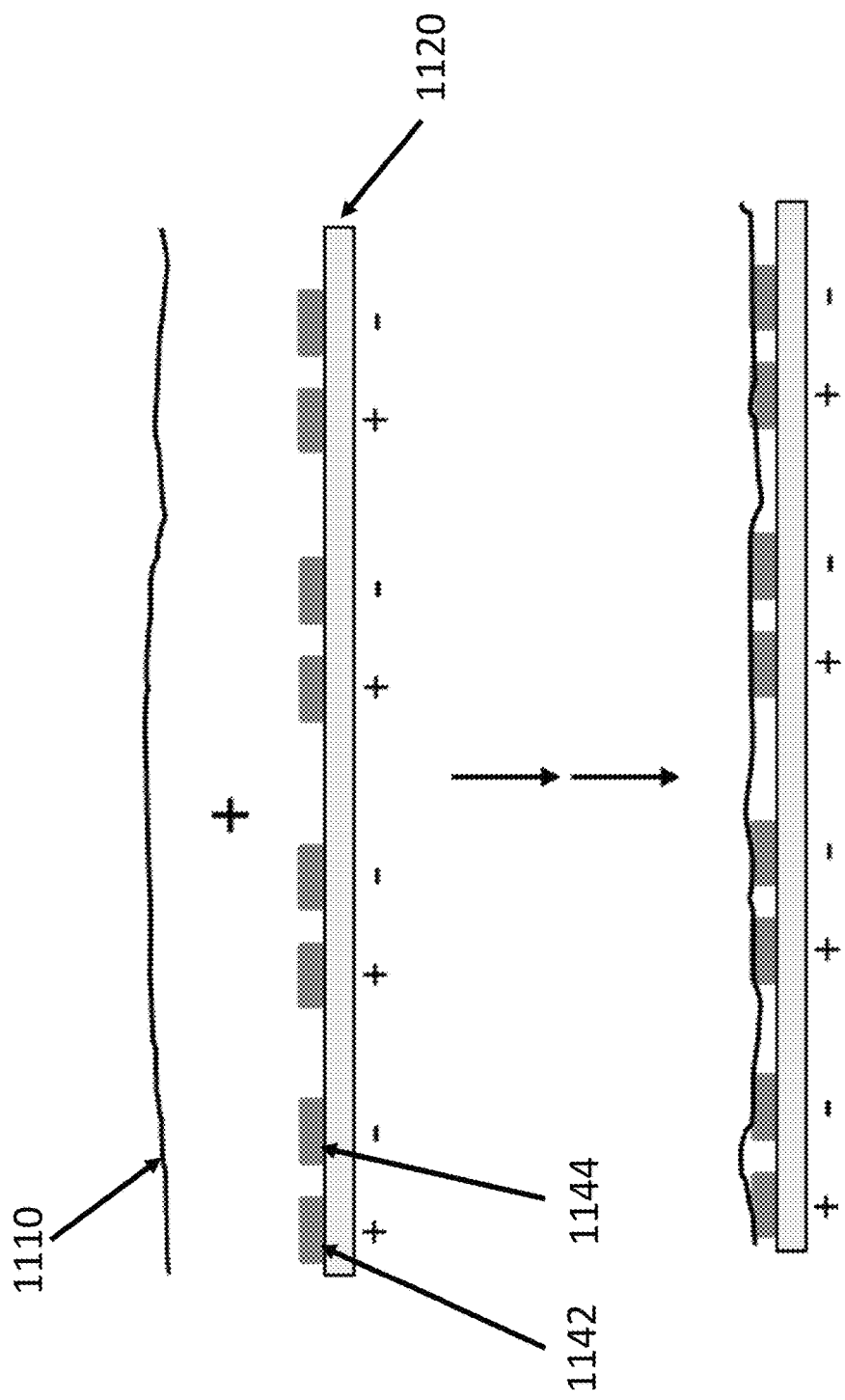
FIG. 11 provides an approach in which a number of source-drain sets are arranged in a line across the surface of the chip to electrically deposit a nanotube.

FIG. 11 provides an approach in which a number of source-drain sets 1142-1144 are arranged in a line across the surface of the chip 1120. Here, each set of electrodes is a pair of electrodes, however, the number of electrodes per set for attracting, aligning, and depositing the carbon nanotubes can be any suitable number, for example 3, 4, 5, 6, 7 or 8. Here, a solution of nanotubes 1110, extending over multiple source-drain pairs is added to the chip. The length of the nanotubes in solution is selected such that the nanotube extends across multiple source drain pairs. A voltage drop is provided across each of the source-drain pairs 1142-1144. The nanotubes are attracted, aligned, and deposited across multiple source-drain pairs. The set of source-drain pairs acts together to attract the nanotubes, and because there are a number of source-drain pairs, the voltage across any pair can be relatively low. The number of sets of electrodes, each including a source-drain pair can be, for example, 2, 3, 4, 5, 6, 7, 8, 9 10, 11, 12 or more sets.

Subsequent to deposition, conductive material is typically deposited selectively onto the source electrodes and drain electrodes as described herein to reduce contact resistance and provide a robust electrical connection between the electrodes and nanotube for each nanoFET. In some cases, the nanotube is selectively cleaved between each set of electrodes to further electrically isolate the nanoFETs from each other.

Increased Debye Screening Length

As discussed herein, the nanotube tends to be effective at detecting ionic changes within the Debye screening length, but beyond the Debye screening length, ionic changes are not detected. In some cases, it is useful to provide additives to the sequencing mixture that have the effect of increasing the Debye screening length to ensure the detection of the conductivity labels on the nucleotide analogs. In some cases, these additives are referred to as crowding agents. These crowding agents displace water and ions in solution. Suitable crowding agents are polar, non-ionic compounds. In some cases crowding agents are non-ionic polymeric compounds. Suitable compounds include non-ionic glucose polymers including Ficoll, for example Ficol 70. Other suitable crowding agents include polyethylene glycol (PEG), dextran, or proteins such as ovalbumin or hemoglobin.

In alternative embodiments, the concentration of monovalent and divalent (and polyvalent) ions is reduced and the systems ionic strength is supplemented with zwitterionic salts whose overall charge is zero or near zero. These salts can assist with the solubility of key components of the system while contributing only minimally to the charge screening. In some cases, a zwitterionic salt permits a reduction in monovalent salt concentration of 10%, 20%, 30%, 50%, 80%, or more over what would be required without the zwitterionic salts. The resulting increase in the Debye screening length can directly result in increased sensitivity of the FET sensor to charges that are not directly contacting the FET detector surface. In some embodiments, zwitterionic salts make up more than 30%, more than 40%, more than 50%, more than 60%, more than 70%, more than 80%, or more than 90% of the ions in the sequencing reaction mixture.

Surface Treatment of the nanoFET Gate

In some aspects of the invention, the surface of the nanotube is modified to enhance the detection capabilities of the nanoFET. The surface treatments can provide an insulting layer, or can extend the Debye screening length. The surface treatments can be used to enhance sensitivity in certain regions of the nanotube and/or to decrease sensitivity in certain regions of the nanotube. In some cases both sensitivity enhancing and sensitivity decreasing treatments can be used to improve the relative sensitivity of the nanotube in a region of interest, for example near the exit region of the polymerase, thereby improving the signal to noise ratio of the measurement. Polymers can be used to bind to and coat the polymer surface. Suitable polymers include the polymer binding agents described above for attaching polymerase enzymes to the nanotubes. The surface treatment agents can be non-ionic or ionic materials. They can include negatively charged species, positively charges species, or combinations of both positively charged and negatively charges species. They can include aromatic units such as pyrene which tend to bind to the nanotube surfaces by hydrophobic interactions. Suitable surface treatment agents include nonionic and ionic surfactants that are well known in the art. In some cases, a sensitivity decreasing surface treatment is applied over the majority of the nanotube, and a region of the nanotube near the polymerase is left exposed, thereby providing enhanced sensitivity in a region of interest. Copolymers such as block copolymers can be used. Suitable co-polymers includes, for example, ((PEG)-pyrene)$_n$ having alternating pyrene and ethylene glycol units. The characteristics of this polymer can be tuned by varying the length of the PEG units, longer PEG regions producing a more hydrophilic coating. Small molecule such as (PEG)-pyrene can also be used in which the average number of PEG units is from about 20 to about 120.

Other aspects of the invention that increase the sensitivity of a FET sensor include decorating the surface of the FET device with conductive polymers that extend the zone of sensitivity to the charge of interest. This allows for detecting a charge that is further away from the gate of the nanoFET that without having the conductive polymer present. Materials that are useful include polymers with high densities of double and single bonds in resonance. These include, for example, polyacetylene and polythiophene. In some cases, these polymers are doped, for example to become n-type or p-type semiconductors. Polymer chains of redox moieties such as ferrocene can also serve as molecular conductors. When the nanowire is decorated with such current-carrying molecules, the polarization caused by the charge of interest can be communicated though the conductor to the nanowire detector onto which it is deposited.

In some embodiments of this method, the conductive polymers are not covalently attached, but rather allowed to associate non-covalently via hydrophobic interactions with the gate of the nanoFET, e.g. nanowire or nanotube. In some cases the conductive polymer has side groups that promote the water solubility of the chain. In some cases the conductive polymer molecules have a dual character, containing regions that are non-soluble and regions that are soluble, for example, block copolymers. The non-soluble portions will tend to associate with a hydrophobic nanowire surface while the soluble portions will explore the space around the charge of interest. Although described as an alternative to bringing the charged molecule closer to a nanowire sensor, this strategy can also be used in combination with a strategy that increases the proximity of the charged molecule to further increase the sensitivity.

Reference Nanowire

Another aspect of the invention provides for positioning a reference nanowire immediately adjacent to the nanowire bound to the polymerase. Some noise processes will be correlated between the two nanowires. Thus, a higher signal-to-noise ratio can be obtained by using the difference signal or cross-correlation signal between these two wires than can be obtained with a single nanowire or nanotube. For example, fluctuations caused by the gyration of a long strand of DNA being sequenced can be expected to have some common mode between two adjacent electrodes, and can thus be mitigated by the presence of the reference. For example, if a long strand of DNA experiences large fluctuations in position during a sequencing run, the proximity of large quantities within 100 nm or even 1000 nm can lead to a temporary increase in the rate of diffusive contacts between the DNA strand and the nanowire. These increases will read out at long time-scales as an upward fluctuation in the current. If two nanowires are very close together, they would share this increase—it would happen simultaneously for both wires. Thus where two very closely spaced wires are used and the polymerase is attached to one but not the other, the difference in current between the two wires will have less noise due to DNA template movements as compared the corresponding measurement using just one electrode. In some cases the measurement nanowire and the reference nanowire are between 4 nm to 30 nm apart. In some cases the measurement nanowire and the reference nanowire are between 5 nm to 20 nm apart. In some cases the measurement nanowire and reference nanowire are parallel to one another.

Alternative Sequencing Modes

Figure 12:
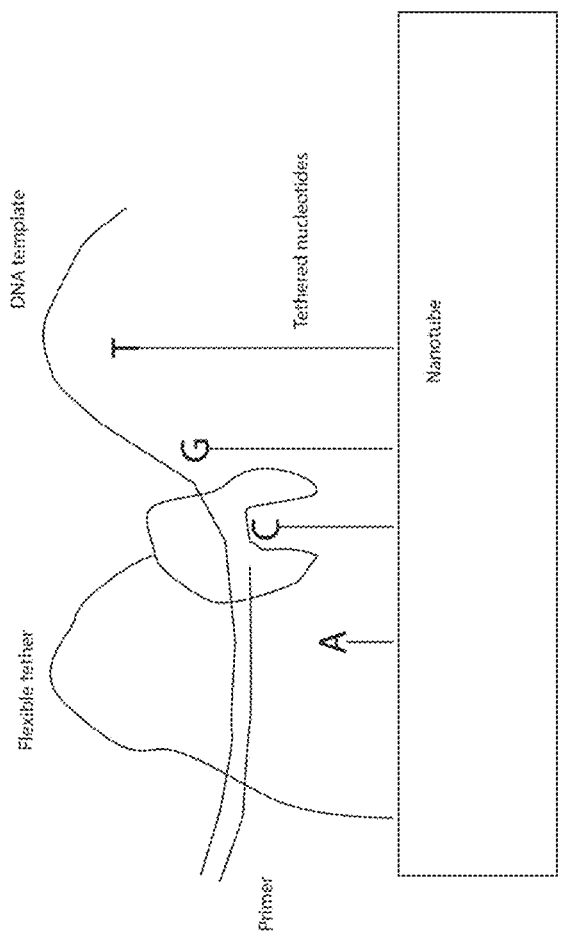
FIG. 12 shows a sequencing modes of the invention in which unincorporatable nucleotides are bound to the surface of the nanowire with different length linkers for each base.

In alternative sequencing modes of the invention, unincorporatable (e.g. nonhydrolizable) nucleotides are bound to the surface of the nanowire with different length linkers for each base. A schematic representation of such an embodiment is provided in FIG. 12. A low concentration of free native nucleotide is provided in solution that allows the system to slowly move forward. While the polymerase is waiting for each next incorporatable base, it will repeatedly and unproductively sample against the tethered nucleotides producing a signal comprising one or more cognate sampling events. Since the voltage or current will be affected by the length of the tether used for each base, the signal will be different for each nonhydrolizable nucleotide during the sampling events. Typically, multiple sampling events are averaged to calculate a signal that indicates which nonhydrolizable nucleotide is being sampled. Other methods for sequencing using polymerase sampling are also described in U.S. Pat. No. 8,530,164, which is incorporated herein by reference in its entirety.

NanoFETs within Recessed Regions

Some aspects of the invention provide arrays of nanoFETs in which each of the nanoFETs is within a well or a recessed region on the substrate. In some cases the nanoFETs are in regions recessed between about 5 nm and about 300 nm into the substrate. In some cases the nanoFETs are in regions recessed between 10 nm and about 50 nm into the substrate. In some cases, the nanoFETs are recessed about 10 nm, 20 nm, 30 nm, 40 nm, 50 nm, 80 nm, 100 nm, 200 nm or 300 nm into the substrate. In some cases the recessed regions can be wells that extend down into the substrate. The wells can alternatively extend into the substrate from the side (e.g. into a vertical wall of the substrate) or can extend into the substrate at any suitable angle. In some cases the recesses or wells are wider than they are deep, for example with a ratio of depth to width of about 1:2 to about 1:10, where depth is the direction of the recess. In some cases the recesses or wells are deeper than they are wide, for example with a ratio of depth to width from about 1.5:1 to about 5:1.

We have found that having the nanoFET within a nanoscale well of the appropriate dimensions provides unexpected benefits. Where the dimensions are appropriately chosen, the well tends to pull the nucleic acid associated with the polymerase away from the nanotube through entropic effects, resulting in less association of the nucleic acid with the nanotube. The nucleic acid molecules associated with the polymerase, including the template molecules and nascent strand molecules, prefer to maximize their entropy, and when the molecules are within a confined region, portions of the molecule that are able to will make their way out of the region where they have more conformational freedom. By constraining the volume, the nucleic acids will entropically extend away from the nanotube, and therefore be less likely to create background by interacting with the nanotube. The confined or recessed region can be a well, a slit or any other suitable shape. Where the confined region is a well, it can have a substantially circular profile (e.g. a cylindrical well). The well can have a larger diameter opening than the base, or can have a smaller diameter opening than the diameter of the base. Where the confined region is a well it is typically desirable that the width of the well is less than about 300 nm, less than about 200 nm, or less than about 100 nm.

Figure 13:
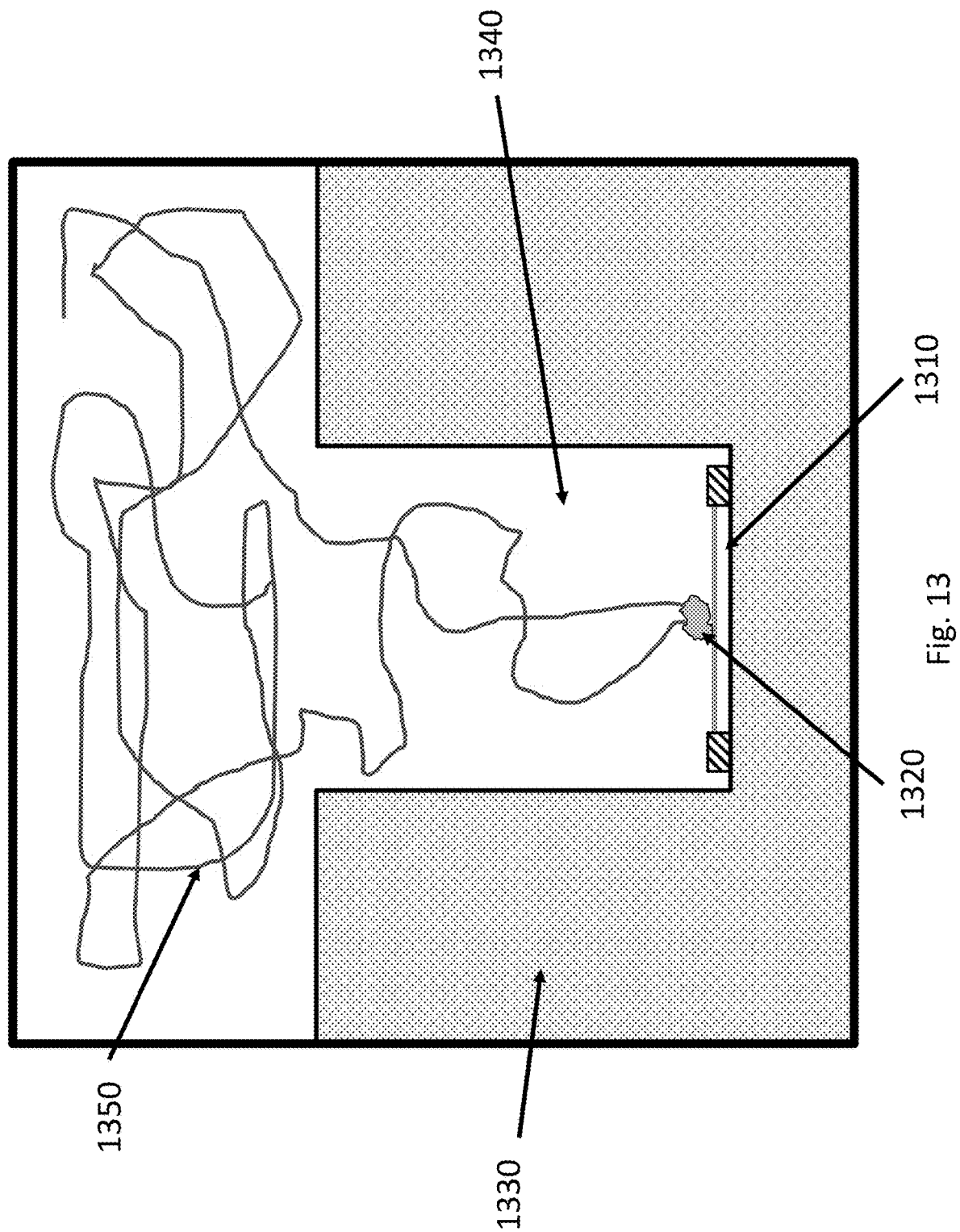
FIG. 13 shows a device having a constrained region to reduce the interaction of associated nucleic acid molecules with the nanotube nanoFET.

The use of a constrained region to reduce the interaction of associated nucleic acid molecules with the nanotube nanoFET is illustrated in FIG. 13. The nanoFET 1310 is disposed at the bottom of a constrained region 1340 which is formed in the substrate 1330. The nanoFET has bound to it a single polymerase enzyme 1320, the activity of which is monitored while nucleic acid synthesis is occurring. The nucleic acid molecules 1350 associated with the polymerase enzyme tend to extend out of the constrained volume due to entropic effects as described herein. The nucleic acid molecules can include the template nucleic acid and the nascent strand that is formed during the polymerase reaction. There is a reduction in interaction of the nucleic acid molecules with the nanotube nanoFET due to their tendency to extend out of the constrained region, reducing background noise.

In order to produce nanoFET devices in wells with such dimensions, it is sometimes desirable to utilize nanotubes having lengths less than bout 300 nm, e.g. in the 100 nm to 300 nm length range. Such nanotubes are known in the art. See for example, J. Chen, M. A. Hamon, H. Hu, Y. Chen, A. M. Rao, P. C. Eklund, R. C. Haddon, Science 1998, 282, 95 which is incorporated herein by reference for all purposes. Nanotubes in this size range are also available commercially, for example from NanoWerk and at NanoIntegris companies.

Figure 14:
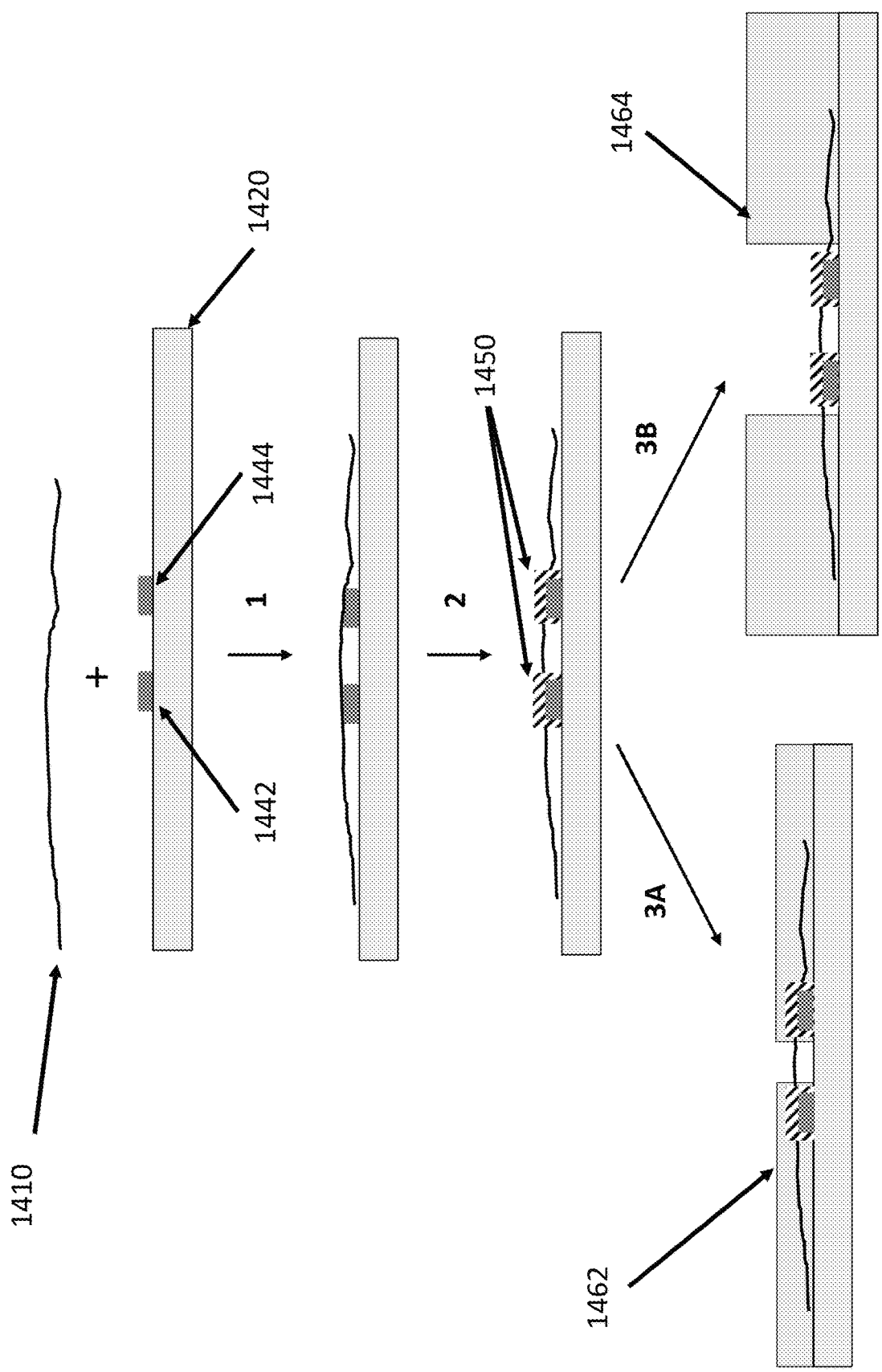
FIG. 14 provides approaches to forming nanoFETs in confined regions such as topologically constrained nanowells.

FIG. 14 provides approaches to forming nanoFETs in confined regions such as topologically constrained nanowells. In steps 1 and 2, a nanotube nanoFET is formed on the surface of a chip. Methods for forming these structures are provided herein and in the art. In the method shown in FIG. 14, in step 1, a nanotube is deposited onto a substrate 1420 having nanoscale electrodes 1442 and 1444. In step 2, a conductive material 1450 is deposited onto the nanoscale electrodes to lower contact resistance at the electrodes and to provide a robust electrical connection. In step 3, a confined region such as a nanowells is formed by selectively depositing a material onto the substrate whereby at least a portion if the nanoFET remains exposed. In FIG. 3A, a material 1462 is deposited onto the surface such that the material covers the nanoscale electrodes 1442 and 1444. This leaves only the carbon nanotube (or a portion of the carbon nanotube) exposed. This approach can not only provide a constrained volume as described herein, but also can be used to reduce background by limiting the portion of the nanotube that is exposed to the solution during measurement. In an alternative approach, in step 3B, material 1464 is deposited to produce a confined volume in which the nanoFET remains fully exposed. Here, the nanoFET, including its electrodes, will be completely exposed to the solution during the analysis. In some cases, as shown here, the material also covers and embeds the portion of the nanotube that extends beyond the nanoscale electrodes. In some approaches, an intervening process is used to remove the portions of the carbon nanotube extending beyond the nanoscale electrodes prior to deposition of the well-forming material. The well-forming material can be any suitable material, many of which are known in the art of semiconductor processing. The material is typically insulating but could be conductive or semiconducting in some cases. The material can be organic or inorganic. The material can be, for example a polymeric material, a glass, or a metal. The material can be, for example a metal oxide or metal nitride.

Figure 15:
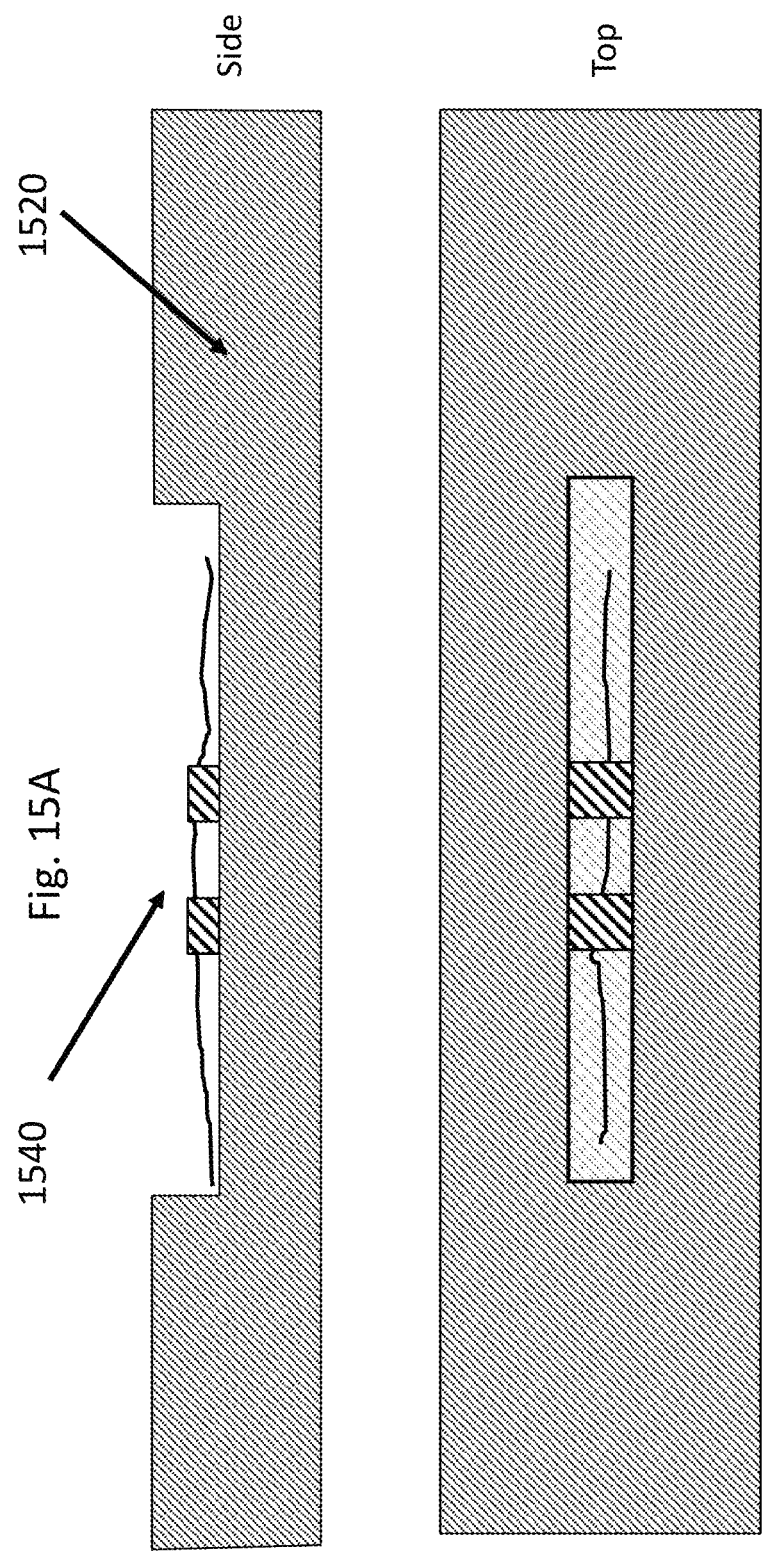
FIGS. 15A and 15B show a side and top view respectively of a portion of a chip having a nanoFET in a confined volume that is a trough or trench.

FIGS. 15A and 15B show a side and top view respectively of a portion of a chip 1520 having a nanoFET 1540 in a confined volume that is a trough or trench, long in the direction of the nanotube and narrower in the direction perpendicular to the nanotube. In some cases, the chip is produced having such long narrow troughs with nanoscale electrodes within them. When the nanotubes are subsequently deposited, the size and aspect ratio of the trough favors deposition of nanotubes in the desired orientation, extending across the nanoscale electrodes. After deposition of carbon nanotubes on the nanoscale electrodes, a conductive material can be selectively deposited onto the electrodes to provide a robust attachment of the nanotubes. Structures such as that shown in FIG. 15B can alternatively be formed by the methods illustrated in FIG. 14 in which the trough is formed after formation of the nanoFET device. The methods described herein can also be combined with those approaches outlined in FIG. 6, for example where the polymerase is attached to the nanotube prior to deposition. The approaches that include a long, narrow trough are particularly useful where it is desired to use relatively long nanotubes (e.g. greater than 300 nm in length), yet where the desired length of the nanotube between the nanoscale electrodes is less than half, less than a third, or less than on quarter of the length of the average nanotube in the deposition solution. These trough structures can also be used in conjunction with approaches such as that shown in FIG. 11 in which there are multiple sets of nanoscale electrode pairs along a line (e.g. in a line down the long axis of the trough. This type of structure can be used with or without the use of electrically assisted loading.

For example, the long, narrow trough can have a long dimension between 200 nm and one micron, and the narrow dimension can be from 10 nm to about 100 nm. In some cases, the aspect ratio (length to width) of the trough is from about 4:1 to about 100:1. The depth of the trough is typically from about 20 nm to about 300 nm. Processes for making structures on the size scale of those described herein are provided, for example, in Lieber et al. Chem. Rev., 2016, 116 (1), pp 215-257 "Nano-Bioelectronics" and Jeong et al. J. Mater. Chem., 2011, 21, 14285-14290 "Patterned nano-sized gold dots within FET channel: from fabrication to alignment of single walled carbon nanotube networks" which are incorporated by reference for all purposes herein.

An approach to inhibit interaction between nucleic acid molecules associated with the polymerase and the nanotube is to use structural features, thus structurally biasing these molecules away from the surface. Long chain molecules experience reduced entropy when confined in a small space, and when such a molecule traverses a boundary between a confined and non-confined space the difference in entropy can lead to a free-energy gradient that produces a measurable tension in the molecule. Therefore, placing the sensing region in a recess small enough to reduce entropy of the DNA chain will not only physically displace most of the DNA molecule away just by a barrier effect, the presence of the small recess will also pull those parts of the molecule that are geometrically constrained to still reside inside constrained region and bias them away from the active sensing region of the CN-FET which is much smaller than the recessed zone. Above, we describe the use of wells and trenches or troughs as confined regions. In some cases structures other than wells and trenches can be used as long as they provide the entropic gradient required to pull the nucleic acids away from the nanoFETs.

Figure 16:
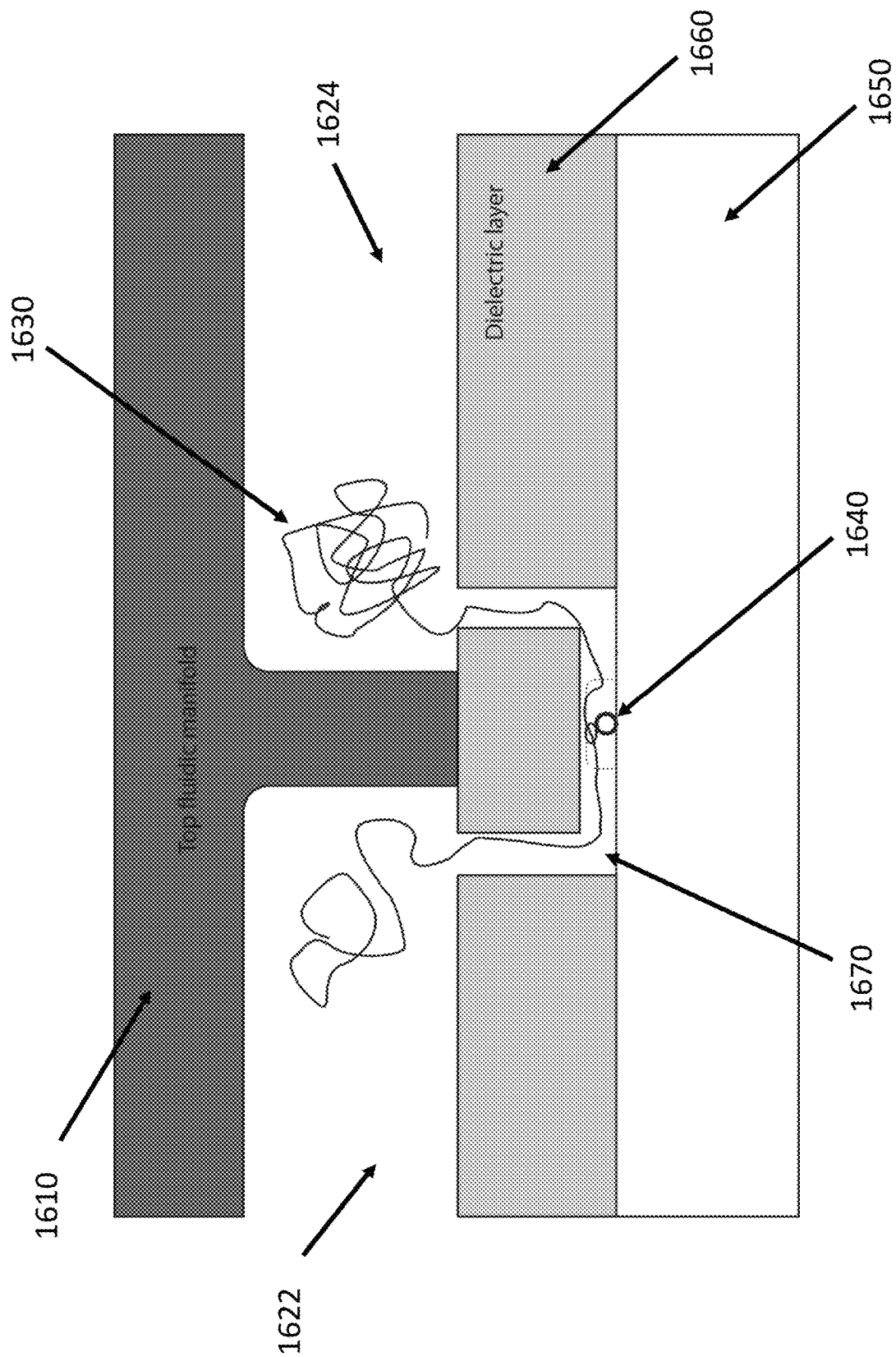
FIG. 16 shows a device in which the constrained region is a region between two fluid reservoirs into which the nucleic acids associated with the polymerase will move due to the volume constraints in the vicinity of the nanotube nanoFET.

In some cases, the constrained region is a region between two fluid reservoirs into which the nucleic acids associated with the polymerase will move due to the volume constraints in the vicinity of the nanotube nanoFET. FIG. 16 shows an embodiment of this approach. FIG. 16 shows a cross section of a chip comprising a substrate 1650. On the substrate is a dielectric layer 1660. The dielectric layer 1660 has an array of features that produce a constrained region 1670 in which the nanoFET with attached polymerase enzyme 1640 is disposed. The constrained region 1670 is open to both cis reservoir 1622 and trans reservoir 1624. There is a top fluid manifold 1610 above the dielectric layer that provides a separation between the cis and trans reservoirs. The nanoFET with attached polymerase enzyme 1640 is disposed within the constrained region 1670 such that the nucleic acids associated with the polymerase extend up into either one or both of the cis reservoir 1622 and trans reservoir 1624. For example, in some cases, the template nucleic acid will tend to extend into the cis reservoir 1622, and the nascent strand nucleic acid will tend to extend into the trans region 1624 as it is produced. As described above for the simpler well or trough constrained regions, here, the nucleic acids associated with the polymerase 1630 tend to work their way out of the constrained regions, away from the nanoFET, resulting in a more reliable signal due to reduction in the background from interactions of the nucleic acids with the nanotube nanoFET.

Capacitive Filters for Improving Signal to Noise

In one aspect, the invention provides for improving the signal to noise of a device comprising an array on nanoFETs by including capacitive filters. The capacitive filters are provided as structures in solution above each nanoFET. For example, a capacitive filter can be a layer of conductive material that is above the nanoFET, and is typically electrically and/or physically connected to the substrate on which the nanoFET is disposed. The conductive material can be, for example a planar electrode that is typically above the nanoFET with its planar surface parallel to the substrate. The dimensions of the planar electrode are typically large relative to the area of the nanoFET. In some cases, the area of the electrode is 10 times, 100 times or 100 times larger than the area of the nanoFET. The area of the electrode can be, for example, between 4 nm squared to 500 nm squared, or from about 10 nm squared to about 100 nm squared.

In large CMOS arrays only a small fraction of the total time of one sampling cycle can be allocated to each individual device. This is the case even when there is a separate amplifier for each row, since a thousand or more devices may be served by just one amplifier and ADC. This means that the duty cycle of each device may be 0.001 or lower. In current or voltage sampling applications such as are used with addressing nanoFETs, the noise is generally inversely related the square root of the total sampling time. So, if the duration of a sample is increased 4-fold, the noise level will be cut in half. Therefore the noise levels at a duty cycle of 0.001 could be 30 times higher than if the amplifier were In optical sensing applications, this issue can be managed by creating a floating diffusion that acts as a reservoir to store charge from incoming photons while the device waits for readout, thus escaping this scaling rule. Ironically, in devices with a very high intrinsic signal level, such as nanoFETs, it is difficult to use this approach because the amount of charge produced during one cycle can be very large—too large for the same kind of architecture used in light-sensing applications.

This invention provides a solution to this problem. The solution is to use an RC electronic filter which acts as a charge reservoir and "stores" charges between sampling events. This RC electronic filter can shift the noise scaling curve, but requires a relatively large capacitor to create longer RC time constants. There is limited real-estate within the chip itself for constructing this capacitor structure due to the large demands of the active electronics. The invention provides for introducing these capacitive structures towards the bulk solution above the chip rather than in the substrate of the chip itself. This solution is enhanced by the fact that there is a large reservoir of conductive solution that can act as an alternate ground-plane. Thus, the invention provides relatively large-area structures placed vertically above the nanoFET devices. With appropriate selection of materials, the electrical double layer can be made non-conductive, and a relatively large capacitor area can be created with either patterned or rough side-walls. For this invention, the fluid is in-effect a self-patterning counter-electrode to the nanoFET array and provides a uniform, large area capacitor layer. These structures provide for nanoFET arrays having higher signal to noise than devices without the capacitive structures.

NanoFET Arrays

Methods for making and addressing nanoFETs including nanoFETs comprising nanowires are known in the art. See, for example, Choi et al. "Single-Molecule Lysozyme Dynamics Monitored by an Electronic Circuit" Science 335, 319 (2012), and Patolsky et al., "Electrical Detection of Viruses", PNAS, 101(39), 14017, 2004 which are incorporated herein by reference in their entirety for all purposes.

The polymerase complex may be positioned relative to the nanoscale wire to cause a detectable change in the nanoscale wire. In some cases, the polymerase complex may be positioned within about 100 nm of the nanoscale wire, within about 75 nm of the nano scale wire, within about 50 nm of the nanoscale wire, within about 20 nm of the nanoscale wire, within about 15 nm of the nanoscale wire, or within about 10 nm of the nanoscale wire. The actual proximity can be determined by those of ordinary skill in the art. In some cases, the polymerase complex is positioned less than about 5 nm from the nanoscale wire. In other cases, the polymerase complex is positioned within about 4 nm, within about 3 nm, within about 2 nm, or within about 1 nm of the nanoscale wire.

In some embodiments, the polymerase complex is fastened to or directly bonded (e.g., covalently) to the nanowire (nanoscale wire) or gate, e.g., as further described herein. However, in other embodiments, the polymerase complex is not directly bonded to the nanoscale wire, but is otherwise immobilized relative to the nanowire, i.e., the polymerase complex is indirectly immobilized relative to the nanowire. For instance, the polymerase complex may be attached to the nanowire through a linker, i.e., a species (or plurality of species) to which the polymerase complex and the nanoscale wire are each immobilized relative thereto, e.g., covalently or non-covalently bound to. As an example, a linker may be directly bonded to the nanoscale wire, and the polymerase complex may be directly bonded to the linker, or the polymerase complex may not be directly bonded to the linker, but immobilized relative to the linker, e.g., through the use of non-covalent bonds such as hydrogen bonding (e.g., as in complementary nucleic acid-nucleic acid interactions), hydrophobic interactions (e.g., between hydrocarbon chains), entropic interactions, or the like. The linker may or may not be directly bonded (e.g., covalently) to the nanoscale wire.

Many nanowires as used in accordance with the present invention are individual nanowires. As used herein, "individual nanowire" means a nanowire free of contact with another nanowire (but not excluding contact of a type that may be desired between individual nanowires, e.g., as in a crossbar array). For example, an "individual" or a "free-standing" article may, at some point in its life, not be attached to another article, for example, with another nanowire, or the to free-standing article may be in solution. An "individual" or a "free-standing" article is one that can be (but need not be) removed from the location where it is made, as an individual article, and transported to a different location and combined with different components to make a functional device such as those described herein and those that would be contemplated by those of ordinary skill in the art upon reading this disclosure.

In another set of embodiments, the nanowire (or other nanostructured material) may include additional materials, such as semiconductor materials, dopants, organic compounds, inorganic compounds, etc. The following are non-limiting examples of materials that may be used as dopants within the nanowire. The dopant may be an elemental semiconductor, for example, silicon, germanium, tin, selenium, tellurium, boron, diamond, or phosphorous. The dopant may also be a solid solution of various elemental semiconductors. Examples include a mixture of boron and carbon, a mixture of boron and P(BP6), a mixture of boron and silicon, a mixture of silicon and carbon, a mixture of silicon and germanium, a mixture of silicon and tin, a mixture of germanium and tin, etc. In some embodiments, the dopant may include mixtures of Group IV elements, for example, a mixture of silicon and carbon, or a mixture of silicon and germanium. In other embodiments, the dopant may include mixtures of Group III and Group V elements, for example, BN, BP, BAs, AlN, AlP, AlAs, AlSb, GaN, GaP, GaAs, GaSb, InN, InP, InAs, or InSb. Mixtures of these combinations may also be used, for example, a mixture of BN/BP/BAs, or BN/AlP. In other embodiments, the dopants may include mixtures of Group III and Group V elements. For example, the mixtures may include AlGaN, GaPAs, InPAs, GaInN, AlGaInN, GaInAsP, or the like. In other embodiments, the dopants may also include mixtures of Group II and Group VI elements. For example, the dopant may include mixtures of ZnO, ZnS, ZnSe, ZnTe, CdS, CdSe, CdTe, HgS, HgSe, HgTe, BeS, BeSe, BeTe, MgS, MgSe, or the like. Alloys or mixtures of these dopants are also be possible, to for example, ZnCd Se, or ZnSSe or the like. Additionally, mixtures of different groups of semiconductors may also be possible, for example, combinations of Group II-Group VI and Group III-Group V elements, such as (GaAs)x(ZnS)1-x. Other non-limiting examples of dopants may include mixtures of Group IV and Group VI elements, for example GeS, GeSe, GeTe, SnS, SnSe, SnTe, PbO, PbS, PbSe, PbTe, etc. Other dopant mixtures may include mixtures of Group I elements and Group VII elements, such as CuF, CuCl, CuBr, CuI, AgF, AgCl, AgBr, AgI, or the like. Other dopant mixtures may include different mixtures of these elements, such as BeSiN2, CaCN2, ZnGeP2, CdSnAs2, ZnSnSb2, CuGeP3, CuSi2P3, Si3N4, Ge3N4, Al2O3, (Al, Ga, In)2(S, Se, Te)3, Al2CO, (Cu, Ag)(Al, Ga, In, Tl, Fe)(S, Se, Te)2 or the like.

As a non-limiting example, a p-type dopant may be selected from Group III, and an n-type dopant may be selected from Group V. For instance, a p-type dopant may include at least one of B, Al and In, and an n-type dopant may include at least one of P, As and Sb. For Group III-Group V mixtures, a p-type dopant may be selected from Group II, including one or more of Mg, Zn, Cd and Hg, or Group IV, including one or more of C and Si. An n-type dopant may be selected from at least one of Si, Ge, Sn, S, Se and Te. It will be understood that the invention is not limited to these dopants, but may include other elements, alloys, or mixtures as well.

As used herein, the term "Group," with reference to the Periodic Table, is given its usual definition as understood by one of ordinary skill in the art. For instance, the Group II elements include Mg and Ca, as well as the Group II transition elements, such as Zn, Cd, and Hg. Similarly, the Group III elements include B, Al, Ga, In and Tl; the Group IV elements include C, Si, Ge, Sn, and Pb; the Group V elements include N, P, As, Sb and Bi; and the Group VI elements include O, S, Se, Te and Po. Combinations involving more than one element from each Group are also possible. For example, a Group II-VI material may include at least one element from Group II and at least one element from Group VI, e.g., ZnS, ZnSe, ZnSSe, ZnCdS, CdS, or CdSe. Similarly, a Group III-V material may include at least one element from Group III and at least one element from Group V, for example GaAs, GaP, GaAsP, InAs, InP, AlGaAs, or InAsP. Other dopants may also be included with these materials and combinations thereof, for example, transition metals such as Fe, Co, Te, Au, and the like. The nanoscale wire of the present invention may further include, in some cases, any organic or inorganic molecules. In some cases, the organic or inorganic molecules are polarizable and/or have multiple charge states.

In some embodiments, at least a portion of a nanowire may be a bulk-doped semiconductor. As used herein, a "bulk-doped" article (e.g. an article, or a section or region of an article) is an article for which a dopant is incorporated substantially throughout the crystalline lattice of the article. For example, some articles such as carbon nanotubes are typically doped after the base material is grown, and thus the dopant only extends a finite distance from the surface or exterior into the interior of the crystalline lattice. In some embodiments, a bulk-doped semiconductor may comprise two or more bulk-doped regions. Thus, as used herein to describe nanowires, "doped" refers to bulk-doped nanowires, and, accordingly, a "doped nanoscopic (or nanoscale) wire" is a bulk-doped nanowire. "Heavily doped" and "lightly doped" are terms the meanings of which are understood by those of ordinary skill in the art.

In certain embodiments, a carbon nanowire can be functionalized with a thin layer that results in an affinity to the labels that increases partitioning of the current modulating label in the detection layer. In examples above hydrophobicity of a nanotube can serve the purpose of providing an attractive force that can be used to recruit conductivity-modulating labels close to the nanowire, but other interactions can be used. Optionally, pi-stacking can be used. For example, molecules with lots of pi electrons such as certain fluorescent labels will have a high affinity for a carbon nanotube beyond just what is due to the hydrophobic interaction. Further, a nanowire can be coated with charged groups to increase affinity to the conductance labels on the anologs. Yet further, the surface charge can be modified to affect the partitioning of the label.

In one set of embodiments, the invention includes a nanoscale wire (or other nanostructured material) that is a single crystal. As used herein, a "single crystal" item (e.g., a semiconductor) is an item that has covalent bonding, ionic bonding, or a combination thereof throughout the item. Such a single-crystal item may include defects in the crystal.

In yet another set of embodiments, the nanoscale wire (or other nanostructured material) may comprise two or more regions having different compositions. Each region of the nanoscale wire may have any shape or dimension, and these can be the same or different between regions. For example, a region may have a smallest dimension of less than 1 micron, less than 100 nm, less than 10 nm, or less than 1 nm. In some cases, one or more regions may be a single monolayer of atoms (i.e., "delta-doping"). In certain cases, the region may be less than a single monolayer thick (for example, if some of the atoms within the monolayer are absent).

In still another set of embodiments, a nanoscale wire may be positioned proximate the surface of a substrate, i.e., the nanoscale wire may be positioned within about 50 nm, about 25 nm, about 10 nm, or about 5 nm of the substrate. In some cases, the proximate nanoscale wire may contact at least a portion of the substrate. In one embodiment, the substrate comprises a semiconductor and/or a metal. Non-limiting examples include Si, Ge, GaAs, etc. Other suitable semiconductors and/or metals are to described above with reference to nano scale wires. In certain embodiments, the substrate may comprise a nonmetal/nonsemiconductor material, for example, a glass, a plastic or a polymer, a gel, a thin film, etc. Non-limiting examples of suitable polymers that may form or be included in the substrate include polyethylene, polypropylene, poly(ethylene terephthalate), polydimethylsiloxane, or the like.

A nanowire, nanoscopic wire or nanoscale wire is generally a wire, that at any point along its length, has at least one cross-sectional dimension and, in some embodiments, two orthogonal cross-sectional dimensions less than about 200 nm, less than about 150 nm, less than about 100 nm, less than about 70, less than about 50 nm, less than about 20 nm, less than about 10 nm, or less than about 5 nm. In other embodiments, the cross-sectional dimension can be less than 2 nm or 1 nm. In one set of embodiments, the nanoscale wire has at least one cross-sectional dimension ranging from 0.5 nm to 100 nm or 200 nm. In some cases, the nanoscale wire is electrically conductive. Where nanoscale wires are described having, for example, a core and an outer region, the above dimensions generally relate to those of the core. The cross-section of a nanoscopic wire may be of any arbitrary shape, including, but not limited to, circular, square, rectangular, annular, polygonal, or elliptical, and may be a regular or an irregular shape. The nanoscale wire may be solid or hollow. A non-limiting list of examples of materials to from which nanoscale wires of the invention can be made appears below. Any nanoscale wire can be used in any of the embodiments described herein, including carbon nanotubes, molecular wires (i.e., wires formed of a single molecule), nanorods, nanowires, nanowhiskers, organic or inorganic conductive or semiconducting polymers, and the like, unless otherwise specified. Other conductive or semiconducting elements that may not be molecular wires, but are of various small nanoscopic-scale dimensions, can also be used in some instances, e.g. inorganic structures such as main group and metal atom-based wire-like silicon, transition metal-containing wires, gallium arsenide, gallium nitride, indium phosphide, germanium, cadmium selenide, etc.

A wide variety of these and other nanoscale wires can be grown on and/or applied to surfaces in patterns useful for electronic devices in a manner similar to techniques described herein involving the specific nanoscale wires used as examples, without undue experimentation. The nanoscale wires, in some cases, may be formed having dimensions of at least about 1 micron, at least about 3 microns, at least about 5 microns, or at least about 10 microns or about 20 microns in length, and can be less than about 100 nm, less than about 80 nm, less than about 60 nm, less than about 40 nm, less than about 20 nm, less than about 10 nm, or less than about 5 nm in thickness (height and width). The nanoscale wires may have an aspect ratio (length to thickness) of greater than about 2:1, greater than about 3:1, greater than about 4:1, greater than about 5:1, greater than about 10:1, greater than about 25:1, greater than about 50:1, greater than about 75:1, greater than about 100:1, greater than about 150:1, greater than about 250:1, greater than about 500:1, greater than about 750:1, or greater than about 1000:1 or more in some cases. The nanowires of the invention include wires that are solid, and may be elongated in some cases. In some cases, a nanowire is an elongated semiconductor, i.e., a nanoscale semiconductor.

A "nanotube" (e.g. a carbon nanotube) is typically a nanoscopic wire that is hollow, or that has a hollowed-out core, including those nanotubes known to those of ordinary skill in the art. Nanotubes are used as one example of small wires for use in the invention and, in certain embodiments, devices of the invention include wires of scale commensurate with nanotubes. Examples of nanotubes that may be used in the present invention include, but are not limited to, single-walled nanotubes (SWNTs). Structurally, SWNTs are formed of a single graphene sheet rolled into a seamless tube. Depending on the diameter and helicity, SWNTs can behave as one-dimensional metals and/or semiconductors. Methods of manufacture of nanotubes, including SWNTs, and characterization are known. Methods of selective functionalization on the ends and/or sides of nanotubes also are known, and the present invention makes use of these capabilities for molecular electronics in certain embodiments. Multi-walled nanotubes are well known, and can be used as well.

Another aspect of the invention is a hidden-Markov model (HMM) data analysis method in which the voltage transitions are explained by a hidden state (the sequence) through a 10-base context-dependent allosteric lookup table which produces about 4,000,000 different voltage levels, but each base position is interrogated 10 times by the progressing polymerase, so the sequence can be resolved by looking at the complete set of voltage transitions. One novel aspect of this approach is the recognition that the kinetics being impacted by 10 bases of context likely means that the allosteric interactions will also be strongly influenced by 10 bases of context. These effects can be as strong as the analog structure impact on the observed voltage change—meaning that the same analog in the same polymerase in one context could produce a positive change while in another context it could produce a negative change. In certain embodiments, the same DNA is sequenced with different enzymes to help resolve singularities in the HMM model that mean that errors will always occur in the same contexts. Where the 10-base context table is different for different enzymes or for different analogs used with those enzymes, the systematic errors that would normally result from ambiguous 10-base stretches will be removed.

One or more of the analogs (e.g., via the conductance label, nucleobase, phosphate chain, sugar, other modification, or a combination thereof) can produce a positive change and the other analogs produce a negative change. For example, if two produce a positive change and two produce a negative change, only two amplitudes of voltage on either side of the quiescent state voltage would be required to discern the order of base incorporation into the nascent strand.

The nanoFET chips can also have other incorporated components. Since the devices can be made by semiconductor processing techniques, it is straightforward to include other components such as resistors, capacitors, amplifiers, memory circuits, A/D converters, logic circuits, and the like. The circuits can provide the functions of amplification, analog to digital conversion, signal processing, memory, and data output. By having components such as CMOS processors included in the device addresses the issue of monitoring multiple events simultaneously. Rather than having at least one pair of wires bringing signals out from the chip, the inclusion of these components allows for a multiplexed output or an addressable output such as used in a DRAM chip. Where the number of devices is large, there tends to be more of a demand for building in extra circuitry onto the chip. This allows for carrying out partial analysis on the chip in a way that can significantly reduce the need for the amount of electrical signals that have to go to and from the chip.

The electrodes used in the devices including the source and the drain can be made of any suitable conducting material. They are typically made of a conductive metal that is amenable to semiconductor processing. Metals include aluminum, silver, gold, and platinum. The electrodes are fabricated to be on the order of nanometers in at least one dimension, at least two dimensions, or three dimensions. The size of the electrode is dependent on various design parameters. When discussing the size of the electrodes in this application, we are generally referring to the portion of the electrode which is exposed to the fluid sequencing mixture. In many cases, the size of the conductive portions not in contact with the solution are made larger in size to increase conductivity.

Figure 17:
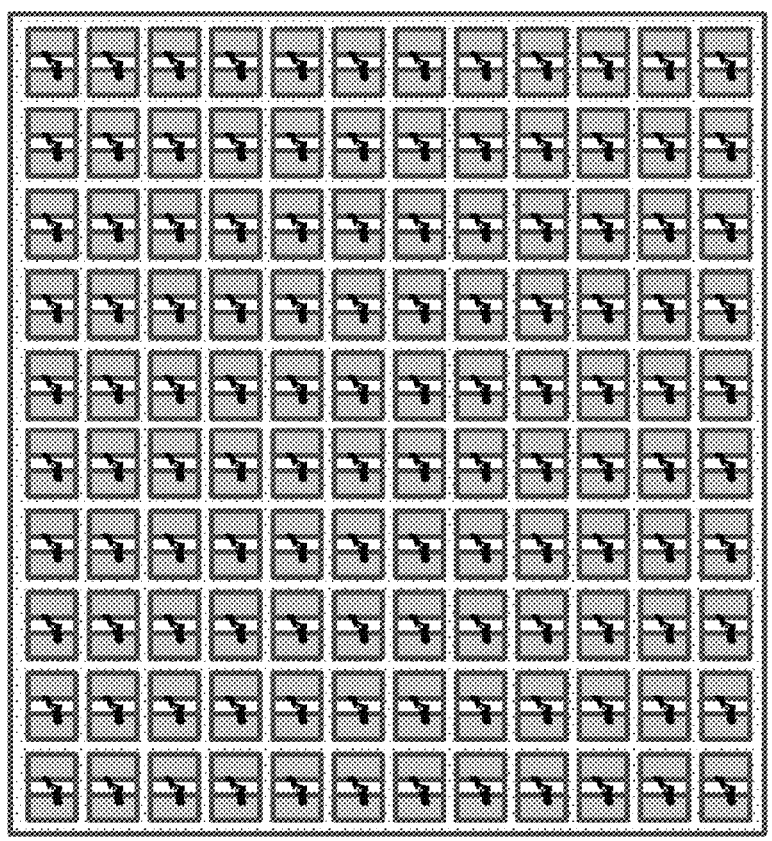
FIG. 17 illustrates an array of nanoFET devices in two dimensions on a chip.

FIG. 17 illustrates an array of nanoFET devices in two dimensions on a chip. A semiconductor surface can be patterned to produce an array of nanoFET devices. The interconnects to connect the nanoFETs to the electrical inputs and outputs can be provided by dropping through vias to lower layers. The electrical connections to the chip are typically made to the sides or to the bottom of the chip.

Conductivity Labels

The labels of the invention are moieties that can cause a change in the electric properties of the gate of a nanoFET, e.g. a nanowire or nanotube. The labels are referred to herein as conductance labels, conductivity labels, impedance labels and the like. It is understood by those of skill in the art that the electronic changes in the gate can be due to changes in the electric field surrounding the gate, or, for example, changes in the conductivity of the nanowire or nanotube. In some cases, the change at the gate can be due to the displacement of charges in solution that are surrounding the gate. Often, the electrical signal at the gate is measured by putting a voltage across the source and drain of the nanoFET, and monitoring the current through the gate. Any such change in electrical property can be used to detect a conductivity label. In some cases, the conductivity label comes into contact (possibly repeated contact) with the gate, and in other cases, the conductivity label comes within a distance of the nanotube such that its presence is detected by the gate. The conductivity labels are often charged species. They can be positively charged, negatively charged or have both negative and positive charge. In some cases, the label can cause an increase in conductivity at the gate, and in some cases, the label can case a decrease in conductivity at the gate. In some cases, then nanoFET can be considered an ion sensitive FET or ISFET. Conductivity labels can be charged species that are water soluble. The conductivity labels can have multiple charges, e.g. from about 2 to about 2,000 charges. The labels can comprise dendrimers or nanoparticles. Multiple labels can be employed, each having a different level of charge, in some cases, with some labels positively charged and some labels negatively charged.

In some cases, the labels can comprise moieties that interact with the nanotube surface, thereby displacing species such as ionic species from the nanotube surface.

The conductance label is selected such that when the nucleotide analog to which it is attached is within the active site of the enzyme, the label produces a change in conductivity of the nanowire to which the polymerase is attached or to which the polymerase enzyme is proximal. The change can be a positive change or a negative change, and where multiple conductance labels are used in a single reaction mixture, one subset may produce positive changes while another subset produces negative changes. Different types of conductance labels are contemplated for use with the methods provided herein. In general, conductance labels include conductance affecting groups, i.e., groups that enhance or diminish impedance or conductance of the composition, and are useful in applications where incorporation is detected by changes in impedance or conductance at or near the synthesis complex. Examples of conductance-impacting functional groups include, e.g., long alkane chains which optionally include solubility enhancing groups, such as amido substitutions; long polyethylene glycol chains; polysaccharides; particles, such as latex, silica, polystyrene, metal, semiconductor, or dendrimeric particles; branched polymers, such as branched alkanes, branched polysaccharides, branched aryl chains. Conductance labels may additionally or alternatively include electrochemical groups that detectably alter the charge of the molecule and may be detected or otherwise exploited for their electrochemical properties, such as their overall electric charge. For example, one may include highly charged groups as the functional group, like additional phosphate groups, sulfate group(s), amino acid groups or chains, e.g., polylysine, polyarginine, etc. Likewise, one may include redox active groups, such as redox active compounds, e.g., heme, or redox active enzymes. Other conductance labels may include, e.g., electrochemical labels, magnetic particles, beads, semiconductor nanocrystals or quantum dots, metal nanoparticles (e.g., gold, silver, platinum, cobalt, or the like), mass labels, e.g., particle or other large moieties. A wide variety of conductance labels are generally commercially available (See, e.g., the Molecular Probes Handbook, available at online at probes.invitrogen.com/handbook/), incorporated herein by reference. In some cases, nanoparticles are used as labels. For example, nanoparticles of metals, seimconductors, glasses, oxides, carbon, silicon, protein, polymers, ionic materials, can be used.

In some cases the conductivity labels comprise beads, for example beads comprising multiple nucleotides attached via their polyphosphate portion. Such analogs are described, for example in U.S. Pat. No. 8,367,813 which is incorporated by reference herein in its entirety for all purposes. The beads can be coated with charged functional groups, anionic, cationic, or a combination of anionic and cationic groups. The amount of charge on the bead can be controlled in order to control the electrical signal at the gate of the nanoFET. The beads can have any usable size range, for example, between about 2 nm and about 50 nm in size. The shapes of the beads can be spherical, elongated, or other effective shape for controlling the current at the gate of the nanoFET.

While the labels that interact with the gate are referred to conductivity labels, the measured signal can be from a change in any suitable electrical property of the nanoscale wire, such as voltage, current, conductivity, resistivity, inductance, impedance, electrical change, an electromagnetic change, etc. The signal may further include various aspects of the kinetics of the reaction, e.g., on/off rates, incorporation rates, and rates of conformational changes in the enzyme. Yet further, the kinetics can be influenced experimentally to enhance kinetic signals, e.g., by changing the ionic strength or types of ions present in the reaction mixture or the concentrations of various components, e.g., nucleotides, salts, etc., or the types/lengths of the linkers attaching the labels to the nucleotide analogs, where those changes impact the kinetics of the reaction. In yet further embodiments, enzymes can be used that have more distinct, and therefore more detectable, conformational changes. These and other methods of changing the kinetics of a reaction that can be used with the methods described herein are further described in the art, e.g., in U.S. Pat. Nos. 8,133,672, 8,986,930, 8,999,676, and U.S. Patent Publication No. 2014/0206550, all of which are incorporated herein by reference in their entireties.

Figure 18:
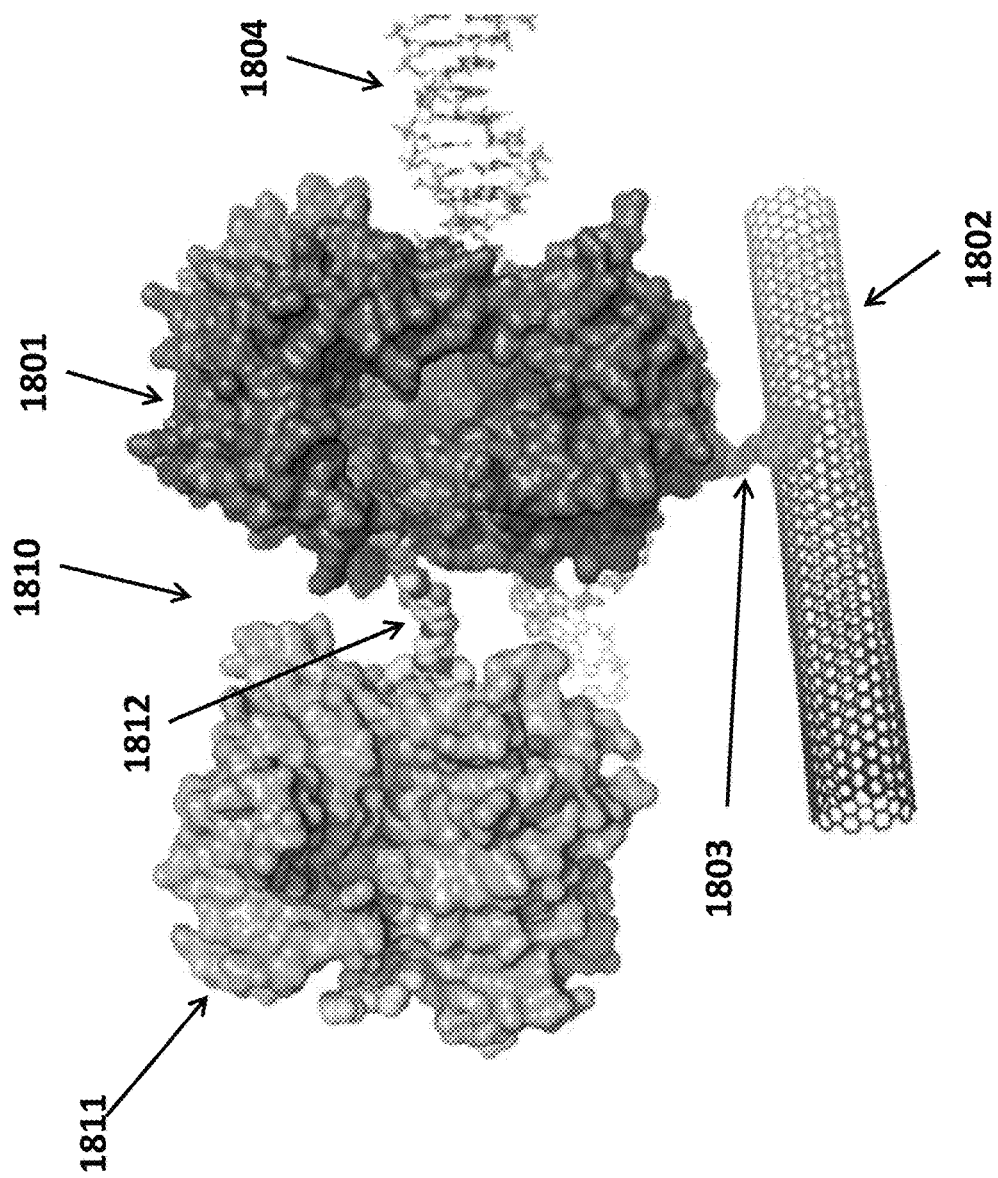
FIG. 18 shows an example of a nucleotide analog having a protein conductivity label having a size on the order of the polymerase enzyme.

As described herein, for a label to be detected at the gate of the nanoFET, it typically must be at least close enough to the nanowire to be within the Debye screening length. Thus, the length or size of the nucleotide analog, linker, and label must be sufficient to extend between the active site of the polymerase and the gate (e.g. nanowire or nanotube). In some cases, this can be accomplished by employing a long linker. In some cases this can be accomplished using a relatively large charge label. This conductivity label can be, for example, a protein. In some cases, the protein has a size on the same order of the polymerase enzyme. For example, the protein conductivity label can have a molecular weight from about 1/10 of the weight of the polymerase to about 3 times the molecular weight of the polymerase, or from about 1/5 of the molecular weight of the polymerase to about 2 times the molecular weight of the polymerase. The polymerase can be, for example a phi29 DNA polymerase. An example of a nucleotide analog having a protein conductivity label having a size on the order of the polymerase enzyme is shown in FIG. 18. Polymerase enzyme 1801 is attached to a nanotube 1802 which is the gate of a nanoFET via linker 1803, for example through a covalent bond. The polymerase enzyme 1801 is carrying out template directed nucleic acid synthesis on nucleic acid template 1804. A nucleotide analog 1810 that has the correct (cognate) base for incorporation is held within the active site of the enzyme, and the phosphate portion of the nucleotide analog is extending out of the polymerase. Attached to the phosphate portion of the nucleotide analog through linker 1812 is conductivity label 1811. As can be seen in the figure, the conductivity label 1811 has a size that is on the order of the size of the polymerase enzyme. Because of the selection of size of the charge label, and the lengths of nucleotide analog linker 1812 and polymerase to nanotube linker 1803, the charge label is in the position to product a change in electric signal at the nanotube 1802. It would be understood by those of skill in the art that the sizes and lengths of the components described can be selected in order to control the signal that is detected at the gate. Proteins that can be used as conductivity labels are described, for example in U.S. Patent Application No. 2013/0316912, which is incorporated herein by reference, where such proteins are used as shields in nucleotide analogs. The protein conductivity labels can be mutated by known methods described elsewhere herein for polymerase enzymes to modify the charge and solubility characteristics of the protein conductivity label for control of signal measured at the nanoFET gate.

Figure 19:
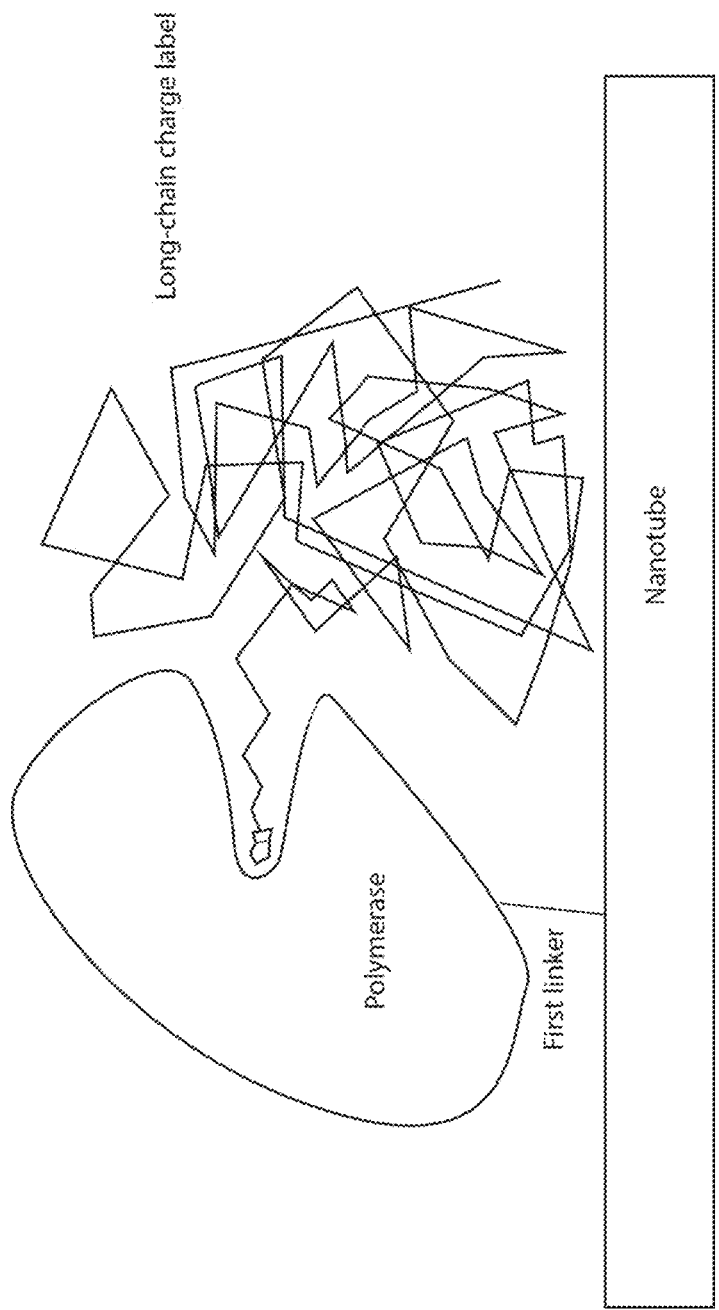
FIG. 19 illustrates how a long chain conductivity label can be used to provide effective signal at the gate of the nanoFET.

FIG. 19 illustrates how a long chain conductivity label can be used to provide effective signal at the gate of the nanoFET. The length of the label can be controlled to obtain the desired level of contact of the conductivity label with the nanotube or nanowire while the labeled nucleotide analog is in the active site of the polymerase. For example, in the embodiment shown in FIG. 19, a long-chain conductivity label is linked to a nucleotide in the active site of a polymerase, where the polymerase is attached to a nanowire or nanotube via a first linker. The label is linked to the terminal phosphate of the nucleotide and has a length sufficient to produce a radius of gyration that will include the surface of the nanowire detector even from the position of the active site of the polymerase. For this purpose, molecules of about 1 nm to about 3 nm are typically used for ensuring the occasional visitation of charged portions of the labeled molecule within range of the nanowire detector, although longer molecules, up to 5, 10, 20, 40, or even 100 nm in length can also be useful. Note that the long chain is described herein as part of the conductivity label. It would be understood that in some cases, some of the length could be in the linker within the nucleotide analog.

In a related embodiment, a terminal phosphate conductivity label contains a block co-polymer or other polymer such that the label includes a hydrophobic or other non-covalent moiety that has affinity for the nanotube. This label can be charged or uncharged. The affinity of the polymer for the nanotube results in the polymer and therefore the label spending more time within the detection region near the nanotube. That is, the polymer will be gyrating over time, and its affinity for the nanotube will allow for it to partition towards the surface (and hence the detection region) of the nanotube. In a preferred embodiment of this strategy, the off rate of the non-covalent binding moiety is greater than 10 times the incorporation rate of the polymerase or more preferably more than 100 times the incorporation rate of the polymerase, or even more preferably more than 500 times the incorporation rate of the polymerase. In some embodiments, the duty cycle of association with the nanowire is 50% higher than without the moiety or 100% higher or 300% higher or 1000% higher that without the moiety or greater.

Distinguishing Labels—Calling Bases

In the sequencing methods of the invention, there are usually two or more different types of labeled nucleotide analogs, and typically there are four different types of nucleotide analog. There are various approaches to distinguish the various types of bases. The discussion will generally involve distinguishing four bases but it is understood that the same approaches can be used to distinguish, two, three, five or more types of nucleotide analogs.

Figure 20:
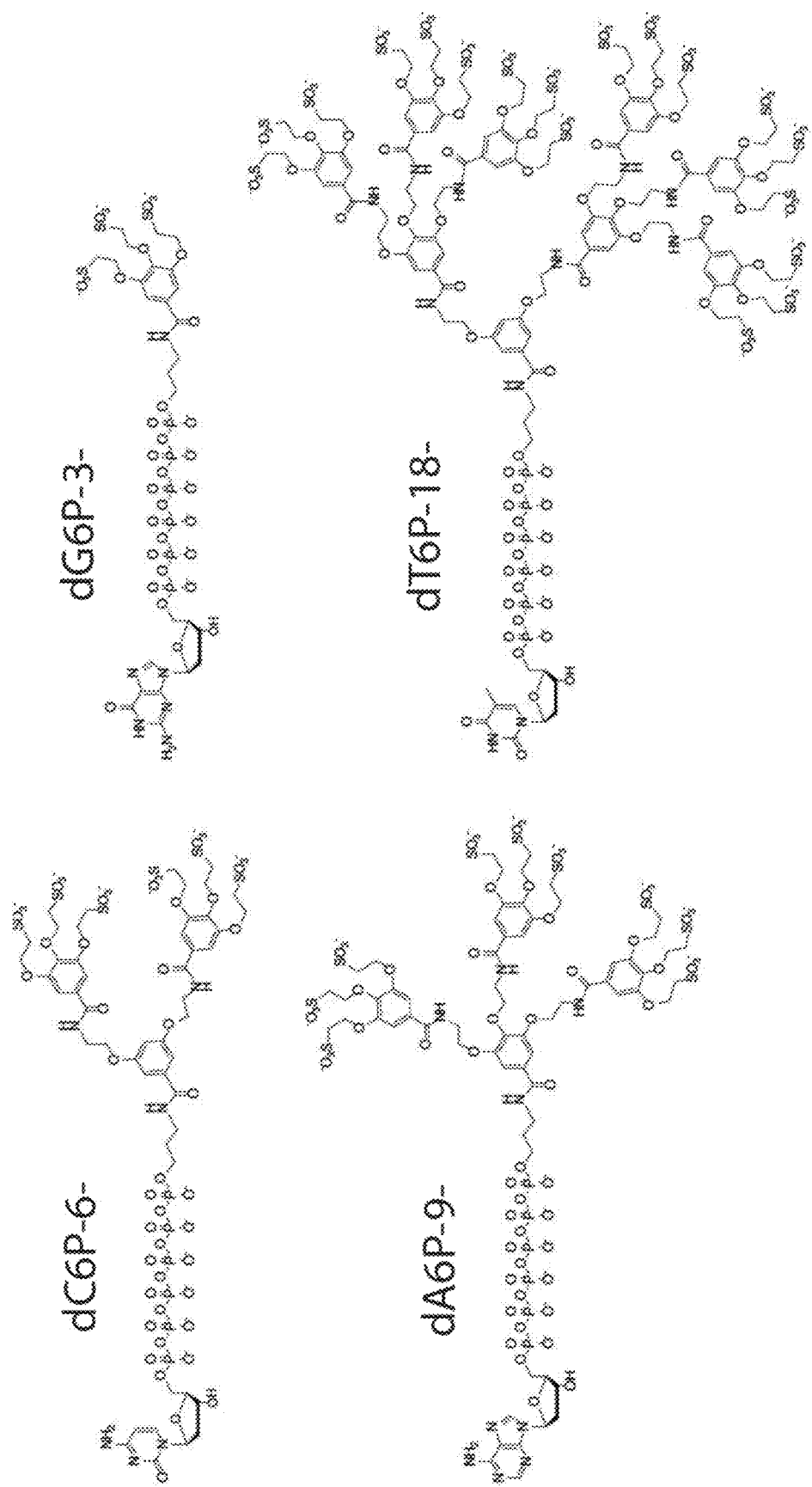
FIG. 20 shows an exemplary set of nucleotide analogs providing four differentiable charged conductivity labels.

One example of such a set of four differently labeled nucleotide analogs is shown in FIG. 20. Each of four different nucleotide types carries a distinguishable charge label, with 3, 6, 9 or 18 negative charges. There are four different nucleotide analogs. The analogs correspond to analogs for DNA synthesis corresponding to the natural bases C, G, A, and T. In each of the analogs, the polyphosphate chain has 6 phosphates. Here the charged conductivity labels are connected through a relatively short linker of a few carbons. One of skill will appreciate that this is an illustrative set of nucleotide analogs, and that changes in the nucleotide portion, the number of phosphates in the polyphosphate change, the length and chemical structure of the linker and the relative number of charges can be changed in order to select the desired level of signal at the nanoFET for the sequencing system of interest.

Figure 21:
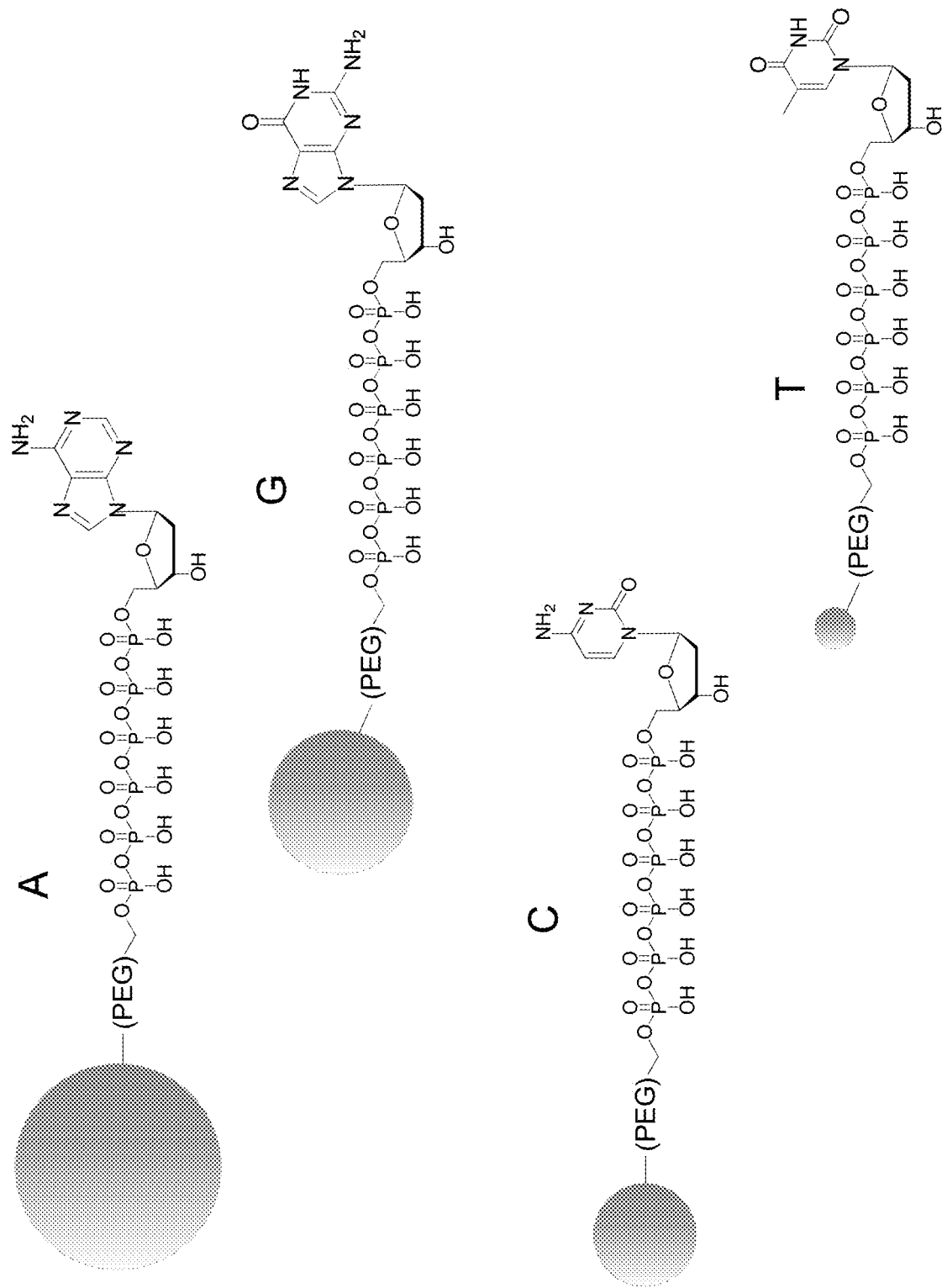
FIG. 21 shows an exemplary set of nucleotide analogs providing four differentiable nanoparticle conductivity labels.

One example of such a set of four differently labeled nucleotide analogs is shown in FIG. 21. Each of the analogs has a nucleotide portion comprising a hexaphosphate, a deoxy ribose, and a nucleobase. Attached to the terminal phosphate of the nucleotide moiety is a polyethylene glycol (PEG) linker. The PEG linker has 77 PEG units and is connected to the conductivity label. Attached to each of the nucleotide analogs is a sphere of a different size. In this example, polystyrene spheres are used. In other examples, for example, titanium dioxide, or gold spheres are used. The nucleotide analog corresponding to G has a polystyrene sphere with diameter of about 15 nm. The nucleotide analog corresponding to A has a polystyrene sphere with diameter of about 25 nm. The nucleotide analog corresponding to T has a polystyrene sphere with diameter of about 5 nm, and the nucleotide analog corresponding to C has a polystyrene sphere with diameter of about 10 nm. This is just one of many sets of four different nucleotide analogs that can be used for sequencing. In some cases, rather than four different sized nanoparticles, the four different nucleotides can each have the same type and size of nanoparticle, but each having a different type of linker.

Distinguishing nucleotide types is done, for example, using the characteristics of magnitude of impedance, impedance versus frequency, and impedance current versus time characteristics (current oscillation color) measured at the gate of the nanoFET. Combinations of the above can also be useful; for example by using two labels and two amplitudes; two types of impedance versus frequency, and two types of current oscillation color, etc. For example, controlling the number, density, and type of charge, and the use of macromolecular charged labels can be useful for either type of electrical detection.

Labels that can provide differences in gate conductivity are known in the art. In some cases, small molecules can be used. In some case a particle, such as a nanoparticle is used as the conductivity label. The characteristics of the nanoparticle can be varied in order to produce different electrical signals at the gate of the nanoFET. The size of the nanoparticle can influence the capacitance of the particle, as well as the chemical structure. Nanoparticles of metals, semiconductors, glasses, oxides, carbon, silicon, protein, polymers, ionic materials, can be used and can be produced to have widely different gate conductivity magnitude and gate conductivity versus frequency characteristics. The size of the particles can be varied over a wide range, for example from about 2 nanometers to about 50 nanometers in diameter. One contributor to the electrical signal change near an electrode is the capacitance characteristics of the nanoFET and associated nanowires. However, it is to be understood that the impedance that is being measured is that of the region around the electrode, and not just that of the label. For example, a nanoparticle label will displace the solution near the electrode, such that the measured electrical signal at the gate will include that change. Thus, a label near the gate of the nanoFET can result in the conductivity either going up or going down as compared to the conductivity when the label is not present.

Differentiating nucleotide analogs based on the magnitude conductivity change can be carried out, for example, by providing a conductivity label having multiple conductive moieties on a nucleotide analog. Nucleotide analog structures including those having multivalent scaffolds and nucleotides having multiple moieties can be prepared as described, for example, in US Patent Application 20120058473 Molecular Adaptors for Dye Conjugates, and US Patent Application 20120077189 Scaffold-Based Polymerase Enzyme Substrates, which are incorporated herein by reference for all purposes. While these references generally describe a fluorescent label, it is to be understood in conjunction with the teachings of this application that a suitable conductivity label connected by a suitable linker as described herein can be substituted for the fluorescent label.

The terms impedance, conductivity, and capacitance are used herein to describe electrical characteristics, for example measured at the gate of a nanoFET. It is to be understood that impedance is a more general term, and that impedance typically has both capacitive and resistive (conductivity) components. For example, for a given system, current flow at low frequencies is dominated by the level of conductivity or resistivity, while the current flow at high frequencies is dominated by the level of capacitance. In some cases frequencies are on the order of tens of kilohertz or greater. At these frequencies, for the geometries and materials described, the impedance is predominated by capacitive rather than resistive components. In some cases, low frequencies including DC can be used in which resistivity (conductivity) is the dominant component. While the impedance in each case may be dominated by one component, either capacitance or resistivity, it is will be understood by those of skill in the art that in some cases a combination of these components is present and those of skill in the art will understand the meanings of the terms by their context herein.

Nucleotide analogs can also be differentiated by their impedance versus frequency characteristics. The measured impedance of a label will also be highly dependent on the frequency. It is well known that the components that contribute to impedance in a given system can vary significantly with frequency, for example ionic motion can predominate at some frequencies and dipolar contributions can predominate at other frequencies. Measurements of this type are sometimes referred to as impedance spectroscopy or dielectric spectroscopy measurements. See e.g. Barsoukov, et al. "Impedance Spectroscopy: Theory, Experiment, and Applications", Wiley, 2005, and Kremer et al. "Broadband dielectric spectroscopy", Springer, 2003, the contents of which are incorporated herein by reference for all purposes. Different labels exhibit different impedance versus frequency characteristics, and these characteristics can be used to provide distinct labels and to increase the confidence in base calling.

The impedance of a label can also vary with the amplitude of the voltage applied to the nanoscale electrode at a given frequency. The voltage applied can be adjusted to obtain the best distinction between the various labels. In some cases, the voltage can be varied instead of or in addition to varying the frequency as described above, allowing labels to be distinguished, at least in part, by their impedance versus electrode voltage characteristics.

The current versus time characteristics can be referred to as current oscillation color. For example, two nucleotide analogs, each having the same conductivity label but having different length linkers can exhibit different electrical signal versus time characteristics. Current oscillation color can be used for nanoFET devices. The nucleotide with the longer linker, may, for example, diffuse differently and thus exhibit a different impedance over time characteristics than the nucleotide analog with the shorter linker. This difference in frequency of current oscillation can be used to determine which of the nucleotide analogs is associated with the enzyme. In addition to linker length, the current oscillation color can be influenced by other characteristics of the linker such as its spring constant. The current oscillation color will depend on the characteristics of the measurement system such as electrode geometry and polymerase complex attachment. These factors can be chosen to control differences in current oscillation color to enhance the determination of which nucleotide is incorporated.

Nucleotides or analogs that can thus be identified by the spectrum of the electrical oscillation they produce. In some cases, oscillations looks like noise, but with reproducible and identifiable characteristics including the frequency and the magnitude of the signal. These different types of oscillations can be used like different colored dyes are used to differentiate between different nucleotide analogs in optical systems, thus, we refer herein to a distinguishable type of current oscillation as a current oscillation color.

One aspect of the invention is the utilization of additional parameters beyond just the impedance change and the impedance spectrum of a label to classify the species associated with the enzyme. Such parameters are measurable over the duration of a pulse. Two general categories of measurement scenarios are: quasi-equilibrium measurement and non-equilibrium measurement.

In quasi-equilibrium measurement, there is some static constraints that remains in place over the duration of the event, and that the removal of that constraint effectively determines the end of the event (except for a negligibly short interval at the end while the detectable object clears the electrode). Though the constraint is fixed, the rest of the components of the system are free to move, and this leads to fluctuations in the signal. For example, diffusion (or equivalently Brownian motion) will cause movement of the label. Under most circumstances, that motion will be correlated with changes in the current across the nanotube, and thus the voltages that might be measured elsewhere in the system. Because of this, aspects of the detectable moiety such as the submolecular diffusion constant (the diffusibility of just that part of the molecule, even when another part of the molecule is constrained) will change the speed of those motions and thus the characteristic frequencies with which the observed voltages or currents will change. For example, a fast diffuser will generally have a whiter noise spectrum, while a slower diffuser will tend to produce a pinker current oscillation spectrum.

The current oscillation color can be used as the basis for a discriminator, for example, by 1) taking the current oscillation signature over a region of interest (e.g. over the duration of the event), 2) performing a Fourier transform analysis or an autocorrelation analysis, and examine the spectrum of the current oscillation over the range of frequencies available (e.g. from $f=1/T$ where T is the duration of the pulse, up to the cutoff frequency of the amplifier system, or somewhat beyond the cutoff). This process will result in a digitally sampled current oscillation amplitude as a function of frequency. This could be represented by as few as two samples (a low frequency region and a high frequency region), 3, 4, 5, 6, 7, 8, 9, 10, 11, 12, 16, 32, 64, 128, 256, 512, 1024 or more bins. The values in these bins could be discrete samples of a function or they represent integrals over a region of interest of the idealized continuous function. This set of discrete values can be represented as a vector that can be classified by one of many machine learning systems such as k-means clustering, SVM, CART or boosted CART, PCA and many others. Thus, as described herein, current oscillation color can be used to discriminate detectable moieties. Detection systems that are based on current oscillation color can be referred to as "current oscillation color identification systems", and when moieties engineered for producing different current oscillation color are used, they are referred to as "current oscillation color tags". In a sequencing system, when nucleotide base sequence is identified on this basis it can be referred to as a current oscillation color sequencing system (whether the current oscillation color is intrinsic to the bases or the result of current oscillation color tags).

Other aspects besides the diffusion constant can affect the current oscillation color of the signal. For example, in the embodiments that use linkers with different elastic constants, this will affect the magnitude of these diffusive fluctuations, which will then affect the current oscillation signal (not to be confused with the amplitude of the DC current during the event—this is referring to the RMS noise of the signal over the duration of the event.). In analogy with color systems that have RGB, or HSV, color can be generalized to include the "brightness" of the color. In the above-mentioned spectrum analysis model, this would result in the values in the vector being larger for moieties capable of larger excursions, and lower values for moieties that are more constrained in position. Some or all of these signals can be exploited in the machine learning paradigm indicated above. There are many aspects that can affect the size of the excursions.

The nanoscale electrodes used to connect the nanoFETs or that are part of the nanoFET, e.g. the source and the drain are typically prepared such that the electrodes have low capacitance in order to allow for rapidly changing the voltage on the electrodes to carry out the sequencing methods described herein. The resistance and capacitance are kept low by the selection of materials and by the geometry of the electrodes and the spacing of the electrodes. One of the considerations is keeping the RC time constant of each capacitive device low enough to allow for changing the voltage on the electrodes to carry out the methods described herein. In some cases, the RC time constant for the electrode is less than 100 microseconds, less than 10 microseconds, less than 1 microsecond, less than 0.1 microseconds, or less than 0.01 microseconds. In some cases, the RC time constant is between 0.01 microseconds and 100 microseconds. In order to keep the RC time constant low, the electrodes and the interconnects that carry current to and from the electrodes are formed from a material having an electrical conductivity of greater than 106 S/m. Suitable materials include copper, silver, gold, platinum, and aluminum. In order to keep the capacitance low, the dimensions of the electrodes are also generally small—on the nanometer scale. In addition, where there are two electrodes near each other as in the two electrode configuration, while the electrode portions exposed to the surface are close together, the electrodes are configured not to have large portions where the two electrodes are within a few nanometers. It is also an aspect of the invention to minimize the area of electrodes that is in contact with conductive liquid so as to control the capacitance of the system. Similarly it is an aspect of the invention to use insulating layers to increase the distance to ground planes, other electrodes, or any other conductor which could produce stray capacitance.

The ability to electrically address the small devices of the instant invention quickly due to the low RC time constant of the structures is useful for carrying out the invention as it allows for sampling multiple frequency regimes to identify the identity of the different components that are present.

The methods described herein provide for identifying the nucleotide analogs that are incorporated in to a growing nucleic acid strand as they are incorporated in the bound polymerase-template complex. The presence and identity of the bases is measured by measuring electrical signals in the nanoFET proximate to the bound polymerase-template complex. As described above, the presence of a conductivity label corresponding to a particular base proximate to a nanoFET for a period of time corresponding to the time for base incorporation indicates that that base has been incorporated. The incorporation of that base into the growing strand indicates the presence of the complementary base in the template strand, providing sequence information about the template. The calling of bases is done using software that takes the current versus time information, and in some cases other information in order to call the base that has been incorporated.

An exemplary process for pulse recognition is as follows. Once the current traces have been generated for a given nanoFET device for a certain time period, the current traces are subjected to a pulse recognition process. In the initial step, a baseline is established for the trace. Typically, the baseline may comprise signal contributions from a number of background sources (depending on the details of the spectral and trace extraction steps). For example, such noise can include, e.g., global background (e.g. large scale spatial cross-talk) and diffusion background. These backgrounds are generally stable on the timescales of pulses, but still may vary slowly over longer timescales. Baseline removal comprises any number of techniques, ranging from, e.g.: a median of the trace, running lowest-percentile with bias correction, polynomial and/or exponential fits, or low-pass filtering with an FFT. Generally these methods will attempt to be robust to the presence of pulses in the trace and may actually be derived at through iterative methods that make multiple passes at identifying pulses and removing them from consideration of baseline estimation. In certain preferred embodiments, a baseline or background model is computed for each trace channel, e.g., to set the scale for threshold-based event detection.

Other baselining functions include correction for drift or decay of overall signal levels. For example, global background decay is sometimes observed. This global background decay is present on portions of the substrate at which there is no enzyme bound proximate to nanoFETs, thus allowing the traces derived from these locations to be used in combination with the two dimensional global background image to estimate the contribution of this signal to every trace/channel across the chip. This component of variability can then be subtracted from each trace and is usually very effective at removing this decay. Typically, this is carried out prior to the baselining processes.

Following establishment of the baseline the traces are subjected to noise suppression filtering to maximize pulse detection. In particularly preferred aspects, the noise filter is a 'matched filter' that has the width and shape of the pulse of interest. While current pulse timescales (and thus, pulse widths) are expected to vary among different capacitive labeled nucleotides, the preferred filters will typically look for pulses that have a characteristic shape with varying overall duration. For example, a boxcar filter that looks for a current pulse of prolonged duration, e.g., from about 10 ms to 100 or more ms, provides a suitable filter. This filtering is generally performed in the time-domain through convolution or low-pass frequency domain filtering. Other filtering techniques include: median filtering (which has the additional effect of removing short timescale pulses completely from the trace depending on the timescale used), and Savitsky-Golay filtering which tends to preserve the shape of the pulse—again depending on the parameters used in the filter).

Although described in terms of a generic filtering process across the various traces, it will be appreciated that different pulses may have different characteristics, and thus may be subjected to trace specific filtering protocols. For example, in some cases, a given labeled analog (e.g., A) may have a different pulse duration for an incorporation event than another different labeled analog (e.g., T). As such, the filtering process for the spectral trace corresponding to the A analog will have different filtering metrics on the longer duration pulses, than for the trace corresponding to the T analog incorporation. In general, such filters (e.g., multiscale filters) enhance the signal-to-noise ratio for enhanced detection sensitivity. Even within the same channel there may be a range of pulse widths. Therefore typically a bank of these filters is used in order to maximize sensitivity to pulses at a range of timescales within the same channel.

In identifying pulses on a filtered trace, a number of different criteria can be used. For example, one can use absolute current amplitude, either with or without normalization. Alternatively, one can identify pulses from the pulse to diffusion background ratio as a metric for identifying the pulse. In still other methods, one may use statistical significance tests to identify likely pulses over the background noise levels that exist in a given analysis. The latter method is particularly preferred as it allows for variation in potential pulse intensities, and reduces the level of false positives called from noise in the baseline.

As noted previously, a number of signal parameters including amplitude of capacitance change, impedance versus frequency, residence time, and current oscillation color may be and generally are used in pulse identification (as well as in pulse classification). For purposes of illustration, the discussion below primarily on the use of two pulse metrics, namely pulse intensity and pulse width. As will be appreciated, the process may generally include any one or more of the various pulse metric comparisons set forth elsewhere herein.

As such, following filtering, standard deviation of the baselines (noise and current pulses) and determination of pulse detection thresholds are carried out. Preferred methods for determining the standard deviation of a trace include robust standard deviation determinations including, e.g., being based upon the median absolute difference about the baseline, a Gaussian or Poisson fit to the histogram of baselined intensities, or an iterative sigma-clip estimate in which extreme outliers are excluded. Once determined for each trace, a pulse is identified if it exceeds some preset number of standard deviations from the baseline. The number of standard deviations that constitute a significant pulse can vary depending upon a number of factors, including, for example, the desired degree of confidence in identification or classification of significant pulses, the signal to noise ratio for the system, the amount of other noise contributions to the system, and the like. In a preferred aspect, the up-threshold for an incorporation event, e.g., at the initiation of a pulse in the trace, is set at about 5 standard deviations or greater, while the down-threshold (the point at which the pulse is determined to have ended) is set at 1.25 standard deviations. Up thresholds can be used as low as 3.75 standard deviations and as high as the signal-to-noise ratio will allow—up to 7, 10, 20 or 50 standard deviations. The down threshold can be set anywhere from minus 1 standard deviation up to the up threshold. Alternatively, the down threshold can be computed from the mean and standard deviation of the up signal, in which case it could be set between minus 3 standard deviations to minus 6 standard deviations. If the signal-to-noise ratio is sufficiently high it could be set to minus 7, 10, 20 or 50 standard deviations. The pulse width is then determined from the time between the triggering of the up and down thresholds. Once significant pulses are initially identified, they are subjected to further processing to determine whether the pulse can be called as a particular base incorporation. Alternatively the signals can be filtered ahead of time to eliminate frequency components that correspond to timescales not likely to correspond to true incorporation events, in which case the further processing steps are optional.

In some cases, multiple passes are made through traces examining pulses at different timescales, from which a list of non-redundant pulses detected at such different time thresholds may be created. This typically includes analysis of unfiltered traces in order to minimize potential pulse overlap in time, thereby maximizing sensitivity to pulses with width at or near the highest frame rate of the camera. This allows the application of current oscillation color or other metrics to current pulses that inherently operate on different timescale. In particular, an analysis at longer timescales may establish trends not identifiable at shorter timescales, for example, identifying multiple short timescale pulses actually correspond to a single longer, discrete pulse.

In addition, some pulses may be removed from consideration/evaluation, where they may have been identified as the result of systematic errors, such as through spatial cross-talk of adjacent devices, or cross-talk between detection channels (to the extent such issues have not been resolved in a calibration processes). Typically, the calibration process will identify cross-talk coefficients for each device, and thus allow such components to be corrected.

In certain embodiments, a trace-file comprises L-weighted-sum (LWS) traces, where trace is optimized to have maximum pulse detection sensitivity to an individual label in the reaction mixture. This is not a deconvolved or multicomponent trace representation, and suffers from spectral cross-talk.

Classification of an extracted pulse into one of the 4(or N) labels is then carried out by comparing the extracted spectrum to the spectra of the labels sets established in a calibration process. A number of comparative methods may be used to generate a comparative metric for this process. For example, in some aspects, a $\chi 2$ test is used to establish the goodness of fit of the comparison. A suitable $\chi 2$ test is described, for example, in U.S. Patent Application 20120015825, incorporated herein by reference for all purposes.

Once the pulse spectrum is classified as corresponding to a particular label spectrum, that correlation is then used to assign a base classification to the pulse. As noted above, the base classification or "calling" may be configured to identify directly the labeled base added to the extended primer sequence in the reaction, or it may be set to call the complementary base to that added (and for which the pulse spectrum best matches the label spectrum). In either case, the output will be the assignment of a base classification to each recognized and classified pulse. For example, a base classification may be assignment of a particular base to the pulse, or identification of the pulse as an insertion or deletion event.

In an ideal situation, once a pulse is identified as significant and its spectrum is definitively identified, a base is simply called on the basis of that information. However, as noted above, in typical sequencing runs, signal traces can include signal noise, such as missing pulses (e.g., points at which no pulse was found to be significant, but that correspond to an incorporation event) false positive pulses, e.g., resulting from nonspecifically adsorbed analogs or labels, or the like. Accordingly, pulse classification (also termed base classification) can in many cases involve a more complex analysis. As with pulse identification, above, base classification typically relies upon a plurality of different signal characteristics in assigning a base to a particular identified significant pulse. In many cases, two, three, five, ten or more different signal characteristics may be compared in order to call a base from a given significant pulse. Such characteristics include those used in identifying significant pulses as described above, such as pulse width or derivative thereof (e.g., smooth pulse width estimate, cognate residence time, or non-cognate residence time), pulse intensity, pulse channel, estimated average current amplitude of pulse, median current amplitude of all pulses in the trace corresponding to the same channel, background and/or baseline level of channel matching pulse identity, signal to noise ratio (e.g., signal to noise ratio of pulses in matching channel, and/or signal to noise ratio of each different channel), power to noise ratio, integrated counts in pulse peak, maximum signal value across pulse, pulse density over time (e.g., over at least about 1, 2, 5, 10, 15, 20, or 30 second window), shape of and distance/time to neighboring pulses (e.g., interpulse distance), channel of neighboring pulses (e.g., channel of previous 1, 2, 3, or 4 pulses and/or channel of following 1, 2, 3, or 4 pulses), similarity of pulse channel to the channel of one or more neighboring pulses, signal to noise ratio for neighboring pulses; spectral signature of the pulse, pulse centroid location, and the like, and combinations thereof. Typically, such comparison will be based upon standard pattern recognition of the metrics used as compared to patterns of known base classifications, yielding base calls for the closest pattern fit between the significant pulse and the pattern of the standard base profile.

Comparison of pulse metrics against representative metrics from pulses associated with a known base identity will typically employ predictive or machine learning processes. In particular, a "training" database of "N previously solved cases" is created that includes the various metrics set forth above. For example, a vector of features is analyzed for each pulse, and values for those features are measured and used to determine the classification for the pulse, e.g., an event corresponding to the pulse, e.g., an incorporation, deletion, or insertion event. As used herein, an incorporation event refers to an incorporation of a nucleotide complementary to a template strand, a deletion event corresponds to a missing pulse resulting in a one position gap in the observed sequence read, and an insertion event corresponds to an extra pulse resulting in detection of a base in the absence of incorporation. For example, an extra pulse can be detected when a polymerase binds a cognate or noncognate nucleotide but the nucleotide is released without incorporation into a growing polynucleotide strand. From that database, a learning procedure is applied to the data in order to extract a predicting function from the data. A wide variety of learning procedures are known in the art and are readily applicable to the database of pulse metrics. These include, for example, linear/logistic regression algorithms, neural networks, kernel methods, decision trees, multivariate splines (MARS), multiple additive regression trees (MART™), support vector machines.

In addition to calling bases at pulses identified as significant, the present methods also allow for modeling missing pulses. For example, conditional random fields (CRF) are probabilistic models that can be used to in pulse classification (see, e.g., Lafferty, et al. (2001) Proc.Intl. Conf. on Machine Learning 01, pgs 282-289, incorporated herein by reference in its entirety for all purposes). A CRF can also be conceptualized as a generalized Hidden Markov Model (HMM), some examples of which are described elsewhere herein and are well known in the art. The present invention includes the use of CRFs to model missing bases in an observed pulse trace. In addition to base calling, algorithms for consensus generation and sequence alignment can be used to obtain further information from the sequencing methods described herein.

Methods for calling bases, consensus generation, and sequence alignment are described, for example, in the following patents and applications, which are incorporated herein for all purposes: U.S. Pat. No. 7,995,202 "Methods and Systems for Simultaneous real-time monitoring of optical signals from multiple sources"; U.S. Pat. No. 7,626,704 "Methods and systems for simultaneous real-time monitoring of optical signals from multiple sources"; U.S. Pat. No. 8,182,993 "Methods and Processes for Calling Bases in Sequence by Incorporation Methods"; U.S. Ser. No. 13/468347 filed May 10, 2012, "Algorithms for Sequence Determination"; US 20120015825 "Analytical Systems and Methods with Software Mask"; US 20110257889 "Sequence Assembly and Consensus Sequence Determination"; US 20120052490 "Methods and Systems for Monitoring Reactions"; US 20100169026 "Algorithms for Sequence Determination Processing". While the base identification and base calling algorithms in the above documents are typically described referring to optical systems, in light of the current specification, one of ordinary skill in the art would understand how to bring such methods to bear in the nanoFET sequencing systems and methods of the present invention.

Polymerase-Nucleic Acid Complex

The polymerase-enzyme complex of the invention comprises a nucleic acid polymerase enzyme associated with a template molecule. The template also typically has a primer hybridized to it, while some polymerase enzymes can initiate nucleic acid synthesis without the addition of an external primer. While many enzyme-substrate interactions are transient, some polymerase enzymes can form relatively stable complexes with nucleic acids that can be manipulated, purified, and then subsequently used to carry out nucleic acid synthesis. For example, DNA polymerases having relatively high processivity can have strong associations with template nucleic acid molecules. An exemplary DNA Polymerase is phi-29 DNA polymerase. Methods for forming and manipulating polymerase-nucleic acid complexes are described, for example in copending U.S. Patent Application entitled Purified Extended Polymerase/Template Complex for Sequencing" 61/385376, filed Sep. 22, 2010 and U.S. patent application Ser. No. 13/427,725 filed Mar. 22, 2012 entitled "Isolation of Polymerase-Nucleic Acid Complexes" which is incorporated by reference herein in its entirety for all purposes.

The polymerase-nucleic acid complex will typically comprise a polymerase and a nucleic acid having a double stranded region. The polymerase-nucleic acid complex will generally have a primer from which a nascent nucleic acid strand will be produced complementary to a template strand of the nucleic acid. The primer is usually a short oligonucleotide that is complementary to a portion of the template nucleic acid. The primers of the invention can comprise naturally occurring RNA or DNA oligonucleotides. The primers of the invention may also be synthetic analogs. The primers may have alternative backbones as described above for the nucleic acids of the invention. The primer may also have other modifications, such as the inclusion of heteroatoms, the attachment of labels, or substitution with functional groups which will still allow for base pairing and for recognition by the enzyme. Primers can select tighter binding primer sequences, e.g., GC-rich sequences, as well as employ primers that include within their structure non-natural nucleotides or nucleotide analogs, e.g., peptide nucleic acids (PNAs) or locked nucleic acids (LNAs), that can demonstrate higher affinity pairing with the template. In some cases, the primer is added as a separate component to form the complex; in other cases, the primer can be part of the nucleic acid that used. For example, in some cases priming can begin at a nick or a gap in one strand of a double-stranded nucleic acid.

The template nucleic acid can be derived from any suitable natural or synthetic source. In preferred embodiments, the template comprises double stranded DNA, but in some circumstances double-stranded RNA or RNA-DNA heteroduplexes can be used. The template nucleic acid can be genomic DNA from eukaryotes, bacteria, or archaea. The template nucleic acid can be cDNA derived from any suitable source including messenger RNA. The template nucleic acid can comprise a library of double stranded segments of DNA. The template nucleic acid can be linear or circular. For example, the nucleic acid can be topologically circular and have a linear double stranded region. A circular nucleic acid can be, for example, a gapped plasmid. In some embodiments the nucleic acid is a double stranded linear DNA having a gap in one of the strands. The gap provides a site for attachment of the polymerase enzyme for nucleic acid synthesis. The linear double stranded DNA having a double-stranded DNA adaptor can be made by ligation of DNA fragment to an adaptor through blunt end-ligation or sticky end ligation. The ligation produces a linear DNA having a gap close to the 5' end of one or both of the strands. The gap can be any suitable width. For example, the gap can be from 1 to 50 bases, from 2 to 30 bases, or from 3 to 12 bases.

The terms "nucleic acid" or "oligonucleotide" or grammatical equivalents herein mean at least two nucleotides covalently linked together. A nucleic acid of the present invention will generally contain phosphodiester bonds, although in some cases, nucleotide analogs are included that may have alternate backbones, comprising, for example, phosphoramide, phosphorothioate, phosphorodithioate, and peptide nucleic acid backbones and linkages. Other analog nucleic acids include those with positive backbones, non-ionic backbones, and non-ribose backbones, including those described in U.S. Pat. Nos. 5,235,033 and 5,034,506. The template nucleic acid may also have other modifications, such as the inclusion of heteroatoms, the attachment of labels, or substitution with functional groups which will still allow for base pairing and for recognition by the enzyme.

The template sequence may be provided in any of a number of different format types depending upon the desired application. The template may be provided as a circular or functionally circular construct that allows redundant processing of the same nucleic acid sequence by the synthesis complex. Use of such circular constructs has been described in, e.g., U.S. Pat. No. 7,315,019 and U.S. patent application Ser. No. 12/220674, filed Jul. 25th, 2008. Alternate functional circular constructs are also described in U.S. patent application Ser. No. 12/383855, filed Mar. 27, 2009, and U.S. Pat. No. 8,153,375 Compositions and Methods for Nucleic Acid Sequencing; U.S. Pat. No. 8,003,330 Error-Free Amplification of DNA for Clonal Sequencing; and Ser. No. 13/363,066 filed Jan. 31, 2012 Methods and Compositions for Nucleic Acid Sample Preparation, the full disclosures of each of which are incorporated herein by reference in their entirety for all purposes.

Briefly, such alternate constructs include template sequences that possess a central double stranded portion that is linked at each end by an appropriate linking oligonucleotide, such as a hairpin loop segment. Such structures not only provide the ability to repeatedly replicate a single molecule (and thus sequence that molecule), but also provide for additional redundancy by replicating both the sense and antisense portions of the double stranded portion. In the context of sequencing applications, such redundant sequencing provides great advantages in terms of sequence accuracy.

The nucleic acids can comprise a population of nucleic acids having universal sequence regions that are common to all of the nucleic acids in the population and also have specific regions that are different in the different members of the population. The current invention allows for capturing and isolating polymerase-nucleic acid complexes using either the universal or the specific regions.

While in many cases nucleic acid synthesis is describe herein as extending from a primer, it is to be understood that some polymerases do not require an added external primer, and can be initiated using terminal protein. Polymerases that can be initiated using terminal protein include phi-29 polymerase.

Polymerase Enzymes

Polymerase enzymes useful in this invention can include any suitable nucleic acid polymerase. Types of polymerases that can be used are described in more detail herein.

DNA Polymerases

DNA polymerases are sometimes classified into six main groups based upon various phylogenetic relationships, e.g., with E. coli Pol I (class A), E. coli Pol II (class B), E. coli Pol III (class C), Euryarchaeotic Pol II (class D), human Pol beta (class X), and E. coli UmuC/DinB and eukaryotic RAD30/xeroderma pigmentosum variant (class Y) which are incorporated by reference herein for all purposes. For a review of recent nomenclature, see, e.g., Burgers et al. (2001) "Eukaryotic DNA polymerases: proposal for a revised nomenclature" J Biol Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398, which are incorporated by reference herein for all purposes. The basic mechanisms of action for many polymerases have been determined. The sequences of literally hundreds of polymerases are publicly available, and the crystal structures for many of these have been determined, or can be inferred based upon similarity to solved crystal structures of homologous polymerases. For example, the crystal structure of Φ29, a preferred type of parental enzyme to be modified according to the invention, is available.

In addition to wild-type polymerases, chimeric polymerases made from a mosaic of different sources can be used. For example, Φ29 polymerases made by taking sequences from more than one parental polymerase into account can be used as a starting point for mutation to produce the polymerases of the invention. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296) which are incorporated by reference herein for all purposes. In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, an M2 polymerase, a B103 polymerase, and a GA-1 polymerase, can be generated. Appropriate mutations to enhance performance with nucleotide analogs, increase readlength, improve thermostability, alter reaction rate constants, and/or alter another desirable property as described herein can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al.), to alter branching fraction and translocation (e.g., US patent application publication 2010-0075332 by Pranav Patel et al. entitled "ENGINEERING POLYMERASES AND REACTION CONDITIONS FOR MODIFIED INCORPORATION PROPERTIES"), to increase photostability (e.g., US patent application publication 2010-0093555 by Keith Bjornson et al. entitled "Enzymes Resistant to Photodamage" and US patent application publication 2013-0217007 by Satwik Kamtekar et al. entitled "Recombinant Polymerases with Increased Phototolerance"), to slow one or more catalytic steps during the polymerase kinetic cycle, increase closed complex stability, decrease branching fraction, alter cofactor selectivity, and increase yield, thermostability, accuracy, speed, and readlength (e.g., US patent application publication 2010-0112645 "Generation of Modified Polymerases for Improved Accuracy in Single Molecule Sequencing" by Sonya Clark et al., US patent application publication 2011-0189659 "Generation of Modified Polymerases for Improved Accuracy in Single Molecule Sequencing" by Sonya Clark et al., and US patent application publication 2012-0034602 "Recombinant Polymerases For Improved Single Molecule Sequencing" by Robin Emig et al.), and to improve surface-immobilized enzyme activities (e.g., WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al.), which are incorporated by reference herein for all purposes. Any of these available polymerases can be modified in accordance with the invention.

Many such polymerases that are suitable for modification are available, e.g., for use in sequencing, labeling and amplification technologies. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to enhance performance with nucleotide analogs, increase readlength, improve thermostability, improve detection of base modifications, increase phototolerance, alter reaction rates, reduce or eliminate exonuclease activity, alter metal cofactor selectivity, and/or alter one or more other property described herein include Taq polymerases, exonuclease deficient Taq polymerases, E. coli DNA Polymerase 1, Klenow fragment, reverse transcriptases, Φ29-related polymerases including wild type Φ29 polymerase and derivatives of such polymerases such as exonuclease deficient forms, T7 DNA polymerase, T5 DNA polymerase, an RB69 polymerase, etc.

In one aspect, the polymerase that is modified is a Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or 5,576,204 which are incorporated by reference herein for all purposes. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SF5, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287. Polymerase enzymes useful in the invention include polymerases mutated to have desirable properties for sequencing. Suitable polymerases are described, for example, in US patent application publications 2007-0196846, 2008-0108082, 2010-0075332, 2010-0093555, 2010-0112645, 2011-0059505, 2011-0189659, 2012-0034602, 2013-0217007, 2014-0094374, and 2014-0094375, all of which are incorporated by reference herein for all purposes. Similarly, the modified polymerases described herein can be employed in combination with other strategies to improve polymerase performance, for example, reaction conditions for controlling polymerase rate constants such as taught in US patent application publication 2009-0286245 entitled "Two slow-step polymerase enzyme systems and methods," incorporated herein by reference in its entirety for all purposes.

The polymerase enzymes used in the invention will generally have strand-displacement activity. In some cases, strand displacement is part of the polymerase enzyme itself. In other cases, other cofactors or co-enzymes can be added to provide the strand displacement capability.

RNA Dependent RNA Polymerases

In some embodiments, the polymerase enzyme that is used for sequencing is an RNA polymerase. Any suitable RNA polymerase (RNAP) can be used including RNA polymerases from bacteria, eukaryotes, viruses, or archea. Suitable RNA polymerases include RNA Pol I, RNA Pol II, RNA Pol III, RNA Pol IV, RNA Pol V, T7 RNA polymerase, T3 RNA polymerase or SP6 RNA polymerase. The use of RNA polymerases allows for the direct sequencing of messenger RNA, transfer RNA, non-coding RNA, ribosomal RNA, micro RNA or catalytic RNA. Where RNA polymerases are used, the polymerizing reagents will generally include NTPs or their analogs rather than the dNTPs used for DNA synthesis. In addition, RNA polymerases can be used with specific cofactors. There are many proteins that can bind to RNAP and modify its behavior. For instance, GreA and GreB from E. coli and in most other prokaryotes can enhance the ability of RNAP to cleave the RNA template near the growing end of the chain. This cleavage can rescue a stalled polymerase molecule, and is likely involved in proofreading the occasional mistakes made by RNAP. A separate cofactor, Mfd, is involved in transcription-coupled repair, the process in which RNAP recognizes damaged bases in the DNA template and recruits enzymes to restore the DNA. Other cofactors are known to play regulatory roles; i.e., they help RNAP choose whether or not to express certain genes. RNA dependent RNA polymerases (RNA replicases) may also be used including viral RNA polymerases: e.g. polioviral 3Dpol, vesicular stomatitis virus L, and hepatitis C virus NS5b protein; and eukaryotic RNA replicases which are known to amplify microRNAs and small temporal RNAs and produce double-stranded RNA using small interfering RNAs as primers.

Reverse Transcriptases

The polymerase enzyme used in the methods or compositions of the invention includes RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal RNA, micro RNA or catalytic RNA.

Thus, any suitable polymerase enzyme can be used in the systems and methods of the invention. Suitable polymerases include DNA dependent DNA polymerases, DNA dependent RNA polymerases, RNA dependent DNA polymerases (reverse transcriptases), and RNA dependent RNA polymerases.

Immobilization of the Polymerase-Template Complex

The polymerase-template complex can be attached to a surface such as to the gate of the nanoFET or to a region of the substrate proximate to the nanoFET. Such attachment is typically by binding the polymerase itself, but in some cases can be accomplished by binding the template nucleic acid, or a primer. The binding can be either covalent or non-covalent. In some cases, covalent attachment, for example, covalent attachment to a carbon nanotube is preferred. It is known that in some cases such covalent attachment can result to a single-walled carbon nanotube can result in an enhanced ability to detect molecular changes near the point of covalent attachment. See for example US20130285680, which is incorporated herein by reference. In some cases, an $SiO_2$ region of the surface can be selectively functionalized to bind the polymerase complex. The selective functionalization of $SiO_2$ can be carried out, for example, using silane chemistry. For example, the $SiO_2$ portion of the surface can be selectively treated with a biotin functionalized silane, and the surface can be treated with an enzyme complex attached to streptavidin. The streptavidin-polymerase-template complex will bind specifically to the biotin on the $SiO_2$ portions of the surface providing selective binding. See e.g. U.S. Pat. No. 8,193,123 which is incorporated herein by reference for all purposes. In some cases, small regions, e.g. balls, islands, or pits can be made on the surface that allow only a small number, and in some cases allow only a single polymerase enzyme to bind. The creation of regions to bind a single polymerase enzyme complex are described, for example in U.S. Patent Application 20100009872 Single Molecule Loading Methods and Compositions; and U.S. Patent Application 20110257040 Nanoscale Apertures Having Islands of Functionality which are incorporated herein by reference for all purposes. DNA molecules typically possess a strong negative charge and can thus be directed using electric fields in aqueous solution. Because the devices of the instant invention contemplate arrays of electrodes with means of applying electric potentials and simultaneously measuring currents from proximate labels, the capability exists to use the potential-setting capacity to attract polymerases bound to DNA molecules to the electrode region and then either simultaneously or in alternating periods check to see if a polymerase has bound the system. In this way each active device can be loaded with a single polymerase by ceasing the attractive potential when the binding of a DNA-Polymerase complex is detected.

The immobilization of a component of an analytical reaction can be engineered in various ways. For example, an enzyme (e.g., polymerase, reverse transcriptase, kinase, etc.) may be attached to the substrate at a reaction site, e.g., proximate to a nanoscale electrode. In other embodiments, a substrate in an analytical reaction (for example, a nucleic acid template, e.g., DNA, RNA, or hybrids, analogs, and mimetics thereof, or a target molecule for a kinase) may be attached to the substrate at a reaction site. Certain embodiments of template immobilization are provided, e.g., in U.S. patent application Ser. No. 12/562,690, filed Sep. 18, 2009 and incorporated herein by reference in its entirety for all purposes. One skilled in the art will appreciate that there are many ways of immobilizing nucleic acids and proteins, whether covalently or non-covalently, via a linker moiety, or tethering them to an immobilized moiety. These methods are well known in the field of solid phase synthesis and microarrays (Beier et al., Nucleic Acids Res. 27:1970-1-977 (1999)). Non-limiting exemplary binding moieties for attaching either nucleic acids or polymerases to a solid support include streptavidin or avidin/biotin linkages, carbamate linkages, ester linkages, amide, thiolester, (N)-functionalized thiourea, functionalized maleimide, amino, disulfide, amide, hydrazone linkages, among others. Antibodies that specifically bind to one or more reaction components can also be employed as the binding moieties. In addition, a silyl moiety can be attached to a nucleic acid directly to a substrate such as glass using methods known in the art.

In some embodiments, a nucleic acid template is immobilized onto a reaction site (e.g., proximate to a nanoFET) by attaching a primer comprising a complementary region at the reaction site that is capable of hybridizing with the template, thereby immobilizing it in a position suitable for monitoring. In certain embodiments, an enzyme complex is assembled, e.g., by first immobilizing an enzyme component. In other embodiments, an enzyme complex is assembled in solution prior to immobilization. Where desired, an enzyme or other protein reaction component to be immobilized may be modified to contain one or more epitopes for which specific antibodies are commercially available. In addition, proteins can be modified to contain heterologous domains such as glutathione S-transferase (GST), maltose-binding protein (MBP), specific binding peptide regions (see e.g., U.S. Pat. Nos. 5,723,584, 5,874, 239 and 5,932,433), or the Fc portion of an immunoglobulin. The respective binding agents for these domains, namely glutathione, maltose, and antibodies directed to the Fc portion of an immunoglobulin, are available and can be used to coat the surface of a device of the present invention. The binding moieties or agents of the reaction components they immobilize can be applied to a support by conventional chemical techniques which are well known in the art. In general, these procedures can involve standard chemical surface modifications of a support, incubation of the support at different temperature levels in different media comprising the binding moieties or agents, and possible subsequent steps of washing and cleaning.

The various components of the surface of the devices can be selectively treated in order to bind the polymerase-template complex to a specific portion of the substrate. Selective treatment and immobilization is described, for example, in U.S. Pat. Nos. 5,624,711; 5,919,523; Hong et al., (2003) Langmuir 2357-2365; U.S. Pat. Nos. 5,143,854; 5,424,186; 8,137,942; 7,993,891 Reactive surfaces, substrates and methods of producing and using same; U.S. Pat. Nos. 7,935,310; 7,932,035 7,931,867 Uniform surfaces for hybrid material substrates and methods of making and using same; and U.S. Pat. No. 8,193,123 Articles having localized molecules disposed thereon and methods of producing same, all of which are incorporated herein by reference for all purposes.

The polymerase complex is typically attached directly to the gate of the nanoFET (e.g. the nanowire or carbon nanotube), but in some cases the polymerase complex is attached proximate to the gate. Such an attachment is made close enough to the nanoFET that the conductive label on a nucleotide analog held in the active site of the enzyme can extend close enough to the electrode to allow for detection. The polymerase complex can be attached for example from about 1 nm to about 100 nm from the gate of a nanoFET, from about 2 nm to about 50 nm from the gate of a nanoFET, or from about 4 nm to about 20 nm from the gate of a nanoFET.

Conditions for Nucleic Acid Synthesis

The conditions required for nucleic acid synthesis are well known in the art. The polymerase reaction conditions include the type and concentration of buffer, the pH of the reaction, the temperature, the type and concentration of salts, the presence of particular additives that influence the kinetics of the enzyme, and the type, concentration, and relative amounts of various cofactors, including metal cofactors. For carrying out the methods of the instant invention, the conditions for polymerase mediated nucleic acid synthesis must also be compatible with conditions for measuring electrical signals at the nanoFET. One aspect of carrying out electrical measurements in solution is controlling the ionic strength of the medium. It is know that polymerase enzymes can effectively operate over a range of ionic strengths, and that the ionic strength can be varied by changing the levels of monovalent ions such as Li+, Na+, K+, Rb+, or Cs+. As has been shown, the amount of one or more of these cations can have an effect on the kinetics of the polymerase, and that the kinetic behavior can be tuned by varying the relative amounts of these ions. Using combinations of these ions, conditions can be chosen where both the kinetic parameters of the enzyme, and the ionic strength for electrical detection can be useful for the instant methods. See, e.g. U.S. Patent Application 20120009567 which is incorporated herein by reference for all purposes.

Enzymatic reactions are often run in the presence of a buffer, which is used, in part, to control the pH of the reaction mixture. Buffers suitable for the invention include, for example, TAPS (3-{[tris(hydroxymethyl)methyl]amino}propanesulfonic acid), Bicine (N,N-bis(2-hydroxyethyl)glycine), TRIS (tris(hydroxymethyl)methylamine), ACES (N-(2-Acetamido)-2-aminoethanesulfonic acid), Tricine (N-tris(hydroxymethyl)methylglycine), HEPES 4-2-hydroxyethyl -1-piperazineethanesulfonic acid), TES (2-{[tris(hydroxymethyl)methyl]amino}ethanesulfonic acid), MOPS (3-(N-morpholino)propanesulfonic acid), PIPES (piperazine-N,N'-bis(2-ethanesulfonic acid)), and MES (2-(N-morpholino)ethanesulfonic acid).

The pH of the reaction can influence the rate of the polymerase reaction. The temperature of the reaction can be adjusted to enhance the performance of the system. The reaction temperature may depend upon the type of polymerase which is employed.

Nucleotide Analogs

Nucleotide analogs comprising conductivity labels will typically be larger, i.e. have a larger molecular weight than natural nucleotides. These analogs can include, for example, nucleotide analogs describe in US. patent application Ser. No. 13/767,619 entitled Polymerase Enzyme Substrates with Protein Shield, filed Feb. 14, 2013, and in U.S. Patent Application 61/862,502, entitled Protected Fluorescent Reagent Compounds, which are incorporated herein by reference for all purposes.

Components of the sequencing reaction mixture include nucleotides or nucleotide analogs. For the methods of the instant invention, at least some of the nucleotide analogs have conductivity labels attached to them. The nucleotide analogs comprising conductivity labels are generally constructed in order to enhance the electrical signal at the nanoFET when the label is in the enzyme active site.

Typically the nucleotide analogs of the invention have the following structure:

$$\text{Base-Sugar-PP-Linker-Label}$$

wherein Base is a nucleobase, Sugar is a sugar such as ribose or deoxyribose, PP is a polyphosphate moiety, Linker is a linking group, and the Label is a group that is detectable by the nanoFET. The label can be for example, a conductivity label as described herein.

Typically there are four nucleotides in a sequencing reaction mixture corresponding to A, G, T, and C for DNA and A, G, C, U for RNA. In some cases, a $5^{th}$, $6^{th}$, or more base is included. In some cases all of the nucleotide analogs have a conductivity label, in other cases, fewer than all of the nucleotides will have a conductivity label. In still other cases all of the different nucleotide analog types will carry a conductivity label, but a particular conductivity label will be assigned to more than one base type. Typically each of the types of nucleotide will have a nucleotide that is different and can be distinguished from the other nucleotides, for example the other three nucleotides. As described herein, the different nucleotides can exhibit different impedance intensities, different impedance versus frequency characteristics, different current versus time characteristics (current oscillation color), or different combinations of two or more of the above.

The Base is a nucleobase which can be one of the natural bases, a modified natural base or a synthetic base. The Base will selectively associate with its complementary base on the template nucleic acid such that it will be inserted across from its complementary base. The sugar is a group that connects the base to the polyphosphate group. It is typically either ribose or deoxyribose, but can be any sugar or other group that allows for the complexation and incorporation of the nucleotide analog into the growing strand. PP is a polyphosphate group generally from 2 to 20 phosphates in length, typically from 3 to 12 phosphates in length, and in some preferred embodiments from 4 to 10 phosphates in length. The nucleotide analog can have for example 4, 5, 6, 7 or more phosphate groups. Such nucleotides have been described, for example, in U.S. Pat. Nos. 6,936,702 and 7,041,812, which are incorporated herein by reference for all purposes. Together, the Base, Sugar and PP portion of the nucleotide analog is sometimes referred to as the nucleotide portion or nucleoside phosphate portion.

As used in the art, the term nucleotide refers both to the nucleoside triphosphates that are added to a growing nucleic acid chain in the polymerase reaction, or can refer to the individual units of a nucleic acid molecule, for example the units of DNA and RNA. Herein, the term nucleotide is used consistently with its use in the art. Whether the term nucleotide refers to the substrate molecule to be added to the growing nucleic acid or to the units in the nucleic acid chain can be derived from the context in which the term is used.

The Linker is a linking group that connects the label to the nucleotide portion of the nucleotide analog. The linker can be long linear or branched moiety whose length and flexibility is used to control the diffusion of the nucleotide analog that is held within the polymerase enzyme while it is being incorporated. The length of the linker is, for example, from between 2 nm and 200 nm when fully extended. It is understood that a long molecule such as a polymer will not spend much time, if any, in its fully extended configuration. The linker can be made up of groups including alkanes, ethers, alcohols, amines, acids, sulfates, sulfonates, phosphates, phosphonates, amides, esters, peptides, and sugars. The groups on the linker can be neutral, positively charged, or negatively charged. In some cases, the linker comprises polyethylene glycol (PEG). It is desirable that the linker have a fixed length (i.e. not be polydisperse) such that the size of any analog molecule in the population will be the same. It is generally desirable that the linker be water compatible. In some cases the linker can include one or more macromolecules, such as proteins, or one or more nanoparticles.

In some, the covalent attachment site is far from the active site, but the linker is long, e.g., more than 5 nm, or more than 10 nm or more than 20 nm, allowing the active site to spend some amount of time in proximity to the detection zone. When a long linker is used, rotational freedom of the polymerase permits the active site to enter the detection zone of the nanotube. In one preferred example of this method, a covalent attachment is provide at a location on the enzyme surface that is convenient (for example the c or n terminus) and an affinity label is engineered into a residue near the active site (375, 512 or near as before) to bias the orientation. This strategy provides a degree of freedom in the construction of the enzyme.

The length or size of the linker can be chosen for performance with the particular geometry of the nanoFET device that is used. The conductivity label is tethered to the the nucleotide analog (comprising the linker), the enzyme and the attachment moiety. The length of this complete tether and the distance of the polymerase complex from the nanoFET can be used in order to select the appropriate linker.

The conductivity label is attached to the nucleotide portion of the nucleotide analog through the linker and phosphate. The linker is typically attached to the terminal phosphate in the polyphosphate moiety, but in some cases can be connected to a phosphate in the polyphosphate chain that is not the terminal phosphate. The linker is typically attached to a phosphate that is cleaved on the act of the polymerase enzyme of nucleotide incorporation. The polymerase enzyme cleaves the polyphosphate between the alpha and beta phosphates, thus, the linker should be connected to the beta (second) phosphate or greater.

The impedance label may be made up of one or more moieties that provide a measurable electrical signal at the gate of the nanoFET. Acceptable labels or moieties can comprise organic compounds, organometallic compounds, nanoparticles, metals, or other suitable substituent.

In some embodiments, a nanotube binding component is attached to the nucleotide analog. Exemplary useful nanotube binding components are described hereinabove and include, e.g., a polymeric agent (e.g., a protein) or non-polymeric component (e.g., a polycyclic aromatic moiety such as naphthalene). Nanotube binding components with a wide range of binding affinities can be used, so long as the aggregate kinetics of binding and unbinding are fast compared with the residence time of a typical terminal phosphate label on a nucleotide analog that is participating in a nucleotide incorporation event. Typically, however, components with a relatively low affinity for the nanotube are preferred, to minimize background from interaction with the nanotube alone rather than with both the polymerase and nanotube. When present, the nanotube binding component can, e.g., be incorporated in a linker between the polyphosphate and the label, within the label moiety, or terminal to the label.

Kinetic Measurements—Modified Base Detection

The methods of the invention provide for measuring the incorporation of nucleotides into a growing chain in real time. The real time measurements allow for the determination of enzyme kinetics, which are can be sensitive to template characteristics such as secondary structure, and modified bases. The ability to detect modifications within nucleic acid sequences is useful for mapping such modifications in various types and/or sets of nucleic acid sequences, e.g., across a set of mRNA transcripts, across a chromosomal region of interest, or across an entire genome. The modifications so mapped can then be related to transcriptional activity, secondary structure of the nucleic acid, siRNA activity, mRNA translation dynamics, kinetics and/or affinities of DNA- and RNA-binding proteins, and other aspects of nucleic acid (e.g., DNA and/or RNA) metabolism.

In certain aspects of the invention, methods are provided for identification of a modification in a nucleic acid molecule using real time nanoFET sequencing. In general, a template nucleic acid comprising the modification and an enzyme capable of processing the template are provided. The template nucleic acid is contacted with the enzyme, and the subsequent processing of the template by the enzyme is monitored. A change in the processing is detected, and this change is indicative of the presence of the modification in the template. Exemplary modifications that can be detected by the methods of the invention include, but are not limited to methylated bases (e.g., 5-methylcytosine, N6-methyladenosine, etc.), pseudouridine bases, 7,8-dihydro-8-oxoguanine bases, 2'-O-methyl derivative bases, nicks, apurinic sites, apyrimidic sites, pyrimidine dimers, a cis-platen cross-linking products, oxidation damage, hydrolysis damage, bulky base adducts, thymine dimers, photochemistry reaction products, interstrand crosslinking products, mismatched bases, secondary structures, and bound agents. In preferred embodiments, nucleotides or analogs thereof that are incorporated into a nascent strand synthesized by the enzyme are distinctly labeled to allow identification of a sequence of specific nucleotides or nucleotide analogs so incorporated. Labels are linked to nucleotides or nucleotide analogs through a phosphate group, e.g., a phosphate group other than the alpha phosphate group. As such, the labels are removed from the nucleotide or nucleotide analog upon incorporation into the nascent strand. Techniques for kinetically identifying modified bases are described, for example in U.S. Patent Application 20110183320 Classification of Nucleic Acid Templates which is incorporated herein by reference for all purposes.

The term "modification" as used herein is intended to refer not only to a chemical modification of a nucleic acids, but also to a variation in nucleic acid conformation or composition, interaction of an agent with a nucleic acid (e.g., bound to the nucleic acid), and other perturbations associated with the nucleic acid. As such, a location or position of a modification is a locus (e.g., a single nucleotide or multiple contiguous or noncontiguous nucleotides) at which such modification occurs within the nucleic acid. For a double-stranded template, such a modification may occur in the strand complementary to a nascent strand synthesized by a polymerase processing the template, or may occur in the displaced strand. Although certain specific embodiments of the invention are described in terms of 5-methylcytosine detection, detection of other types of modified nucleotides (e.g., $N^6$-methyladenosine, $N^3$-methyladenosine, $N^7$-methylguanosine, 5-hydroxymethylcytosine, other methylated nucleotides, pseudouridine, thiouridine, isoguanosine, isocytosine, dihydrouridine, queuosine, wyosine, inosine, triazole, diaminopurine, β-D-glucopyranosyloxymethyluracil (a.k.a., β-D-glucosyl-HOMedU, β-glucosyl-hydroxymethyluracil, "dJ," or "base J"), 8-oxoguanosine, and 2'-O-methyl derivatives of adenosine, cytidine, guanosine, and uridine) are also contemplated. Further, although described primarily in terms of DNA templates, such modified bases can be modified RNA bases and can be detected in RNA (or primarily RNA) templates. These and other modifications are known to those of ordinary skill in the art and are further described, e.g., in Narayan P, et al. (1987) Mol Cell Biol 7(4):1572-5; Horowitz S, et al. (1984) Proc Natl Acad Sci U.S.A. 81(18):5667-71; "RNA's Outfits: The nucleic acid has dozens of chemical costumes," (2009) C&EN; 87(36): 65-68; Kriaucionis, et al. (2009) Science 324 (5929): 929-30; and Tahiliani, et al. (2009) Science 324 (5929): 930-35; Matray, et al. (1999) Nature 399(6737):704-8; Ooi, et al. (2008) Cell 133: 1145-8; Petersson, et al. (2005) J Am Chem Soc. 127(5):1424-30; Johnson, et al. (2004) 32(6):1937-41; Kimoto, et al. (2007) Nucleic Acids Res. 35(16):5360-9; Ahle, et al. (2005) Nucleic Acids Res 33(10):3176; Krueger, et al., Curr Opinions in Chem Biology 2007, 11(6):588); Krueger, et al. (2009) Chemistry & Biology 16(3):242; McCullough, et al. (1999) Annual Rev of Biochem 68:255; Liu, et al. (2003) Science 302(5646):868-71; Limbach, et al. (1994) Nucl. Acids Res. 22(12):2183-2196; Wyatt, et al. (1953) Biochem. J. 55:774-782; Josse, et al. (1962) J. Biol. Chem. 237:1968-1976; Lariviere, et al. (2004) J. Biol. Chem. 279:34715-34720; and in International Application Publication No. WO/2009/037473, the disclosures of which are incorporated herein by reference in their entireties for all purposes. Modifications further include the presence of non-natural base pairs in the template nucleic acid, including but not limited to hydroxypyridone and pyridopurine homo- and hetero-base pairs, pyridine-2,6-dicarboxylate and pyridine metallo-base pairs, pyridine-2,6-dicarboxamide and a pyridine metallo-base pairs, metal-mediated pyrimidine base pairs T-Hg(II)-T and C-Ag(I)-C, and metallo-homo-basepairs of 2,6-bis(ethylthiomethyl)pyridine nucleobases Spy, and alkyne-, enamine-, alcohol-, imidazole-, guanidine-, and pyridyl-substitutions to the purine or pyridimine base (Wettig, et al. (2003) J Inorg Biochem 94:94-99; Clever, et al. (2005) Angew Chem Int Ed 117:7370-7374; Schlegel, et al. (2009) Org Biomol Chem 7(3):476-82; Zimmerman, et al. (2004) Bioorg Chem 32(1):13-25; Yanagida, et al. (2007) Nucleic Acids Symp Ser (Oxf) 51:179-80; Zimmerman (2002) J Am Chem Soc 124(46): 13684-5; Buncel, et al. (1985) Inorg Biochem 25:61-73; Ono, et al. (2004) Angew Chem 43:4300-4302; Lee, et al. (1993) Biochem Cell Biol 71:162-168; Loakes, et al. (2009), Chem Commun 4619-4631; and Seo, et al. (2009) J Am Chem Soc 131:3246-3252, all incorporated herein by reference in their entireties for all purposes). Other types of modifications include, e.g., a nick, a missing base (e.g., apurinic or apyridinic sites), a ribonucleoside (or modified ribonucleoside) within a deoxyribonucleoside-based nucleic acid, a deoxyribonucleoside (or modified deoxyribonucleoside) within a ribonucleoside-based nucleic acid, a pyrimidine dimer (e.g., thymine dimer or cyclobutane pyrimidine dimer), a cis-platin crosslinking, oxidation damage, hydrolysis damage, other methylated bases, bulky DNA or RNA base adducts, photochemistry reaction products, interstrand crosslinking products, mismatched bases, and other types of "damage" to the nucleic acid. As such, certain embodiments described herein refer to "damage" and such damage is also considered a modification of the nucleic acid in accordance with the present invention. Modified nucleotides can be caused by exposure of the DNA to radiation (e.g., UV), carcinogenic chemicals, crosslinking agents (e.g., formaldehyde), certain enzymes (e.g., nickases, glycosylases, exonucleases, methylases, other nucleases, glucosyltransferases, etc.), viruses, toxins and other chemicals, thermal disruptions, and the like. In vivo, DNA damage is a major source of mutations leading to various diseases including cancer, cardiovascular disease, and nervous system diseases (see, e.g., Lindahl, T. (1993) Nature 362(6422): 709-15, which is incorporated herein by reference in its entirety for all purposes). The methods and systems provided herein can also be used to detect various conformations of DNA, in particular, secondary structure forms such as hairpin loops, stem-loops, internal loops, bulges, pseudoknots, base-triples, supercoiling, internal hybridization, and the like; and are also useful for detection of agents interacting with the nucleic acid, e.g., bound proteins or other moieties.

In some embodiments, five color DNA sequencing can be carried out by the sequencing methods of the invention. Five color sequencing generally utilizes a nucleotide analog having a base that preferentially associates with a fifth base in the template or an abasic site. Such five color sequencing is described for example in U.S. Patent Application 20110183320, which is incorporated herein by reference in its entirety for all purposes.

It will be apparent to the ordinary artisan that although various strategies herein are described independently, they can also be used in combination in certain embodiments. For example, as noted above, a strategy for extend the zone of sensitivity to the charge of interest can be combined with a strategy for bringing the charge of interest to the nanowire. Further, an embodiment can include a reference nanowire as well as an attachment that positions an active site of a polymerase proximal to a nanowire. Different types of conductance labels can be combined with different types of protein immobilization strategies. As such, combinations of the strategies are contemplated and within the scope of the invention.

Monitoring Biological Reactions

While the nanoscale devices and systems of the invention are described throughout most of this application for use in nucleic acid sequencing, it is to be understood that the devices and systems can also find use in other analytical reactions including monitoring biological reactions in real time, in particular monitoring the interactions of biological molecules at the single molecule level. The ability to analyze such reactions provides an opportunity to study those reactions as well as to potentially identify factors and/or approaches for impacting such reactions, e.g., to stimulate, enhance, or inhibit such reactions.

The invention provides for observation of the interaction of two or more specifically interacting reactants at the single molecule (or single molecular complex) level in order to monitor the progress of the interaction separately from other interactions. In other words, a single immobilized reaction component can be monitored at a single reaction site on a support such that electrical signals received from that reaction site are resolvable from other immobilized reaction components at other reaction sites on that support. In preferred embodiments, the methods monitor labels with a nanoFET device, such that a single reactant comprising a label is distinguishable from a different single reactant comprising a different label. A plurality of analytical reactions may also be carried out in an array of nanoFET devices. Analytical reactions in an array of nanoFET devices can be carried out simultaneously, and may or may not be synchronized with one another. In such an array, multiple reactions can therefore be monitored simultaneously and independently.

The monitoring typically comprises providing the interaction with one or more signaling events that are indicative of one or more characteristics of that interaction. Such signaling events may comprise the retention of a labeled reactant proximate to a given nanoFET device. For example, in some embodiments, the labels provide electrical signals that are detected by a detection system operably linked to a reaction site at which the analytical reaction is taking place. As used herein, a reaction site is a location on or adjacent to a substrate at which an analytical reaction is monitored, and may refer to, e.g., a position on the substrate at which one or more components of an analytical reaction are immobilized or to a "detection volume" within which an analytical reaction is monitored. The detected signals are analyzed to determine one or more characteristics of the analytical reaction, e.g., initiation, termination, affinity, biochemical event (e.g., binding, bond cleavage, conformational change, etc.), substrate utilization, product formation, kinetics of the reaction (e.g., rate, time between subsequent biochemical events, time between the beginning/end of subsequent biochemical events, processivity, error profile, etc.), and the like.

These characteristics may generally be broken into two categories: reactant characteristic(s) and interaction characteristic(s). Reactant characteristic(s) includes characteristics of a particular reactant, e.g., type/identity of reactant, concentration of the reactant, a label on the reactant, etc. Interaction characteristic(s) includes characteristics of a given interaction between multiple reactants, e.g., rates, constants, affinities, etc., and is typically determined based on reaction data gathered during such an interaction. For example, some characteristics of a polymerization reaction include the identity of a monomer incorporated into a growing polymer, the rate of incorporation, length of time the polymerase is associated with the template, and the length of the polymer synthesized. In some embodiments, various different components of an analytical reaction (e.g., different types of monomers) are differentially labeled to allow each labeled component to be distinguished from other labeled components during the course of the reaction. For example, incorporation of monomer A into a polymer can be distinguished from incorporation of monomer B.

In certain preferred embodiments, multiple characteristics of a reaction are monitored and/or determined. For example, these may be multiple characteristics of one or more reaction components (e.g., identity, concentration, etc.; "reactant characteristic(s)"), one or more characteristics of an interaction between two or more reaction components (e.g., related to product formation, kinetics of the reaction, binding or dissociation constants, etc.; "interaction characteristic(s)"), or, preferably, a combination reactant characteristic(s) and interaction characteristic(s).

In some embodiments, a reaction mixture comprises a plurality of types of non-immobilized binding partners, and a characteristic determined is the particular type of one of the non-immobilized binding partners, e.g., that associates with a particular reaction site. Typically, the conductivity label is attached to the non-immobilized binding partner through a linking group as described herein such that the label on the non-immobilized binding partner will be sensed when it is interacting with the immobilized binding partner that is immobilized proximate to a nanoscale electrode or electrodes. In some embodiments, an array of reaction sites comprises a plurality of types of immobilized binding partners, each at a different reaction site, and a characteristic is determined that identifies which type of immobilized binding partner is located at each of the different reaction sites. In some embodiments, an array of reaction sites comprising a plurality of types of immobilized binding partners, each at a different reaction site, is contacted with a reaction mixture comprising a plurality of types of non-immobilized binding partners; characteristics determined during the reaction serve to both identify which of the types of immobilized binding partners is located at each reaction site and which of the types of non-immobilized binding partners associate with the immobilized binding partners. In some cases, the specificity of the interaction between the non-immobilized and immobilized binding partners is high enough that detection of a label on a non-immobilized binding partner residing at a particular reaction site is sufficient to identify the immobilized binding partner at that reaction site. In some embodiments, a characteristic is determined that quantifies a particular aspect of an interaction between reaction components, e.g., affinity between an immobilized binding partner and a non-immobilized binding partner, a rate of catalysis of a reaction, or other aspects of the interaction. In some cases, different electronic signaling events (e.g., different labels on one or more reaction components) are used to monitor or determine different characteristics of a reaction under observation, but in some embodiments a single electrical signaling event can provide more than one type of characteristic information. For example, if a non-immobilized binding partner has a label that not only identifies it from a plurality of different non-immobilized binding partners, but also provides kinetic information about the reaction based on various parameters monitored in real time, e.g., the time it takes for binding to occur, the time it remains associated with the reaction site, the on/off rate, etc.

In some embodiments, multiple different interactions or reactions can occur and be monitored simultaneously or sequentially, where each individual interaction is monitored separately from every other, e.g. in an electronic element such as a nanoFET, such that there is resolution between different interactions under observation. For example, multiple different non-immobilized reaction components may simultaneously or sequentially interact with an immobilized reaction component; e.g., the multiple different non-immobilized reaction components can be different non-immobilized binding partners for an immobilized binding partner, or different agents that may alter an interaction between two reaction components, or different monomers for incorporation into a polymer being synthesized at the reaction site. In other embodiments, an interaction between a non-immobilized reaction component and a product of a synthesis reaction occurs during the synthesis reaction, e.g., once the product is suitable for such interaction. For example, the product may need to be of a certain length, or in a certain conformation (e.g., in a particular higher-order structure) to be suitable for interaction with the non-immobilized reaction component. Alternatively, a synthesis reaction can be performed at a reaction site, and subsequently exposed to a reaction mixture comprising non-immobilized reaction components that can then interact with the product of the synthesis reaction, which is preferably immobilized at the reaction site. In preferred embodiments, the synthesis reaction is monitored to determine characteristics of the product (e.g., length, chemical composition, etc.) being synthesized. Knowledge of characteristics of the product of synthesis combined with the detection of an interaction with a particular reaction component provides additional characteristics, e.g., the binding site for the particular reaction component. Examples of biological interactions that can be measured with the nanoFET devices and systems of the invention are described, for example, in U.S. 2010/0323912 Patent Application Real-Time Analytical Methods and Systems which is incorporated herein by reference for all purposes.

Systems

In some aspects, the invention provides a system for sequencing template nucleic acids that has a housing with housing electrical connection sites. The housing electrical connection sites are made to connect with electrical connections on the chip for providing electrical signals to the chip and for receiving electrical signals from the chip. There is a chip that reversibly mates with the housing. The chip is a nanoFET chip as described herein. The system includes an electronic control system electrically connected to the nanoFET devices through the electrical connections to apply desired electrical signals to the nanoFETs and for receiving electrical signals from the nanoFET devices. The system typically has a computer that receives information on the electrical signals at the nanoFETs over time and uses such information to identify a sequence of the template nucleic acid. The computer can also control the performance of the chip, for example, by providing a sequence of electrical signals to the nanoFETs on the chip.

In some aspects, the invention provides systems for carrying out real time single molecule electronic sequencing using nanoFET devices. A nanoFET measuring system is used to monitor the nanoFET over time, allowing for the determination of whether a nucleotide analog having a conductivity label is associating with the enzyme. That is, the nanoFET element and enzyme are configured such that the freely diffusing conductivity labeled nucleotide analogs in the solution are not substantially detected at the nanoFET. Only when a label is brought into the vicinity of the nanoFET due to its association with the polymerase enzyme is the label detected and identified as an incorporated nucleotide. One distinction between the freely diffusing nucleotide analogs and an analog in the active site of the enzyme is the amount of time spent proximate to the nanoFET. Diffusing nucleotide analogs will be quickly diffusing in and out of the vicinity of the nanoscale electrode, while the nucleotide analog to be incorporated will spend a longer amount of time, for example on the order of milliseconds proximate to the nanoscale electrode. Thus, the nanoFET measuring system will detect the presence of a nucleotide analog which is to be incorporated into the growing nucleic acid chain while it is in the active site of the enzyme. When the nucleotide is incorporated into the growing strand, the label, which is attached to the phosphate portion of the nucleotide analog is cleaved and diffuses away from the enzyme and the electrode. Thus, the system determines the presence of the analog in the active site prior to incorporation. In addition, the identity of the distinct label is determined, e.g. by the magnitude of a change in an electrical property at the gate of the electrode. As the polymerase reaction continues and is monitored by the nanoFET measuring system, the sequence of the template nucleic acid can be determined by the time sequence of incorporation of the complementary nucleotide analog into the growing nucleic acid strand.

The systems of the invention include a chip comprising an array of nanoFETs as described herein that is reversibly mated with other system components. The chip with array of nanoFET devices can be a single use chip or the chip can be used multiple times. The system typically has a housing into which the chip is placed. The housing has electrical connectors that provide reversible connections to the electrical connections on the chip. Sockets that provide reliable reversible electrical connections to chips inserted into the socket are well known. Electrical connections to the top, sides, bottom, or a combination of these sides can be used.

When the chip is inserted into the housing, the system provides a fluid reservoir to which fluid comprising the sequencing reaction mixture is added. In some cases, the fluid reservoir is included as part of the chip. In some cases, part of the fluid reservoir is associated with the housing, such that the insertion of the chip forms the reservoir. The fluid reservoir can be, for example a well or a chamber into which fluid can be introduced. The introduced fluid sequencing reaction mixture comes into contact with the nanoFET devices on the surface of the chip. The system will typically include environmental control components including temperature control and control of a vapor phase above the fluid. The chemical makeup and the temperature of the vapor can be controlled, for example by providing a flow of inert gas over the reaction mixture to minimize oxidation of the sample. In some cases the system can have fluid handling systems for delivering and removing components to the fluid reservoir before, during, or after performing the sequencing reaction.

In some cases the fluid reservoir will also provide contact of the sequencing reaction mixture with the either or both of a reference electrode or counter electrode. As described above, in order to carry out the method, in some cases a reference electrode, a counter electrode, or both are used. In some one or more of these electrodes are on the chip. Where the reference electrode and/or counter electrode are used, and not on the chip, they are brought into contact with the sequencing reaction mixture in the fluid reservoir.

Connected to the chip through the connectors on the housing are the electronics for providing voltage to the nanoFET and for measuring the electronic signals at the gate, for example, a current/voltage source and a meter. For example, the source can provide the current and voltage to bring the electrodes to a proper alternating current signal over time to carry out the methods of the invention. The meter can be used to measure the electrical signals. In some cases, the source and meter are combined into a single unit. In some cases each of the electronic elements in the array on the chip are addressed by a separate source and separate meter component within the system. In some cases, multiplexing is used so a single source can drive multiple electronic elements. In some cases a single source will drive all of the electronic elements on a chip, while each of the electronic elements is measured with a separate meter component. Any suitable combination of sources and meters can be used.

A computer control and analysis system is typically used to control both the input voltages and currents and to provide computer-implemented control functions, e.g., controlling robotics, environmental conditions, and the state of various components of the system. The computer control system also includes components for computational data analysis (e.g., for single molecule sequencing applications, determining and characterizing nucleotide incorporation events). As described above, in some cases, some of the control functions can be implemented on the chip, in particular controlling source wave functions, or handling electrical signals from the nanoFET devices on the chip. In some cases the computer control and analysis system provides substantially all of the control of the signals to and from the chip, and the chip simple acts as an electronic element from which information related to the electronic signal is extracted. In some cases, the chip can take on some of the functionality of control and analysis. The chip can process the analog data from the electronic elements. The chip can also have analog to digital components, and can perform analysis and storage functions for the digital signals. The decision on how much functionality is implemented on the chip and how much is retained with the computer control and analysis system can be made based on the relative functionality gained versus the cost of adding the functionality.

Also provided is a user interface operatively coupled to the components for computational data, permitting a user of the system to initiate and terminate an analysis, control various parameters (e.g., with respect to analysis conditions, sequencing reaction mixture environment, etc.), and manage/receive data (e.g., nucleic acid sequence data) obtained by the system. In some aspects, the user interface is attached the computer control and analysis system. Additionally, remote user interfaces can be provided that are in communication with the overall system via a wireless network. Such user input devices may include other purposed devices, such as notepad computers, e.g., Apple iPad, or smartphones running a user interface application. Optionally, the user interface includes a component, e.g., a data port, from which the user can receive data obtained by the analysis system to a portable electronic storage medium for use at location other than the location of the substrate analysis system.

Aspects of the present invention are directed to machine or computer implemented processes, and/or software incorporated onto a computer readable medium instructing such processes. As such, signal data generated by the reactions and systems described above, is input or otherwise received into a computer or other data processor, and subjected to one or more of the various process steps or components set forth herein. Once these processes are carried out, the resulting output of the computer implemented processes may be produced in a tangible or observable format, e.g., printed in a user readable report, displayed upon a computer display, or it may be stored in one or more databases for later evaluation, processing, reporting or the like, or it may be retained by the computer or transmitted to a different computer for use in configuring subsequent reactions or data processes.

Computers for use in carrying out the processes of the invention can range from personal computers such as PC or Macintosh® type computers running Intel Pentium or Duo-Core processors, to workstations, laboratory equipment, or high speed servers, running UNIX, LINUX, Windows®, or other systems. Logic processing of the invention may be performed entirely by general purposes logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other convenient formats, while video based formats, such as avi, mpeg, mov, rmv, or other video formats may be employed. The software processes of the invention may generally be programmed in a variety of programming languages including, e.g., Matlab, C, C++, C#, NET, Visual Basic, Python, JAVA, CGI, and the like.

Use of Allosteric Signal for Sequence Reads

The polymerase enzyme attached to the nanotube undergo regular repeated motions during the sequencing process. It has been shown that allosteric motions of enzymes can be detected in nanotube to which the enzymes are attached, see U.S. Pat. No. 9,164,053 and U.S. Patent Application No. 2013/0078622 which are incorporated by reference herein for all purposes. The motions of a polymerase enzyme are characteristic of the polymerase activity of incorporating nucleic acid analogs. An aspect of the instant invention is the use these allosteric signals of enzyme movement during nucleic acid polymerization as a measure of nucleotide incorporation events. This incorporation event detection can be used in conjunction with the signal from the conductivity label to provide a more accurate measure of the sequence of the template nucleic acid. For example, in some cases it can be difficult to know if a conductivity label signal corresponds to a single incorporation of a nucleotide, or corresponds to multiple nucleotide incorporations in a row. By providing an independent measure of nucleotide incorporation events, the allosteric signal provides a means to determine how many incorporation events have occurred, providing greater accuracy.

These methods are particularly useful for sequencing homopolymer regions, for which knowing whether a single nucleotide or multiple nucleotides have been incorporated is important and sometimes challenging. In some cases, the allosteric signal corresponds to a translocation step of the polymerase enzyme. In some cases, this signal occurs primarily during an incorporation event. In some cases, the signal occurs primarily between incorporation events. In some cases, the signal occurs primarily from signal observed during both the pulse and the time between pulses. In some cases, it is not the characteristics of a particular step in the enzyme catalytic cycle, but a characteristic set of signals as the enzyme cycles through the various conformations that is used to determine that an incorporation reaction has occurred. Signal deconvolution can be used to separate this periodic nucleotide incorporation signature from random noise and from conductivity label signals.

In some cases, different nucleotide analogs that produce varying degrees of base-specific allosteric shifts in the structure of the polymerase are chosen and used as sequencing substrates the enzyme will use to synthesize a nascent strand. The difference in the allosteric shifts for the different nucleotide analogs can then be used to distinguish between the different bases for base calling.

In some cases, the detection of incorporation is reliable enough to provide for three base sequencing in which the detection of an incorporation event without a conductivity label signal is known to correspond to the incorporation of the fourth, unlabeled nucleotide.

Polymerase enzyme engineering approaches known in the art and described herein can be used to enhance and optimize the allosteric signal. For example, positive and/or negative charges can be incorporated onto the surface of the polymerase enzyme to increase the electrical field change in the vicinity of the nanotube surface.

Lowered Background Noise—Tangential Field

In some cases, the nucleic acid associated with the polymerase interacts with the nanotube creating background noise. The nucleic acid associated with the polymerase includes both the template strand and nascent strand. The nucleic acid associated with the polymerase will be moving around as a polymeric molecule do in the liquid (solvated) state. As the nucleic acid is moving around it can enter into the vicinity of or come into contact with the nanotube, potentially producing a change in conductivity that can be confused with the signal from conductivity labels.

We have found that providing a field that extends the nucleic acid away from the nanotube can be useful in reducing this noise. The field can be provided in any suitable orientation. We have found that in some preferred embodiments, the field is provided substantially tangential or parallel to the surface on which the nanoFETs reside. The tangential field pulls the nucleic acid away from the nanotube across the surface of the chip. The field can be any suitable field that results in the elongation of the nucleic acid away from the nanotube. Suitable fields include electric fields and fluid flow fields.

Figure 22:
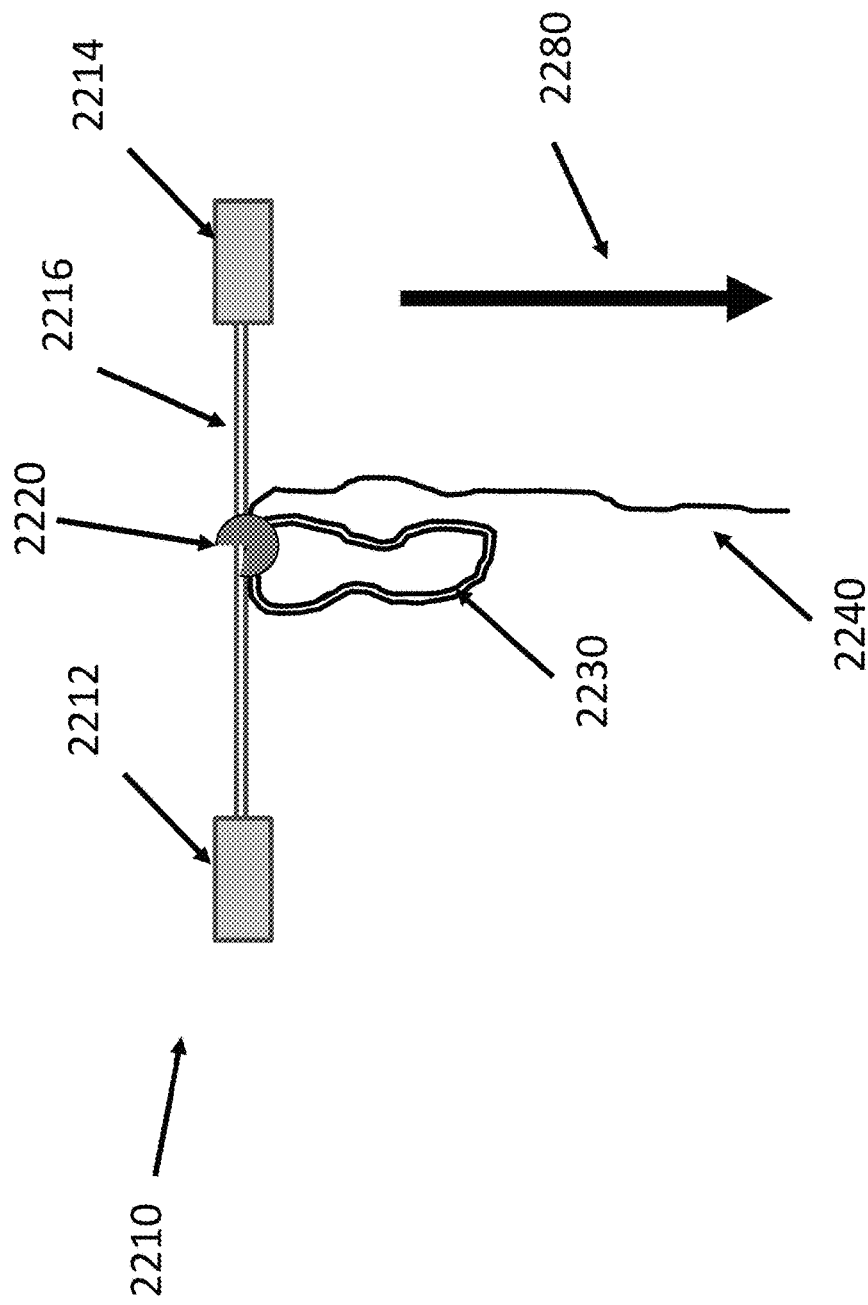
FIG. 22 shows an embodiment of providing a tangential flow field to pull the nucleic acid associated with the polymerase away from the nanotube to reduce background noise.

FIG. 22 shows an embodiment of providing a tangential flow field to pull the nucleic acid associated with the polymerase away from the nanotube to reduce background noise. FIG. 22 is a view from above the surface of a chip showing one nanoFET device 2210 on the chip. The nanoFET has a nanotube 2216 connected to source and drain electrodes 2212 and 2214. A single polymerase enzyme 2220 is attached to the nanotube 2216. The single polymerase enzyme 2220 is complexed with a template nucleic acid 2230, and is actively synthesizing nascent nucleic acid strand 2240. The template strand 2230 shown here is circular, but in some cases linear template strands can be used. The field 2280 is applied substantially tangential to the surface of the chip. In some cases, as shown here, the field 2280 is also applied substantially perpendicular to the carbon nanotube 2216. The nucleic acid molecules 2230 and 2240 elongate in the field, minimizing the amount that the motions of the nucleic acid molecules will cause the nucleic acids interact with the surface of the nanotube, causing background. The field is preferably an electric field. The field can be produced by appropriately oriented electrodes. In some cases, the electrodes that provide the orientation field are also on the chip.

Figure 23:
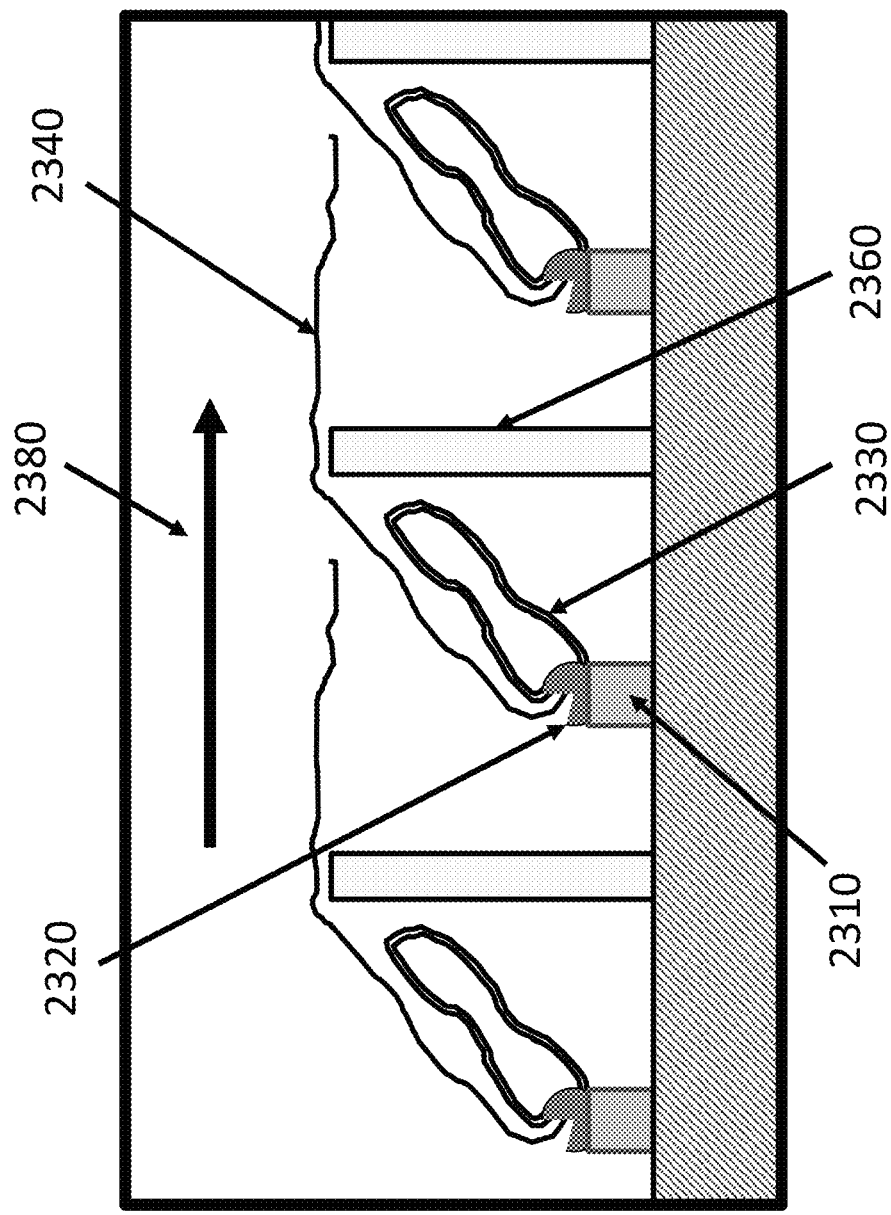
FIG. 23 shows a device having walls are erected between rows of nanoFET devices and having a tangential field applied.

In some cases, the electrical field can extend the nucleic acid molecules far enough away from a nanoFET on the surface that the molecules will interfere with an adjacent nanoFET. One approach to this issue is to stagger the nanoFETs in each row, such that there is no nanoFET in the next row in the region where the field will pull the nucleic acid strands. In some cases, surface structures can be provided to the chip that divert the extended nucleic acid from interaction with nearby nanoFET structures. FIG. 23 shows one use of such surface structures on the chip. Here, walls are erected between rows of nanoFET devices. The walls have dimensions such that any nucleic acid aligned in the flow field will extend above the nearby nanoFET, minimizing any interaction between the extended nucleic acid and the nanoFET neighbor. FIG. 23 shows a cross section of a chip that show three rows of nanoFETs. The nanotubes are oriented into the page, so are not seen in the figure. For example, they extend down into the page from electrode 2310. The nanoFETs have two electrodes connected by a nanotube, there is one single polymerase enzyme 2320 attached to the nanotube. Template nucleic acid 2330 and nascent strand 2340 are complexed with the polymerase enzyme 2320. During sequencing, the polymerase enzyme 2320 is actively adding nucleotides and extending nascent strand 2340. A field 2380, such as an electric field, is provided substantially tangential to the surface of the chip. Here, the field is also substantially perpendicular to the nanotubes. As the field elongates the nucleic acid molecules, they extend over the top of the walls 2360. The walls have dimensions such that the interaction of the elongated nucleic acid molecules with neighboring nanoFETs is minimized.

Figure 24:
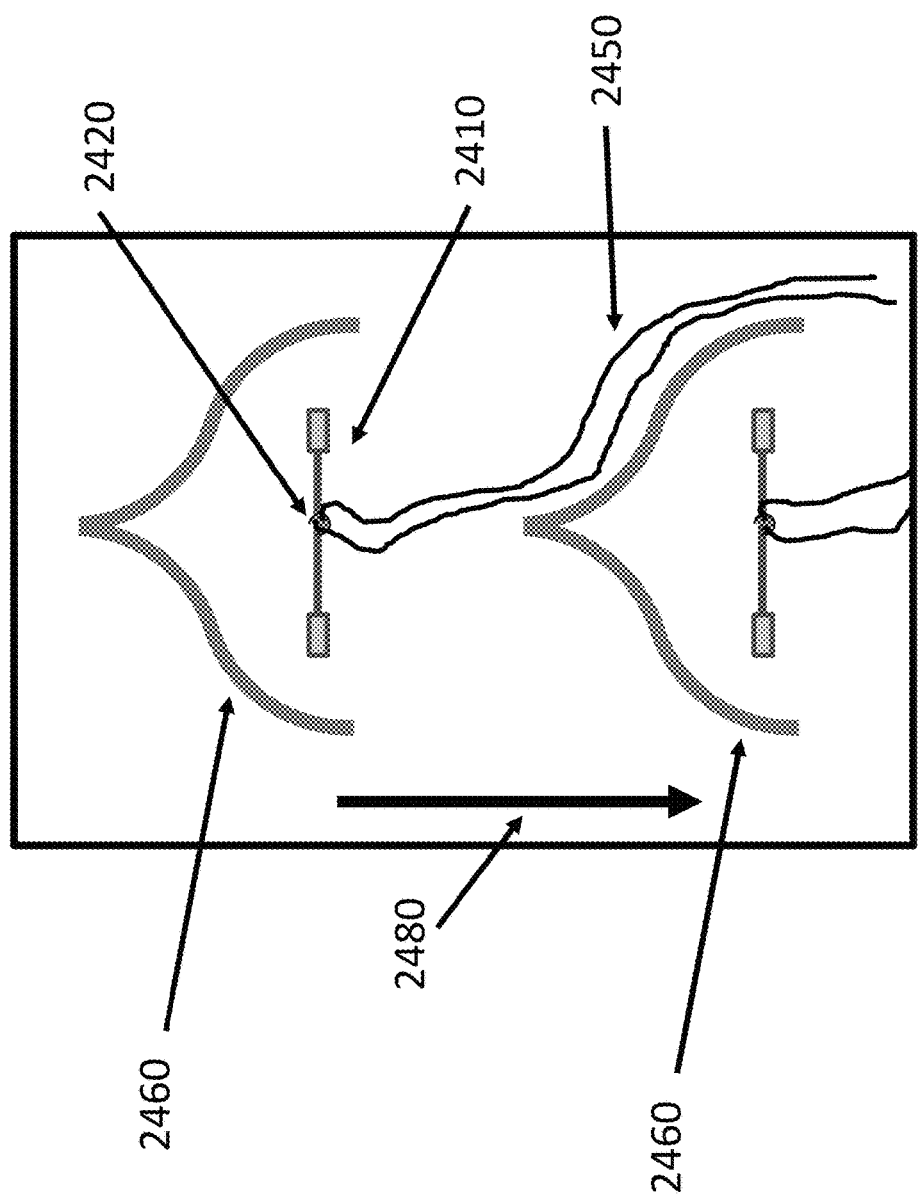
FIG. 24 shows an example a device with walls having shapes that divert the nucleic acids from neighboring nanoFET devices.

The walls can be made with any suitable shape. In some cases, the shapes of the walls are designed to re-direct the nucleic acid molecules from neighboring nanoFETs. FIG. 24 shows an example of walls having shapes that divert the nucleic acids from neighboring nanoFET devices. FIG. 24 provides a view looking down on the surface of a chip having an array of nanoFET devices 2410. The chip has walls 2460 that are arranged and shaped to allow for the nucleic acid strands 2450 from a neighboring nanoFET that is extended in the field 2480 to be diverted, and therefore not to interfere with the nanoFET that is located "down field" from that nanoFET. These walls can have any suitable shape, for example semicircular, V-shaped, or curved V-shaped as shown in FIG. 24. Thus, the walls of the invention can prevent interference with neighboring nanoFETs either by providing dimensions such that the nucleic acids extend over the wall, or by providing dimensions and shapes whereby the nucleic acids are diverted along the surface of the chip. The use and dimensions of the walls will be driven, in part, by the density of nanoFETs on a surface. In some cases, walls are implemented when the spacing between nanoFETs is less than about 500 nm, less than about 1 micron, less than about 2 microns, less than about 5 microns, or less than about 10 microns.

One issue we have found with respect to providing the tangential electric field across the device is that nanoFETs at different parts of the chip can reside at different potentials. To the extent that the field linearly drops across the device, we have addressed this issue by setting the potential of each row along the field to a different potential to compensate for the voltage drop, thus keeping each nanoFET at about the same potential with respect to its surrounding fluid. In some cases, however, the field drop is not linear across the device. For this situation we have found that it can be advantageous to provide a step in which the ground potential of each device is established independently. Thus, a potential measurement is carried out across the device at each nanoFET while the tangential electric field is applied, this is used to set the baseline potential at each nanoFET. In some cases, the potential across the chip varies over time, even if the same voltages are applied to the filed generating electrodes. This change can be slow over time, for example due to changes in local ionic content, or it can be intermittent, for example due to the flow of molecules or particles over the surface. For these cases, the step of establishing the baseline potentials of the nanoFETs is repeated over time, in some cases during the sequencing process in order to ensure a proper baseline potential for each nanoFET.

In some cases, a fluid flow field is used to tangentially pull the nucleic acid strands away from nanotube nanoFET. For example, microfluidic region is provided on the top of the chip to force fluid flow across the top of the chip to orient the nucleic acid molecules associated with the polymerase enzyme. We have determined that with nucleic acid molecules having a length of 1,000 bases to 30,000 bases or more, nucleic acid orientation can be obtained at relatively low flow rates. In some cases, where flow is used for nucleic acid orientation, reagents are recycled through the microfluidic region in order to avoid wasting reagents. This approach is particularly advantageous where reagent cost is a significant factor in the cost of sequencing.

In some cases, a region of the chip near the nanoFET is treated with reagents to which the nucleic acids are attracted or to which the nucleic acids tend to associate. The region of the chip can be a raised region. The region can be provided by a rod, puck, or particle that is bound to the surface near the nanoFET. In other cases, the rod, puck, or particle is not bound to the surface but will tend to pull the nucleic acid away from the polymerase as it is suspended in solution. The surface, rod, puck, or bead can be, for example, is passivated or coated with polycations such as polylysine. Other nucleic acid and DNA binding reagents that are known in the art can be used, for example, immobilized amine containing polymers and proteins such as single stranded binding proteins. The level of affinity of interaction is typically selected such that the affinity is strong enough that nucleic acids are held away from the nanotubes, but the affinity is not so strong that the nucleic acid is pulled out of the polymerase active site. The enzyme-nucleic acid interaction strength is also typically selected to be relatively strong to keep the nucleic acids from being pulled from the polymerase enzyme. In some cases, a topological tether is used to more securely hold the polymerase enzyme to the template nucleic acid. Such constructs are described, for example in U.S. Patent Application US 2015/0086994 which is incorporated herein by reference for all purposes. These constructs are useful for resisting DNA dissociation and for allowing for a wider range of binding affinities.

Lowered Background Noise—Nucleic Acid Binding Agents

One aspect of the invention is a method of lowering the background by providing agents that bind the template and nascent strand nucleic acid molecules associated with the polymerase. These nucleic acid binding molecules can associate with the nucleic acids in a way which pulls the nucleic acid molecules away from the nanotube of the nanoFET. One aspect of this binding is consolidation of the nucleic acids, lowering the range of motion of the nucleic acid molecules in a way that minimizes their interaction with the nanotube.

In some cases, the nucleic acid binding agents proteins such as single stranded DNA binding multimers. In some cases, these binding agents can be made using repeating protein units such as those found in transcription activator-like effector (TALE) binding domains. For example, TAL effectors are proteins that are secreted by Xanthomonas bacteria when they infect plants. The DNA binding domain in these proteins typically contains a repeated highly conserved 33-34 amino acid sequence with divergent 12th and 13th amino acids. These two positions, referred to as the Repeat Variable Diresidue (RVD), are highly variable and show a strong correlation with specific nucleotide recognition. This straightforward relationship between amino acid sequence and DNA recognition has allowed for the engineering of specific DNA-binding domains by selecting a combination of repeat segments containing the appropriate RVDs. These types of TALE proteins can be used to surround the nucleic acids associated with the polymerase enzyme effectively moving the nucleic acids beyond the Debye screening length.

Another approach to preventing the nucleic acids associated with the polymerase enzyme from interacting with the nanotube is to associate a virus particle to the polymerase such that the virus particle extends away from the nanotube. The nucleic acid molecules associated with the polymerase will tend to associate with the virus particle rather than to associate with the nanotube. For example, an M13 virus particle can be produced that coat protein pIII has affinity tags to attach it to the polymerase enzyme on the nanotube, and the coat protein pVIII interacts with the nucleic acid molecules.

Lowered Background Noise—Nascent Strand Cleavage

In some cases, the background is lowered by selectively degrading the nascent strand as it is formed. This can be done, for example, with nuclease enzymes. In some cases, an exonuclease is used that selectively degrades the nascent strand. For example, sequencing is carried out with a circular template molecule. An exonuclease is present that cleaves only nucleic acids having a free end, e.g. a 3' end. The exonuclease will cleave the nascent strand is it is produced without cleaving the circular template.

Another method of selective nascent strand cleavage uses nucleotides including dU analogs. A nascent strand comprising dU nucleotides is produced. A mixture of enzymes comprising an exonuclease that cleaves at dU sites is added during the sequencing reaction to selectively cleave the nascent strand at the dU sites, preventing it from extending and interacting with then nanotube and producing background. Such enzymes are known in the art. For example, a mixture of enzymes can be obtained from New England Biosciences that has Uracil DNA glycosylase (UDG) and a DNA glycosylase-lyase, Endonuclease VIII. UDG catalyzes the excision of a uracil base, forming an abasic (apyrimidinic) site while leaving the phosphodiester backbone intact. The lyase activity of Endonuclease VIII subsequently breaks the phosphodiester backbone at the 3' and 5' sides of the abasic site so that base-free deoxyribose is released.

Intentional Lowering of Debye Screening Length

As described herein, in some cases, it is useful to increase the Debye screening length near the nanotube in order to enhance the sensitivity of the nanotube to conductive labels. We have unexpectedly found that in some cases, it can be useful to intentionally lower the Debye screening length. While lowering the Debye screening length can make the nanotube less sensitive to labels, it also can make the nanotube less sensitive to ionic fluctuations in solution, lowering the background noise. If a conductivity label is chosen that interacts effectively and closely with the nanotube, the label can still be detected by the nanotube, but in a lower background environment.

The Debye screening length can be lowered by the addition of salt to the solution, increasing its ionic strength. In some cases, salt is added to lower the Debye screening length to about 2 nm, to about 1 nm, or to about 0.5 nm and still be able to detect the conductivity label, thus improving signal to noise.

Sparse Amplifier Array

The methods and systems of the invention can be carried out using any suitable array of nanoFET devices. In some aspects, sparse amplifier arrays are used wherein, in operation, only a small percentage of nanoFETs are addressed, and the remainder are not used. Such arrays are described in more detail in U.S. Patent Application entitled "SYSTEMS AND METHODS FOR SELECTIVELY ADDRESSING SPARSELY ARRANGED NANO-ELECTRONIC MEASUREMENT DEVICES" filed on Aug. 3, 2016, which is incorporated herein by reference for all purposes. In some cases, the percentage of nanoFETs addressed is less than 5%, less than 2%, less than 1%, less than 0.5%, or less than 0.2% of the total number of nanoFETs produced in the array. This aspect of the invention can be accomplished by the structure of the chip, the methods of addressing the chip, the methods of analyzing the chip, and combinations of any of these. In some cases, active switching assort amplifiers are used to selectively address productive nanoFETs having a single nanotube and single biomolecule (e.g. polymerase complex). In some preferred aspects, nanoFETs of the invention are produced using carbon nanotubes in combination with CMOS electronics.

For example, in some aspects the invention provides a method of addressing and analyzing a nanoFET chip wherein after the nanoFET array is produced, and after the biological molecule of interest such as the polymerase enzyme complex is attached, the chip is probed electrically to determine which of the nanoFETs have a single nanotube and a single biomolecule such as a polymerase. Then, during the measurement phase, for example, nucleic acid sequencing, only the nanoFETs having both a single nanotube and a single biomolecule (the productive nanoFETs) are addressed and analyzed. In a preferred method, the signals to the chip are re-configured such that the non-productive nanoFETs are completely bypassed. While it may seem counterintuitive to produce an array where only a small fraction of devices are used, we have found that unlike other uses of transistor arrays, the requirement of a single nanotube with a single polymerase will typically result in only a small number of the nanoFETs being used. With the devices and methods of the invention, we have developed a way of producing effective devices by actively using only the devices that are productive. In some cases, a device is produced having 100 million or more nanoFET devices, and when in use, for example nucleic acid sequencing, 2 million or fewer nanoFET devices are addressed and measured. This approach saves electronic and memory resources, and can provide higher quality information than for a device where all or a majority of the nanoFETs was addressed and measured.

For example say there are 1.7M devices in an array, this mean 1.7 M pairs of electrodes that could be bridged by zero, one, two or more nanotubes. We can typically only use those nanoFETs that have a single tube bridging. Even if we model the system that 100% of the tubes we transfer are potentially active (not multi-walled, not too big, etc) we can only get 37% of the electrode pairs to be useful if we use single entity loading based on Poisson statistics. If there is contamination of non-useful, for example, short-circuit producing nanotubes, this fraction will get directly multiplied by the efficiency above, so if there are 50% quality nanotubes we will get 18% active device fraction, and if there are 10% quality nanotubes we will get 3.7% active device fraction. In addition, where these nanotubes are subsequently derivitized, e.g. with a carboxylate moiety, if the derivitization is controlled by Poisson statistics, only 37% of these will be useful.

At this stage we would attach the biomolecule to the derivitized nanotubes, for example, the attachment of the polymerase sequencing complex. This reaction will have a yield, which will be affected, for example by the fraction of polymerase enzyme that is active. It is expected that this step can also result in a significant loss of yield of productive nanoFETs. Thus, even for a relatively well developed protocol, the yield of productive nanoFETs having a single nanotube and single polymerase will be relatively small in the range, for example of between 2% to 0.2%.

A solution provided as part of this invention is to make a chip with a vast over-supply of nanoFETs, but use an amplifier architecture that can handle only small fraction of that output. For example, we put 200,000,000 pixels onto a single die, then with 0.5% useful fraction this is yields 1,000,000 active useful devices. The output amplifier is produced such that even if a larger fraction were useful it would never have the capacity to read them all out.

In some aspects, the sparse amplifier comprises a chip that is able to simultaneously read out from multiple rows independently at the same time. In some embodiments the invention comprises an imaging chip such as a CMOS chip where each row of the imaging chip has a separate shift register. The following describes a non-limiting embodiment to illustrate this aspect of the invention.

The sparse amplifier can have e.g. 2000 columns×2000 rows or 3600 columns×3600 rows. As described above, only a fraction of the nanoFETs will be productive devices. Here, the productive device fraction is around 1.5% (due to various stages of yield and Poisson loading losses described above). There is an amplifier associated with each row, so in the second example, there are 3600 amplifiers. Instead of the typical row/column addressing that is used in CMOS imagers, here, there is a separate shift register for each row, or 3600 separate shift registers running alongside the switching transistors that are used to "electrify" the nanoFET devices when they are to be probed.

A key difference between this embodiment of the sparse chip and a conventional chip is that this chip is capable of simultaneously reading out from the chip sequencing data from a polymerase, for example, in column 1, row 16; and column 2, row 8; and column 3, row 22. In order to accomplish this, shift registers are provided for each row, allowing us to read independently from these different rows at the same time.

The operation of the shift register is illustrated by the following example. At the start of one "frame" of data collection (which would happen, for example, 1000 times per second), a "1" would be loaded in the first slot of every shift register and the rest of the values set to zero. Then a series of integers would be loaded into 3600 registers at the base of each column. The shift registers would then be pulsed N times if the integer is N . . . So, when the column receives a "15" it pulses its shift register 15 times. This has the effect of moving the "1" up to the $16^{th}$ row where it stops. Now the switches are driven from the value in shift register; so where it is a "0" then the switch remains off, and where it is a "1" then it links it with the amplifier. For this example we count on reading from the 50 best sensors in each row, so after 25 microseconds another integer is loaded, and the shift register is again pulsed N times followed by the acquisition of 25 microseconds more data. In implementing this approach, the number of bits used to represent the number is chosen to balance the requirements of the system. For example, more bits will result in more data that needs to be processed, but could provide more precision. In some cases, the system is designed such that some precision is lost at the benefit of easier data handling. For example, in the description above the device would bump each column about 50 times for each "frame" generating a significant amount of data.

The following documents provide teachings of various aspects of carrying out the instant invention. These documents are incorporated by reference herein in their entirety for all purposes.

1. Rosenblatt S, Yaish Y, Park J, Gore J, Sazonova V, McEuen P L. High performance electrolyte gated carbon nanotube transistors. Nano Letters. 2002; 2(8):869-72. doi: Doi 10.1021/N1025639a. PubMed PMID: ISI: 000177485500016.

2. Star A, Tu E, Niemann J, Gabriel J-CP, Joiner C S, Valcke C. Label-free detection of DNA hybridization using carbon nanotube network field-effect transistors. Proc Natl Acad Sci USA. 2006; 103(4):921-6. doi: 10.1073/pnas.0504146103.

3. Besteman K, Lee J-O, Wiertz F G M, Heering H A, Dekker C. Enzyme-Coated Carbon Nanotubes as Single-Molecule Biosensors. Nano Letters. 2003; 3(6):727-30. doi: 10.1021/nl034139u.

4. Heller I, Janssens A M, Mannik J, Minot E D, Lemay S G, Dekker C. Identifying the mechanism of biosensing with carbon nanotube transistors. Nano Letters. 2008; 8(2): 591-5. Epub 2007, Dec. 29. doi: 10.1021/nl072996i. PubMed PMID: 18162002.

5. Sorgenfrei S, Chiu C Y, Gonzalez R L, Yu Y J, Kim P, Nuckolls C, et al. Label-free single-molecule detection of DNA-hybridization kinetics with a carbon nanotube field-effect transistor. Nature Nanotechnology. 2011; 6(2):125-31. doi: 10.1038/nnano.2010.275. PubMed PMID: ISI: 000286968500015.

6. Goldsmith B R, Coroneus J G, Kane A A, Weiss G A, Collins P G. Monitoring Single-Molecule Reactivity on a Carbon Nanotube. Nano Letters. 2008; 8(1):189-94. doi: 10.1021/nl0724079.

7. Sorgenfrei S, Chiu C-y, Johnston M, Nuckolls C, Shepard K L. Debye Screening in Single-Molecule Carbon Nanotube Field-Effect Sensors. Nano Letters. 2011; 11(9): 3739-43. doi: 10.1021/nl201781q.

8. Goldsmith B R, Coroneus J G, Khalap V R, Kane A A, Weiss G A, Collins P G. Conductance-Controlled Point Functionalization of Single-Walled Carbon Nanotubes. Science. 2007; 315(5808):77-81. doi: 10.1126/science.1135303.

9. Rothberg J M, Hinz W, Rearick T M, Schultz J, Mileski W, Davey M, et al. An integrated semiconductor device enabling non-optical genome sequencing. Nature. 2011; 475(7356):348-52. doi:

10. Huang TcD, Sorgenfrei S, Gong P, Levicky R, Shepard K L. A 0.18-um CMOS Array Sensor for Integrated Time-Resolved Fluorescence Detection. Solid-State Circuits, IEEE Journal of. 2009; 44(5):1644-54.

11. Huang T-CD, Paul S, Gong P, Levicky R, Kymissis J, Amundson S A, et al. Gene expression analysis with an integrated CMOS microarray by time-resolved fluorescence detection. Biosensors and Bioelectronics. 2011; 26(5):2660-5. doi: 10.1016/j.bios.2010.03.001.

12. Johnston M L, Kymissis I, Shepard K L. FBAR-CMOS Oscillator Array for Mass-Sensing Applications. Sensors Journal, IEEE. 2010; 10(6):1042-7.

13. Lei N, Ramakrishnan S, Shi P, Orcutt J S, Yuste R, Kam L C, et al. High-resolution extracellular stimulation of dispersed hippocampal culture with high-density CMOS multielectrode array based on non-Faradaic electrodes. Journal of neural engineering. 2011; 8(4):044003. Epub 2011, Jul. 5. doi: 10.1088/1741-2560/8/4/044003. PubMed PMID: 21725154.

14. Levine P M, Gong P, Levicky R, Shepard K L. Real-time, multiplexed electrochemical DNA detection using an active complementary metal-oxide-semiconductor biosensor array with integrated sensor electronics. Biosensors and Bioelectronics. 2009; 24(7):1995-2001.

15. Levine P M, Ping G, Levicky R, Shepard K L. Active CMOS Sensor Array for Electrochemical Biomolecular Detection. Solid-State Circuits, IEEE Journal of. 2008; 43(8):1859-71.

16. Patounakis G, Shepard K L, Revicky R. Active CMOS array sensor for time-resolved fluorescence detection. IEEE Journal of Solid-State Circuits. 2006; 41(11):2521-30.

17. Rosenstein J K, Wanunu M, Merchant C A, Drndic M, Shepard K L. Integrated nanopore sensing platform with sub-microsecond temporal resolution. Nat Meth. 2012; 9(5): 487-92.

18. Schwartz D, Gong P, Shepard K L. Time-resolved Forster-resonance-energy-transfer DNA assay on an active CMOS microarray. Biosensors and Bioelectronics. 2008; 24(3):383-90.

19. Bronson J E, Fei J, Hofman J M, Gonzalez Jr R L, Wiggins C H. Learning Rates and States from Biophysical Time Series: A Bayesian Approach to Model Selection and Single-Molecule FRET Data. Biophys J. 2009; 97(12):3196-205. doi: DOI: 10.1016/j.bpj.2009.09.031.

20. Fei J, Bronson J E, Hofman J M, Srinivas R L, Wiggins C H, Gonzalez R L. Allosteric collaboration between elongation factor G and the ribosomal L1 stalk directs tRNA movements during translation. Proceedings of the National Academy of Sciences. 2009; 106(37):15702-7. doi: 10.1073/pnas.0908077106.

21. Lu H P, Xun L, Xie X S. Single-Molecule Enzymatic Dynamics. Science. 1998; 282(5395):1877-82. doi: 10.1126/science.282.5395.1877.

22. van Oijen A M, Blainey P C, Crampton D J, Richardson C C, Ellenberger T, Xie X S. Single-Molecule Kinetics of λ Exonuclease Reveal Base Dependence and Dynamic Disorder. Science. 2003; 301(5637):1235-8. doi: 10.1126/science.1084387.

23. Meric I, Caruso V, Caldwell R, Hone J, Shepard K L, Wind S J. Hybrid carbon nanotube-silicon complementary metal oxide semiconductor circuits. Journal of Vacuum Science & Technology B. 2007; 25(6):2577-80. doi: 10.1116/1.2800322. PubMed PMID: ISI:000251611900161.

24. Kang S J, Kocabas C, Ozel T, Shim M, Pimparkar N, Alam M A, et al. High-performance electronics using dense, perfectly aligned arrays of single-walled carbon nanotubes. Nat Nano. 2007; 2(4):230-6.

25. Polk B J, Stelzenmuller A, Mijares G, MacCrehan W, Gaitan M. Ag/AgCl microelectrodes with improved stability for microfluidics. Sensors and Actuators B: Chemical. 2006; 114(1):239-47. doi: 10.1016/j.snb.2005.03.121.

26. Wang L, Meric I, Huang P Y, Gao Q, Gao Y, Tran H, et al. One-Dimensional Electrical Contact to a Two-Dimensional Material. Science. 2013; 342(6158):614-7. doi: 10.1126/science.1244358. PubMed PMID: WOS: 000326334300047.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. A nanoFET device for sequencing a single nucleic acid template molecule comprising:
   a source, a drain and a gate, the gate comprising a nanowire;
   a single polymerase enzyme complex bound to the gate, the polymerase enzyme complex comprising a polymerase enzyme complexed with the template nucleic acid;
   wherein the polymerase is bound to the gate non-covalently through a polymer binding agent, or a pair of polymer binding agents, wherein the polymer binding agent or the pair of polymer binding agents has two polymer strands, each polymer strand interacting in multiple places with the nanowire such that the polymerase is in a central location between the two polymer strands with the polymer strands extending away from the polymerase complex along the nanowire in both directions.

2. The nanoFET device of claim 1 wherein the nanowire comprises a carbon nanotube.

3. The nanoFET device of claim 1 wherein the nanowire comprises a silicon nanowire.

4. The nanoFET device of claim 1 wherein the polymer binding agent comprises a protein or polypeptide.

5. The nanoFET device of claim 1 wherein the polymerase comprises a phi29 type polymerase.

6. The nanoFET device of claim 1 wherein the polymerase comprises a modified phi29 polymerase.

7. The nanoFET device of claim 1 wherein the polymerase is covalently bound to the polymer binding agent.

8. The nanoFET device of claim 1 wherein the nanowire further comprises one or more polymer binding agents which are not bound to the polymerase enzyme complex that coat the nanowire.

9. The nanoFET device of claim 8 wherein substantially all of the nanowire is coated with polymer binding agent.

10. The nanoFET device of claim 1 wherein the polymer binding agent is cross-linked to the nanowire.

11. The nanoFET device of claim 1 wherein the polymer binding agent binds to the nanowire through hydrophobic binding moieties.

12. The nanoFET device of claim 11 wherein the hydrophobic binding moieties comprise one or more polycyclic aromatic moieties.

13. The nanoFET device of claim 1 wherein the polymer binding agent wraps around the nanowire.

14. A chip for sequencing a plurality of single nucleic acid template molecules comprising:
    a plurality of nanoFET devices of claim 1
       wherein the substrate is configured such that the plurality of nanoFET devices come into contact with a sequencing reaction mixture comprising a plurality of types of nucleotide analogs each having a different conductivity label; and
    a plurality of electrical connection sites for bringing current and voltage to the nanoFETs, and for receiving electrical signals from the nanoFETs.

15. The chip of claim 14 wherein the substrate comprises about 1,000 nanoFET devices to about 10 million nanoFET devices.

16. The chip of claim 14 wherein the substrate comprises about 10,000 nanoFET devices to about 1 million nanoFET devices.

17. The chip of claim 14 wherein the substrate comprises electronic elements for one or more of: providing electrical signals to the nanoFETs, measuring the electrical signals at the nanoFETs, analog to digital conversion, signal processing, and data storage.

18. The chip of claim 14 wherein the electrical elements are CMOS elements.

* * * * *